United States Patent
Park et al.

(10) Patent No.: US 12,180,185 B2
(45) Date of Patent: *Dec. 31, 2024

(54) COMPOUND AS PROTEIN KINASE INHIBITOR, AND PHARMACEUTICAL COMPOSITION COMPRISING THEREOF

(71) Applicant: HK INNO.N Corporation, Seoul (KR)

(72) Inventors: Ji-Yeon Park, Gyeonggi-do (KR);
Seung Chan Kim, Gyeonggi-do (KR);
So Young Ki, Gyeonggi-do (KR);
Ye-Ri Shim, Seoul (KR)

(73) Assignee: HK inno.N Corporation (KR)

( * ) Notice: Subject to any disclaimer, the term of this patent is extended or adjusted under 35 U.S.C. 154(b) by 799 days.

This patent is subject to a terminal disclaimer.

(21) Appl. No.: 17/294,226

(22) PCT Filed: Nov. 14, 2019

(86) PCT No.: PCT/KR2019/015516
§ 371 (c)(1),
(2) Date: May 14, 2021

(87) PCT Pub. No.: WO2020/101382
PCT Pub. Date: May 22, 2020

(65) Prior Publication Data
US 2022/0009902 A1    Jan. 13, 2022

(30) Foreign Application Priority Data
Nov. 15, 2018  (KR) .................. 10-2018-0140578

(51) Int. Cl.
C07D 401/14    (2006.01)
C07D 401/04    (2006.01)
C07D 405/14    (2006.01)
C07D 409/14    (2006.01)
C07D 417/14    (2006.01)

(52) U.S. Cl.
CPC ......... *C07D 401/14* (2013.01); *C07D 401/04* (2013.01); *C07D 405/14* (2013.01); *C07D 409/14* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 5,057,517 | A | 10/1991 | Johnston et al. |
| 7,098,333 | B2 | 8/2006 | Gillespie et al. |
| 9,133,200 | B2 | 9/2015 | Gonzalez Rodriguez et al. |
| 10,793,551 | B2 * | 10/2020 | Ernst ..................... A61P 35/00 |
| 10,889,586 | B2 | 1/2021 | Wu |
| 11,053,224 | B2 | 7/2021 | Liang et al. |
| 2004/0127538 | A1 | 7/2004 | Oinuma et al. |
| 2008/0146565 | A1 | 6/2008 | Dunn et al. |
| 2014/0170110 | A1 | 6/2014 | Eastwood et al. |
| 2014/0302010 | A1 | 10/2014 | Klar et al. |
| 2015/0126535 | A1 | 5/2015 | Gonzales et al. |
| 2016/0289207 | A1 | 10/2016 | Demong |
| 2018/0244654 | A1 | 8/2018 | Schiltz |
| 2021/0171544 | A1 | 6/2021 | Lee et al. |
| 2024/0051957 | A1 | 2/2024 | Kim et al. |
| 2024/0300943 | A1 | 9/2024 | Lee et al. |

FOREIGN PATENT DOCUMENTS

| | | |
|---|---|---|
| CA | 2319275 | 8/1999 |
| CA | 2404594 | 10/2001 |
| CA | 2424303 | 4/2002 |
| CA | 2537731 | 3/2005 |
| CA | 2539548 | 3/2005 |
| CA | 2575808 | 2/2006 |
| CA | 2588627 | 7/2006 |
| CA | 2610828 | 12/2006 |
| CA | 2625442 | 4/2007 |
| CA | 2358998 | 11/2007 |
| CA | 2672172 | 7/2008 |
| CA | 2686903 | 11/2008 |
| CA | 2709883 | 6/2009 |
| CA | 2709806 | 7/2009 |
| CA | 2718727 | 10/2009 |
| CA | 2728559 | 1/2010 |
| CA | 2729552 | 1/2010 |
| CA | 2736522 | 3/2010 |
| CA | 2561950 | 4/2010 |
| CA | 2738348 | 4/2010 |

(Continued)

OTHER PUBLICATIONS

Brown, (2010). Bioisosteres in Medicinal Chemistry. John Wiley & Sons) (Year: 2010).*
CN Office Action in Chinese Appln. No. 201880067864.1, dated Jan. 11, 2022, 19 pages (with English Translation).
IN Hearing Notice in Indian Appln. No. 202137026444, dated Mar. 25, 2022, 3 pages (with English Translation).
Jones et al., "Design and Synthesis of a pan-Janus Kinase Inhibitor Clinical Candidate (PF-06263276) Suitable for Inhaled and Topical Delivery for the Treatment of Inflammatory Diseases of the Lungs and Skin," Just-Accepted Manuscript, Journal of Medicinal Chemistry, 2016, 63 pages, DOI:10.1021/acs.jmedchem.6b01634.
Li et al., "Design and optimization of (3-aryl-1H-indazol-6-yl)spiro[cyclopropane-1,3'-indolin]-2'-ones as potent PLK4 inhibitors with oral antitumor efficacy," Bioorganic & Medicinal Chemistry Letters, 2016, 26(19):4625-4630, DOI:10.1016/j.bmcl.2016.08.063.

(Continued)

*Primary Examiner* — Jeffrey S Lundgren
*Assistant Examiner* — Anthony Joseph Seitz
(74) *Attorney, Agent, or Firm* — Fish & Richardson P.C.

(57) ABSTRACT

The present invention provides a novel compound having a protein kinase inhibitory activity, stereoisomers thereof or pharmaceutically acceptable salts thereof. The compound according to the present invention, stereoisomers thereof or pharmaceutically acceptable salts thereof are effective in preventing or treating protein kinase-related diseases such as cancers, autoimmune diseases, neurological diseases, metabolic diseases, infections or the like by showing a protein kinase inhibitory activity.

10 Claims, No Drawings

(56) References Cited

FOREIGN PATENT DOCUMENTS

| | | |
|---|---|---|
| CA | 2746221 | 7/2010 |
| CA | 2407593 | 1/2011 |
| CA | 2767079 | 1/2011 |
| CA | 2496842 | 2/2011 |
| CA | 2770155 | 2/2011 |
| CA | 2781056 | 5/2011 |
| CA | 2786950 | 6/2011 |
| CA | 2799156 | 11/2011 |
| CA | 2804347 | 1/2012 |
| CA | 2804845 | 1/2012 |
| CA | 2809911 | 3/2012 |
| CA | 2834548 | 11/2012 |
| CA | 2839767 | 12/2012 |
| CA | 2849340 | 3/2013 |
| CA | 2857193 | 6/2013 |
| CA | 2854093 | 7/2013 |
| CA | 2878412 | 1/2014 |
| CA | 2879448 | 1/2014 |
| CA | 2901929 | 10/2014 |
| CA | 2904048 | 10/2014 |
| CA | 2918910 | 1/2015 |
| CA | 2926340 | 4/2015 |
| CA | 2935329 | 7/2015 |
| CA | 2940666 | 9/2015 |
| CA | 2942957 | 10/2015 |
| CA | 2949163 | 11/2015 |
| CA | 2952083 | 1/2016 |
| CA | 2958966 | 3/2016 |
| CA | 2982493 | 11/2016 |
| CA | 2999937 | 4/2017 |
| CA | 3002558 | 5/2017 |
| CA | 3003930 | 5/2017 |
| CA | 3016196 | 9/2017 |
| CA | 3020778 | 10/2017 |
| CA | 2794153 | 1/2018 |
| CA | 3036987 | 3/2018 |
| CA | 3048217 | 6/2018 |
| CA | 3050770 | 6/2018 |
| CA | 3047212 | 8/2018 |
| CA | 2803156 | 1/2019 |
| CA | 3071024 | 2/2019 |
| CA | 3071900 | 2/2019 |
| CA | 3077238 | 4/2019 |
| CA | 3079292 | 4/2019 |
| CA | 3082156 | 4/2019 |
| CA | 3080806 | 5/2019 |
| CA | 3083374 | 5/2019 |
| CA | 3084058 | 6/2019 |
| CA | 3085427 | 6/2019 |
| CA | 3088025 | 8/2019 |
| CA | 3101223 | 11/2019 |
| CA | 3101368 | 11/2019 |
| CA | 3102598 | 12/2019 |
| CA | 3109192 | 2/2020 |
| CA | 3107426 | 3/2020 |
| CA | 3107624 | 3/2020 |
| CN | 102574857 | 7/2012 |
| CN | 105263930 | 1/2016 |
| CN | 106478651 | 3/2017 |
| CN | 108084153 A | 5/2018 |
| EA | 14706 | 2/2011 |
| EA | 31882 | 3/2019 |
| EP | 2489663 A1 | 8/2012 |
| JP | 2003523942 | 8/2003 |
| JP | 2005524621 | 8/2005 |
| JP | 2006199617 | 8/2006 |
| JP | 2009521504 | 6/2009 |
| JP | 2010511655 | 4/2010 |
| JP | 2012532152 | 12/2012 |
| JP | 2014509625 | 4/2014 |
| JP | 2015522620 | 8/2015 |
| JP | 2016516791 | 6/2016 |
| JP | 2018529770 | 10/2018 |
| JP | 2021500339 | 1/2021 |
| KR | 10-2014-0004637 | 1/2014 |
| KR | 10-2014-0027318 | 3/2014 |
| KR | 10-2019-0039823 | 4/2019 |
| KR | 10-2019-0043437 | 4/2019 |
| KR | 10-2019-0068626 | 6/2019 |
| RU | 2485106 C2 | 6/2006 |
| RU | 2016104388 | 8/2017 |
| WO | WO-0100213 A1 * | 1/2001 ........... C07D 401/14 |
| WO | WO2001000213 | 1/2001 |
| WO | WO2002055084 | 7/2002 |
| WO | WO2002083648 | 10/2002 |
| WO | 2007-004944 A1 | 1/2007 |
| WO | WO 2007070589 | 6/2007 |
| WO | WO2008079907 | 7/2008 |
| WO | WO2008090181 | 7/2008 |
| WO | WO2008135785 | 11/2008 |
| WO | WO2009027732 | 3/2009 |
| WO | WO2009049028 | 4/2009 |
| WO | WO2009131687 | 10/2009 |
| WO | 2010-068806 A1 | 6/2010 |
| WO | 2011-003418 A1 | 1/2011 |
| WO | 2011-005119 A1 | 1/2011 |
| WO | WO2011163424 | 12/2011 |
| WO | WO2012020787 | 2/2012 |
| WO | WO 2012069202 | 5/2012 |
| WO | WO2013020369 | 2/2013 |
| WO | WO 2014071031 | 5/2014 |
| WO | WO2014075318 | 5/2014 |
| WO | WO2014137728 | 9/2014 |
| WO | 2014-170248 A1 | 10/2014 |
| WO | WO2015006754 | 1/2015 |
| WO | 2015-192119 A1 | 12/2015 |
| WO | WO2015187684 | 12/2015 |
| WO | WO2016183094 | 11/2016 |
| WO | WO2017050938 | 3/2017 |
| WO | 2017-087905 A1 | 5/2017 |
| WO | 2017-098467 A1 | 6/2017 |
| WO | WO2017161004 | 9/2017 |
| WO | WO2018154578 | 8/2018 |
| WO | WO 2019078619 | 4/2019 |

OTHER PUBLICATIONS

AU Office Action in Australian Appln. No. 2018353759, dated Apr. 26, 2022, 10 pages.
Belikov et al., "The Relationship Between a Chemical Structure and Properties of Substances and their Action to Organism," Pharmaceutical Chemistry, Moscow Publishing House, MEDpress-inform, 2007, Section 2.6, pp. 27-29.
RU Office Action in Russian Appln. No. 2021117137/04(036124), dated Mar. 17, 2022, 22 pages (with English Translation).
Shahani et al., "A 2,6,9-hetero-trisubstituted purine inhibitor exhibits potent biological effects against multiple myeloma cells," Bioorganic & Medicinal Chemistry, 2013, 21:5618-5628.
International Search Report for PCT/KR2019/015516, mailed Mar. 9, 2020. 3 pages.
International Search Report for PCT/KR2018/012270, mailed Feb. 1, 2019. 4 pages.
Search Report for RU2020115890 (corresponds to PCT/KR2018/012270) dated Oct. 8, 2020. 3 pages.
"4-Acyl Pyrroles: Mimicking Acetylated Lysines in Histone Code Reading**", Lucas, et al., Angewandte Chemie, International Edition, 2013, 52, pp. 14055-14059.
"Identification of Novel Smoothened Ligands Using Structure-Based Docking", Lacroix, et al., PLOS One, 11(8), e0160365/1-20, Aug. 4, 2016.
"Selective inhibitor of Janus tyrosine kinase 3, PNU156804, prolongs allograft survival and acts synergistically with cyclosporine but additively with rapamycin", Stepkowski, et al., Blood, Jan. 5, 2002, vol. 99, No. 2, pp. 680-689.
Gurzov et al., "The JAK/STAT Pathway In Obesity and Diabetes", The FEBS Journal, 2016, 283:3002-3015.
JP Office Action in Japanese Appln. No. 2020-521905, dated Nov. 2021, 8 pages with English Translation.
Kontzias et al. "Jakinibs: A New Class of Kinase Inhibitors in Cancer and Autoimmune Disease", Current Opinion in Pharmacology, 2012, 12:464-470.

(56) References Cited

OTHER PUBLICATIONS

Nicolas et al., "The Role of JAK-STAT Signaling Within The CNS" Landes Bioscience, 2013, 2(1):122925.
Tsirigotis et al., "Treatment of Experimental Candia Sepsis with a Janus Kinase Inhibitor Controls Inflammation and Prolongs Survival", Antimicrobial Agents and Chemotherapy, Dec. 2015, 59(12):7367-7373.
Belikov et al., "The Relationship Between the Structure of Molecules of Substances and their Effect on the Body", Pharmaceutical Chemistry, Chapter 2.2, 1993, pp. 43-47.
Durnov et al., "Pediatric Oncology", Second Edition Medicina, 2003, pp. 139.
Dyson et al., "Chemistry of Synthetic Drug Substances", MIR, 1964, pp. 12-19, with English Abstract.
JP Office Action in Japanese Appln. No. 2020-521905, dated Apr. 27, 2021, 15 pages with English Translation.
Kasatkina et al., "Protein Kinases: Variety and Classification", Transduction of Hormonal Signal, Research Work, 2014.
KR Office Action for App No. KR 10-2018-0140578, dated Mar. 25, 2020 (with English Translation) 11 pages.
PubChem CID 11020179, National Center for Biotechnology Information, PubChem Compound Summary for CID 11020179, 6-Phenyl-7H-purin-2-amine, https://pubchem.ncbi.nlm.nih.gov/compound/6-Phenyl-7H-purin-2-amin, accessed Jun. 21, 2021, create date Oct. 26, 2006.
RU Office Action in Russian Appln. No. 2020115890/04(026059), dated Apr. 29, 2021, 29 pages with English Translation.
Tyukavkina et al., Biorganic Chemistry, published by "Drofa", Moscow, 2005, pp. 83-85.
AU Examination Report No. 1 in Australian Appln. No. 2018353759, dated Jun. 23, 2021, 8 pages.
CA Examination Report in Canadian Appln. No. 3082156, dated Jun. 11, 2021, 6 pages.
Golub et al., "Molecular Classification of Cancer: Class Discovery and Class Prediction by Gene Expression Monitoring", Science, 1999, 286:531-537.
IN Examination Report in Indian Appln No. 202137026444, dated Aug. 13, 2021, 5 pages with English Translation.
Pala et al., "Virtual Screening and Biological Validation of Novel Influenza Virus PA Endonuclease Inhibitors", ACS Med. Chem. Lett., Aug. 2015, 6(8):866-871.
Rituraj et al., "Schizophrenia: A Look Forward with Zinc06025953", International Journal of Pharmaceutical Sciences and Research, 2017, 8(5):2122-2133.
EP Search Report in a European Appln. No. 19885184.2, dated Jun. 24, 2022, 7 pages.
ID Office Action in Indonesian Appln. No. P00202003535, dated Jun. 30, 2022, 4 pages (with English Translation).
ID Office Action in Indonesian Appln. No. P00202104463, dated Jul. 18, 2022, 6 pages (with English Translation).
JP Office Action in Japanese Appln. No. 2021-526602, dated Jun. 7, 2022, 5 pages (with English Translation).
MX Office Action in Mexican Appln. No. MX/a/2020/003868, dated Jun. 21, 2022, 18 pages (with English Translation).
EP Search Report in a European Appln. No. 18869085.3, dated Nov. 16, 2022, 6 pages.
Kiselgof et al., "6-(2-Furanyl)-9H-purin-2-amine derivatives as A2A adenosine antagonists," Bioorganic & Medicinal Chemistry Letters. 2005, 15:2119-2122.
Shahani et al., "A 2,6,9-hetero-trisubstituted purine inhibitor exhibits potent biological effects against multiple myeloma cells," with Supporting Information, Bioorganic & Medicinal Chemistry, 2013, 21:5618-5628.
KR Office Action for App No. KR 10-2017-0135515, dated Nov. 1, 2018 (with English translation) (21 pages).
KR Office Action for App No. KR 10-2019-0064740, dated Jan. 2, 2020 (English translation) (15 pages).
KR Notice of Allowance for App No. KR 10-2019-0064740, dated Jul. 1, 2020 (English translation) (5 pages).

KR Notice of Allowance for App No. KR 10-2019-0098472, dated May 4, 2020 (English translation) (5 pages).
RU Office Action for App No. RU2020115890/04, dated Oct. 15, 2020 (English translation) (25 pages).
Anderson et al., "Chapter 34: Preparation of water-soluble organic compound by salt formation", The Practice of Medicinal Chemistry, Wermuth (ed.), Technomics, Inc., Sep. 25, 1999, pp. 347-365 (with Machine translation, 39 pages in total).
AU Office Action in Australian Appln. No. 2022237154, mailed on Jun. 17, 2024, 2 pages.
AU Office Action in Australian Appln. No. 2022239128, mailed on Apr. 22, 2024, 2 pages.
Bastin et al., "Salt Selection and Optimisation Procedures for Pharmaceutical New Chemical Entities," Organic Process Research & Development, Sep. 2000, 4(5):427-435.
Belikov et al., "The Relationship Between the Structure of Molecules of Substances and their Effect on the Body", Pharmaceutical Chemistry, Chapter 2.2, 1993, pp. 43-47 (with English abstract).
Bernshtein, "Molecular crystal polymorphism," Moscow Science, 2007, Chapter 7.3.2 Bioavailability, pp. 324-330 (with English translation, 13 pages in total).
CA Office Action in Canadian Appln. No. 3212253, mailed on Oct. 4, 2024, 3 pages.
CA Office Action in Canadian Appln. No. 3212256, mailed on Oct. 4, 2024, 4 pages.
Caira, "Crystalline Polymorphism of Organic Compounds," Topics in Current Chemistry, 1998, 198: 163-208 (p. 164, section 3.1, p. 188).
Experimental Chemistry Courses (Secondary) (Jikken Kagaku Kouza (Zoku)), "Separation and Purification", The Chemical Society of Japan (ed.), Maruzen Co., Ltd., Jan. 25, 1967, pp. 159-178, 186-187 (with Machine translation, 45 pages in total).
International Preliminary Report on Patentability in International Appln. No. PCT/KR2022/003703, mailed on Sep. 12, 2023, 11 pages (with Machine translation).
International Preliminary Report on Patentability in International Appln. No. PCT/KR2022/003702, mailed on Sep. 12, 2023, 14 pages (with English Translation).
International Search Report and Written Opinion in International Appln. No. PCT/KR2022/003703, mailed on Jun. 27, 2022, 17 pages (with English translation).
International Search Report and Written Opinion in International Appln. No. PCT/KR2022/003702, mailed on Jun. 27, 2021, 21 pages (with English Translation).
JP Office Action in Japanese Appln. No. 2023-556847, mailed on Jul. 23, 2024, 11 pages (with English translation).
JP Office Action in Japanese Appln. No. 2023-556851, mailed on Aug. 27, 2024, 8 pages (with English translation).
Kuznetsova, "Guidelines," Irkutsk State University (GOVPOIGU), Department of General Physics, 2005, Page 3, 2nd Paragraph.
Mit'kina et al., "Stress studies and photostability as a part of pharmaceutical drug development data," The Bulletin of the Scientific Centre for Expert Evaluation of Medicinal Products, 2015, (2):9-12, 11 pages (with English Translation).
New and Pharmaceutical Examination (Shin-Yakuzaigaku), The Third Revised Edition, Okano (ed.), Nankaido Co., Ltd., Apr. 10, 1987, Page 111 (with Machine translation, 5 pages in total).
New Pharmaceutical Preparation (Shin-Seizaigaku), Nakai et al. (ed), Nanzando Co., Ltd., Apr. 25, 1984, pp. 102-103, 232-233 (with Machine translation, 12 pages in total).
Ooshima, "Crystallization of Polymorphs and Pseudo-polymorphs and Its Control," Pharm Stage, Jan. 15, 2007, 6(10):48-53 (with Machine translation, 22 pages in total).
Polymorphism and Crystallization of the Pharmaceutical Drugs, Ashizawa (ed.), Maruzen Planet Co. Ltd., Sep. 20, 2002, pp. 3-16, 273-278 (with Machine translation, 40 pages in total).
Rodriguez-Spong et al., "General principles of pharmaceutical solid polymorphism: a supramolecular perspective," Adv Drug Deliv Rev, Feb. 23, 2004, 56(3):241-274.
RU Office Action and Search Report in Russian Appln. No. 2023126280/04(058068), mailed on Apr. 15, 2024, 31 pages (with English translation).

(56) References Cited

OTHER PUBLICATIONS

RU Office Action and Search Report in Russian Appln. No. 2023126285/04(058073), mailed on Apr. 4, 2024, 23 pages (with English translation).

RU Search Report for App No. RU2020115890/04, dated Oct. 8, 2020, 5 pages (with English translation).

Saal et al., "Pharmaceutical salts: A summary on doses of salt formers from the Orange Book," European Journal of Pharmaceutical Sciences, Jun. 2013, 49(4):614-623 (pp. 614-161 "Introduction").

Sarma et al., "Solid forms of pharmaceuticals: Polymorphs, salts and cocrystals," Korean J Chem Eng, Jan. 31, 2011, 28(2):315-322 (p. 316, left col. lines 6-17).

Sharma et al., "Polymorphism in pharmaceutical compounds," Advances and Futuristic Trends in Material Science, 2011, pp. 39-48 (part 5, p. 43-44).

Smirnova et al., "Chapter 11.2 Relationship of crystal structure of substance, pharmacokinetics and efficacy of drug," Clinical pharmacokinetics: theoretical, applied and analytical aspects: a manual, (edited by Kukes), 2009, pp. 235-248 (with Machine translation).

Takata, "API Form Screening and Selection in the Drug Discovery Stage", Pharm Stage, Jan. 15, 2007, 6(10):20-25 (with Machine translation, 19 pages in total).

The Ministry of Health, Labour and Welfare (Japan), "The Japanese Pharmacopoeia," 16th edition, 2011, pp. 64-68 and p. 2070 (with corresponding English pp. 74-80 and 2253-2255), 19 pages in total.

Variankaval et al., "From form to function: Crystallization of active pharmaceutical ingredients," AIChE Journal, Jul. 2008, 54(7): 1682-1688 (c.1682 "Crystal Form").

Yamano, "Approach to Crystal Polymorph in Process Research of New Drug", Journal from The Society of Synthetic Organic Chemistry, Sep. 2007, 65(9):907-913 (with Machine translation, 21 pages in total).

U.S. Appl. No. 16/757,182, filed Apr. 17, 2020, Lee et al..
U.S. Appl. No. 18/282,177, filed Sep. 14, 2023, Kim et al..
U.S. Appl. No. 18/282,182, filed Sep. 14, 2023, Lee et al..

* cited by examiner

COMPOUND AS PROTEIN KINASE INHIBITOR, AND PHARMACEUTICAL COMPOSITION COMPRISING THEREOF

CROSS-REFERENCE TO RELATED APPLICATIONS

This application is a U.S. National Stage application and claims priority to International Application No. PCT/KR2019/015516, filed Nov. 14, 2019, which claims priority to South Korean Application No. 10-2018-0140578, filed Nov. 15, 2018. The contents of all of the prior applications are incorporated herein by reference in their entirety.

TECHNICAL FIELD

The present invention relates to a novel compound as a protein kinase inhibitor, a pharmaceutical composition including the same, and a pharmaceutical use thereof, which inhibits an activity of a protein kinase as a phosphoenzyme and thus may be used valuably in preventing or treating diseases related thereto.

BACKGROUND ART

Protein kinases are enzymes which control various intracellular processes by phosphorylating other proteins and thus by regulating the activities, positions and functions of the proteins. Abnormality of control function of such protein kinases is closely associated with a mechanism of diseases such as cancers, autoimmune diseases, neurological diseases, metabolic diseases, infections or the like.

Janus kinase (JAK) is a kinase which plays a key role in a signal transduction system of cytokines. The JAK plays a critical role in hematopoiesis, innate immunity and acquired immunity and thus becomes an important target as a therapeutic agent for treating diseases such as cancers, autoimmune diseases, neurological diseases, metabolic diseases, infections or the like.

The JAK is a protein which consists of about 1,150 amino acids and has a molecular weight of approximately 120-130 kDa, and the JAK is classified into four types: JAK1, JAK2, JAK3 and TYK2. The JAK is located in an intracellular receptor of an inflammatory cytokine. The inflammatory cytokines (IL-2, IL-4, IL-6, IL-7, IL-9, IL-15, IL-21, GM-CSF, G-CSF, EPO, TPO, IFN-a (IFN-alpha), IFN-b (IFN-beta), IFN-g (IFN-gamma), etc.) bind with the receptors, then phosphorylated, and then deliver a signal of the inflammatory cytokines into cells through an action with STAT molecules. An excessive activation of signal transduction through such various inflammatory cytokines causes an immune system of our body to attack the human body and thus leads to the occurrence of autoimmune diseases.

Thus, it is expected to identify a more improved therapeutic effect on autoimmune diseases than existing therapeutic agents by developing a drug for inhibiting a receptor kinase of such inflammatory cytokines.

DISCLOSURE OF INVENTION

Technical Problem

An objective of the present invention is to provide a novel compound showing a protein kinase inhibitory activity, stereoisomers thereof or pharmaceutically acceptable salts thereof.

Also, an objective of the present invention is to provide a method for preparing the compound of the present invention, stereoisomers thereof or pharmaceutically acceptable salts thereof.

Moreover, an objective of the present invention is to provide a pharmaceutical composition for treating or preventing protein kinase-related diseases, comprising the compound of the present invention, stereoisomers thereof or pharmaceutically acceptable salts thereof as an active ingredient.

Furthermore, an objective of the present invention is to provide a method for preventing or treating protein kinase-related diseases, including a step of administering a therapeutically effective amount of the compound of the present invention, stereoisomers thereof or pharmaceutically acceptable salts thereof into a subject.

In addition, an objective of the present invention is to provide a use of the compound of the present invention, stereoisomers thereof or pharmaceutically acceptable salts thereof in preparation of a medicament for preventing or treating protein kinase-related diseases.

Besides, an objective of the present invention is to provide a use of the compound of the present invention, stereoisomers thereof or pharmaceutically acceptable salts thereof for preventing or treating protein kinase-related diseases.

Solution to Problem

Protein Kinase Inhibitor Compound and Method for Preparing the Same

To solve the problems above, the present invention provides a compound represented by the following Formula 1, stereoisomers thereof or pharmaceutically acceptable salts thereof:

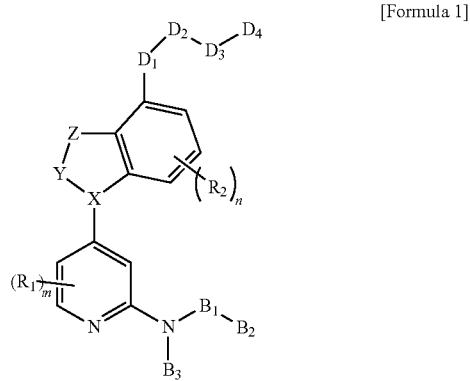

[Formula 1]

in Formula 1, $R_1$ is H, $C_{1-6}$ alkyl, $C_{1-6}$ alkoxy, $C_{1-6}$ hydroxyalkyl, $C_{1-6}$ cyanoalkyl, $C_{1-6}$ haloalkyl, hydroxy, cyano, halogen, C(=O)—OH, C(=O)—O—$C_{1-6}$ alkyl, S(=O)$_2$—$C_{1-6}$ alkyl, aryl or heteroaryl;

X is C-$A_1$ or N,

Y is C-$A_2$ or N-$A_4$,

Z is C-$A_3$ or N-$A_5$, wherein at least one of X, Y and Z includes N;

at least one of a bond between X and Y or a bond between Y and Z is a double bond, and if the bond between X and Y is the double bond, $A_1$ or $A_4$ is null;

$A_1$ to $A_5$ are each independently H, $C_{1-6}$ alkyl, $C_{1-6}$ alkoxy, $C_{1-6}$ hydroxyalkyl, $C_{1-6}$ haloalkyl, $C_{1-6}$ cyanoalkyl, C(=O)—OH, C(=O)—O—C$_{1-6}$ alkyl, S(=O)$_2$—C$_{1-6}$ alkyl, —C(=O)—N—C$_{1-6}$ haloalkyl, aryl or heteroaryl;

R$_2$ is H, C$_{1-6}$ alkyl, C$_{1-6}$ alkoxy, C$_{1-6}$ hydroxyalkyl, C$_{1-6}$ cyanoalkyl, C$_{1-6}$ haloalkyl, hydroxy, cyano, halogen, C(=O)—OH, C(=O)—O—C$_{1-6}$ alkyl, S(=O)$_2$—C$_{1-6}$ alkyl, aryl or heteroaryl;

n and m are each independently 0, 1, 2 or 3;

B$_1$ is —C(=O)—, —C(=S)—, —C(=O)—NR$_3$— or a single bond;

B$_2$ is C$_{3-7}$ cycloalkyl, 5-6-membered heterocycloalkyl, aryl or heteroaryl;

B$_3$ is H or C$_{1-6}$ alkyl;

D$_1$ is —NR$_3$—;

D$_2$ is —C(=O)—, —C(=S)—, —S(=O)$_2$— or a single bond;

D$_3$ is —NR$_3$—,

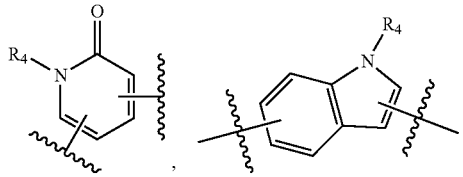

or a single bond;

D$_4$ is H, C$_{1-6}$ alkyl, C$_{1-6}$ alkenyl, C$_{1-6}$ haloalkyl, C$_{1-6}$ cyanoalkyl, C$_{3-7}$ cycloalkyl, 5-6-membered heterocycloalkyl, aryl or heteroaryl;

wherein at least one H of C$_{1-6}$ alkyl, C$_{1-6}$ alkenyl, C$_{1-6}$ haloalkyl or C$_{1-6}$ cyanoalkyl may be substituted with C$_{3-7}$ cycloalkyl, aryl, heteroaryl or cyano, at least one H of C$_{3-7}$ cycloalkyl or 5-6-membered heterocycloalkyl may be substituted with C$_{1-6}$ alkyl, C$_{1-6}$ haloalkyl, C$_{1-6}$ cyanoalkyl, cyano or halogen, and at least one H of aryl or heteroaryl may be substituted with C$_{1-6}$ alkyl, C$_{1-6}$ alkoxy, C$_{1-6}$ haloalkyl, C$_{1-6}$ hydroxyalkyl, C$_{1-6}$ cyanoalkyl, C$_{1-6}$ thioalkyl, hydroxy, cyano, nitro or halogen; and R$_3$ and R$_4$ are each independently H, C$_{1-6}$ alkyl or C$_{1-6}$ haloalkyl.

According to one embodiment of the present invention, the compound represented by Formula 1 may include one of compounds represented by the following Formula 1-1, Formula 1-2 and Formula 1-3:

[Formula 1-1]

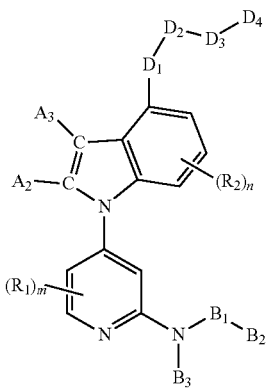

[Formula 1-2]

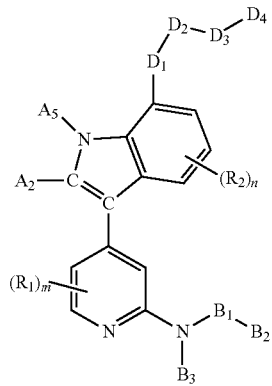

[Formula 1-3]

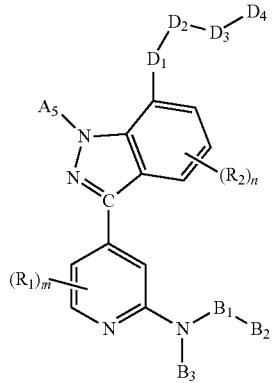

in Formulas,

R$_1$ is H, C$_{1-6}$ alkyl, C$_{1-6}$ alkoxy, C$_{1-6}$ hydroxyalkyl, C$_{1-6}$ cyanoalkyl, C$_{1-6}$ haloalkyl, hydroxy, cyano, halogen, C(=O)—OH, C(=O)—O—C$_{1-6}$ alkyl, S(=O)$_2$—C$_{1-6}$ alkyl, aryl or heteroaryl;

A$_2$ to A$_5$ are each independently H, C$_{1-6}$ alkyl, C$_{1-6}$ alkoxy, C$_{1-6}$ hydroxyalkyl, C$_{1-6}$ haloalkyl, C$_{1-6}$ cyanoalkyl, C(=O)—OH, C(=O)—O—C$_{1-6}$ alkyl, S(=O)$_2$—C$_{1-6}$ alkyl, —C(=O)—N—C$_{1-6}$ haloalkyl, aryl or heteroaryl;

R$_2$ is H, C$_{1-6}$ alkyl, C$_{1-6}$ alkoxy, C$_{1-6}$ hydroxyalkyl, C$_{1-6}$ cyanoalkyl, C$_{1-6}$ haloalkyl, hydroxy, cyano, halogen, C(=O)—OH, C(=O)—O—C$_{1-6}$ alkyl, S(=O)$_2$—C$_{1-6}$ alkyl, aryl or heteroaryl;

n and m are each independently 0, 1, 2 or 3;

B$_1$ is —C(=O)—, —C(=S)—, —C(=O)—NR$_3$— or a single bond;

B$_2$ is C$_{3-7}$ cycloalkyl, 5-6-membered heterocycloalkyl, aryl or heteroaryl;

B$_3$ is H or C$_{1-6}$ alkyl;

D$_1$ is —NR$_3$—;

D$_2$ is —C(=O)—, —C(=S)—, —S(=O)$_2$— or a single bond;

D$_3$ is —NR$_3$—,

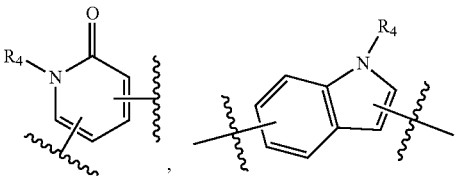

or a single bond;

D₄ is H, $C_{1-6}$ alkyl, $C_{1-6}$ alkenyl, $C_{1-6}$ haloalkyl, $C_{1-6}$ cyanoalkyl, $C_{3-7}$ cycloalkyl, 5-6-membered heterocycloalkyl, aryl or heteroaryl;

wherein at least one H of $C_{1-6}$ alkyl, $C_{1-6}$ alkenyl, $C_{1-6}$ haloalkyl or $C_{1-6}$ cyanoalkyl may be substituted with $C_{3-7}$ cycloalkyl, aryl, heteroaryl or cyano, at least one H of $C_{3-7}$ cycloalkyl or 5-6-membered heterocycloalkyl may be substituted with $C_{1-6}$ alkyl, $C_{1-6}$ haloalkyl, $C_{1-6}$ cyanoalkyl, cyano or halogen, and at least one H of aryl or heteroaryl may be substituted with $C_{1-6}$ alkyl, $C_{1-6}$ alkoxy, $C_{1-6}$ haloalkyl, $C_{1-6}$ hydroxyalkyl, $C_{1-6}$ cyanoalkyl, $C_{1-6}$ thioalkyl, hydroxy, cyano, nitro or halogen; and R₃ and R₄ are each independently H, $C_{1-6}$ alkyl or $C_{1-6}$ haloalkyl.

According to one embodiment of the present invention, the compound represented by Formula 1 may include a compound represented by the following Formula 2:

[Formula 2]

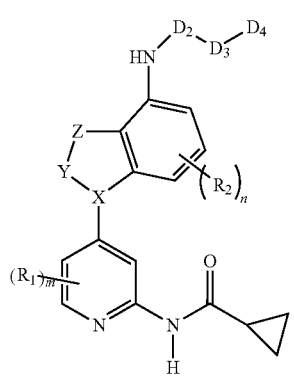

in Formula 2,

R₁ is H, $C_{1-6}$ alkyl, $C_{1-6}$ alkoxy, $C_{1-6}$ hydroxyalkyl, $C_{1-6}$ cyanoalkyl, $C_{1-6}$ haloalkyl, hydroxy, cyano, halogen, C(=O)—OH, C(=O)—O—$C_{1-6}$ alkyl, S(=O)₂—$C_{1-6}$ alkyl, aryl or heteroaryl;

X is C-A₁ or N,

Y is C-A₂ or N-A₄,

Z is C-A₃ or N-A₅, wherein at least one of X, Y and Z includes N;

at least one of a bond between X and Y or a bond between Y and Z is a double bond, and if the bond between X and Y is the double bond, A₁ or A₄ is null;

A₁ to A₅ are each independently H, $C_{1-6}$ alkyl, $C_{1-6}$ alkoxy, $C_{1-6}$ hydroxyalkyl, $C_{1-6}$ haloalkyl, $C_{1-6}$ cyanoalkyl, C(=O)—OH, C(=O)—O—$C_{1-6}$ alkyl, S(=O)₂—$C_{1-6}$ alkyl, —C(=O)—N—$C_{1-6}$ haloalkyl, aryl or heteroaryl;

R₂ is H, $C_{1-6}$ alkyl, $C_{1-6}$ alkoxy, $C_{1-6}$ hydroxyalkyl, $C_{1-6}$ cyanoalkyl, $C_{1-6}$ haloalkyl, hydroxy, cyano, halogen, C(=O)—OH, C(=O)—O—$C_{1-6}$ alkyl, S(=O)₂—$C_{1-6}$ alkyl, aryl or heteroaryl;

n and m are each independently 0 or 1;

D₂ is —C(=O)—, —C(=S)—, —S(=O)₂— or a single bond;

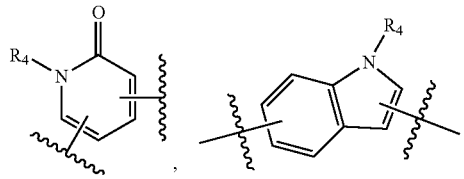

D₄ is H, $C_{1-6}$ alkyl, $C_{1-6}$ alkenyl, $C_{1-6}$ cyanoalkyl, $C_{3-7}$ cycloalkyl, 5-6-membered heterocycloalkyl, aryl or heteroaryl;

wherein at least one H of $C_{1-6}$ alkyl, $C_{1-6}$ alkenyl or $C_{1-6}$ cyanoalkyl may be substituted with $C_{3-7}$ cycloalkyl, aryl, heteroaryl or cyano, at least one H of $C_{3-7}$ cycloalkyl or 5-6-membered heterocycloalkyl may be substituted with $C_{1-6}$ alkyl, $C_{1-6}$ haloalkyl, $C_{1-6}$ cyanoalkyl, cyano or halogen, and at least one H of aryl or heteroaryl may be substituted with $C_{1-6}$ alkyl, $C_{1-6}$ alkoxy, $C_{1-6}$ haloalkyl, $C_{1-6}$ hydroxyalkyl, $C_{1-6}$ cyanoalkyl, $C_{1-6}$ thioalkyl, hydroxy, cyano, nitro or halogen; and R₃ and R₄ are each independently H, $C_{1-6}$ alkyl or $C_{1-6}$ haloalkyl.

According to another embodiment aspect of the present invention, in Formula 1,

R₁ is H, $C_{1-6}$ alkyl or $C_{1-6}$ alkoxy;

X is C-A₁ or N,

Y is C-A₂ or N-A₄,

Z is C-A₃ or N-A₅, wherein at least one of X, Y and Z includes N;

at least one of a bond between X and Y or a bond between Y and Z is a double bond, and if the bond between X and Y is the double bond, A₁ or A₄ is null;

A₁ to A₅ are each independently H, $C_{1-6}$ alkyl or —C(=O)—N—$C_{1-6}$ haloalkyl;

R₂ is H, $C_{1-6}$ alkyl or $C_{1-6}$ heteroaryl;

n and m are each independently 0 or 1;

D₂ is —C(=O)—;

D₃ is —NR₃—,

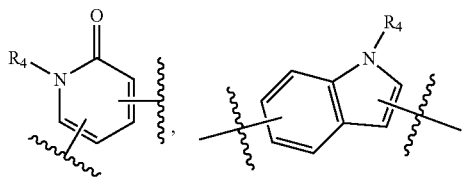

or a single bond;

D₄ is H, $C_{1-6}$ alkyl, $C_{1-6}$ alkenyl, $C_{1-6}$ cyanoalkyl, $C_{3-7}$ cycloalkyl, 5-6-membered heterocycloalkyl, aryl or heteroaryl;

wherein at least one H of $C_{1-6}$ alkyl, $C_{1-6}$ alkenyl or $C_{1-6}$ cyanoalkyl may be substituted with $C_{3-7}$ cycloalkyl, aryl, heteroaryl or cyano, at least one H of $C_{3-7}$ cycloalkyl or 4-6-membered heterocycloalkyl may be substituted with $C_{1-6}$ alkyl, $C_{1-6}$ cyanoalkyl or cyano, and at least one H of aryl or heteroaryl may be substituted with $C_{1-6}$ alkyl, $C_{1-6}$ alkoxy, $C_{1-6}$ haloalkyl or cyano; and R₃ and R₄ are each independently H, $C_{1-6}$ alkyl or $C_{1-6}$ haloalkyl.

According to another embodiment aspect of the present invention,
in Formula 1,
$R_1$ is H;
X is N;
Y is C-$A_2$;
Z is C-$A_3$;
a bond between Y and Z is a double bond;
$A_2$ and $A_3$ are each independently H;
$R_2$ is H;
n and m are each independently 0;
$D_2$ is —C(=O)—;
$D_3$ is —$NR_3$—,

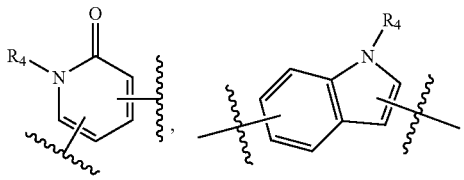

or a single bond;
$D_4$ is H, $C_{1-6}$ alkyl, $C_{1-6}$ alkenyl, $C_{1-6}$ cyanoalkyl, $C_{3-7}$ cycloalkyl, 5-6-membered heterocycloalkyl, aryl or heteroaryl;
wherein at least one H of $C_{1-6}$ alkyl, $C_{1-6}$ alkenyl or $C_{1-6}$ cyanoalkyl may be substituted with aryl, heteroaryl or cyano,
at least one H of $C_{3-7}$ cycloalkyl or 5-6-membered heterocycloalkyl may be substituted with $C_{1-6}$ cyanoalkyl or cyano, and
at least one H of aryl or heteroaryl may be substituted with $C_{1-6}$ alkyl, $C_{1-6}$ alkoxy, cyano, nitro or halogen; and
$R_3$ and $R_4$ are each independently H or $C_{1-6}$ alkyl.

According to another embodiment aspect of the present invention,
in Formula 1,
$R_1$ is H, $C_{1-6}$ alkyl or $C_{1-6}$ alkoxy;
X is C-$A_1$;
Y is C-$A_2$;
Z is N-$A_5$, wherein at least one of X, Y and Z includes N;
a bond between X and Y is a double bond, and if the bond between X and Y is the double bond, $A_1$ is null;
$A_2$ and $A_5$ are each independently H, $C_{1-6}$ alkyl or —C(=O)—N—$C_{1-6}$ haloalkyl;
$R_2$ is H or $C_{1-6}$ alkyl;
n and m are each independently 0 or 1;
$D_2$ is —C(=O)—;
$D_3$ is —$NR_3$—,

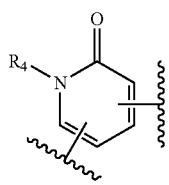

or a single bond;
$D_4$ is H, $C_{1-6}$ alkyl, $C_{1-6}$ alkenyl, $C_{1-6}$ cyanoalkyl, $C_{3-7}$ cycloalkyl, 5-6-membered heterocycloalkyl, aryl or heteroaryl;
wherein at least one H of $C_{1-6}$ alkyl, $C_{1-6}$ alkenyl or $C_{1-6}$ cyanoalkyl may be substituted with $C_{3-7}$ cycloalkyl, heteroaryl or cyano,
at least one H of $C_{3-7}$ cycloalkyl or 5-6-membered heterocycloalkyl may be substituted with $C_{1-6}$ alkyl or cyano, and
at least one H of aryl or heteroaryl may be substituted with $C_{1-6}$ alkyl, $C_{1-6}$ haloalkyl or cyano; and
$R_3$ and $R_4$ are each independently H, $C_{1-6}$ alkyl or $C_{1-6}$ haloalkyl.

According to another embodiment aspect of the present invention,
in Formula 1,
$R_1$ is FI;
X is C-$A_1$;
Y is N-$A_4$;
Z is N-$A_5$;
a bond between X and Y is a double bond;
$A_1$, $A_4$ and $A_5$ are each independently H;
$R_2$ is H;
n and m are each independently 0;
$D_2$ is —C(=O)—;
$D_3$ is a single bond;
$D_4$ is $C_{1-6}$ alkenyl, wherein at least one H of $C_{1-6}$ alkenyl may be substituted with cyano; and
$R_3$ is H.

Throughout the present specification, the concepts defined as follows are used when defining the compounds of Formula 1 and Formula 2. The following definitions are also applied to the terms used either individually or as a part of a larger group thereof throughout the present specification, unless otherwise particularly indicated.

The term "alkyl" means a straight, branched or ring-shaped hydrocarbon radical re-spectively, when being used independently or in combination with "heteroalkyl" in which each carbon atom may be arbitrarily substituted with at least one of cyano, hydroxy, alkoxy, oxo, halogen, carbonyl, sulfonyl, cyanyl, etc.

The term "alkoxy" refers to —O-alkyl, in which alkyl is the same as defined above.

The term "heteroalkyl" means alkyl including at least one heteroatom selected from N, O and S.

The term "aryl" means an aromatic group including phenyl, naphthyl, etc., and may be arbitrarily substituted with at least one of alkyl, alkoxy, halogen, hydroxy, carbonyl, sulfonyl, cyanyl, etc.

The term "heteroaryl" refers to a 5- to 7-membered aromatic, monocyclic ring, which includes at least one heteroatom, for example, 1 to 4, or in some exemplary embodiments 1 to 3 heteroatoms selected from N, O and S, and in which remaining ring atoms are carbons; a 8- to 12-membered bicyclic ring, which includes at least one heteroatom, for example, 1 to 4, or in some exemplary embodiments 1 to 3 heteroatoms selected from N, O and S, and in which remaining ring atoms are carbons, at least one ring is aromatic, and at least one heteroatom is present in an aromatic ring; and a 11- to 14-membered tricyclic ring, which includes at least one heteroatom, for example, 1 to 4, or in some exemplary embodiments 1 to 3 heteroatoms selected from N, O and S, and in which remaining ring atoms are carbons, at least one ring is aromatic, and at least one heteroatom is present in an aromatic ring. An example of a heteroaryl group includes pyridyl, pyrazinyl, 2,4-pyrimidinyl, 3,5-pyrimidinyl, 2,4-imidazolyl, isoxazolyl, oxazolyl, thiazolyl, thiadiazolyl, tetrazolyl, thienyl, ben-zothienyl, furyl, benzofuryl, benzoimidazolyl, indolyl, indolinyl, pyrrolyl, thiophenyl, pyridizinyl, triazolyl, quinolinyl, pyrazolyl, pyrrolopyridinyl, pyrazolopyridinyl, ben-zoxazolyl, benzothiazolyl, indazolyl and 5,6,7,8-tetrahydroisoquinoline, but is not limited thereto.

The term "heterocycloalkyl" refers to a form which includes 1 to 4 heteroatoms selected from N, O and S, may be arbitrarily fused with benzo or cycloalkyl, and is saturated or partially saturated or aromatic. An appropriate heterocycloalkyl may include, for example, piperidinyl, piperazinyl, tetrahydrofuranyl, pyrrolidinyl, pyranyl, etc., but is not limited thereto.

The term "halo(gen)" means a substituent selected from fluoro, chloro, bromo and iodo.

Also, in Formula 1, Formulas 1-1 to 1-3 and Formula 2, "n" means the number of substituents which may be substituted. If n is 0, it means that hydrogen atoms are all substituted.

Moreover, in the present invention, an expression that a monovalent substituent excluding one hydrogen may be null means "not present" and an expression that a divalent substituent excluding two hydrogens may be null means a "single bond".

Besides, the terms and abbreviations used in the present specification have their original meanings, unless defined otherwise.

In the present invention, examples of the compounds represented by Formula 1 are as follows.

1) N-(4-(7-(2-cyano-3-methylbut-2-enamido)-1H-indol-3-yl)pyridin-2-yl)cyclopropanecarboxamide
2) N-(3-(2-(cyclopropanecarboxamido)pyridin-4-yl)-1H-indol-7-yl)-3,5-difluorobenzamide
3) N-(3-(2-(cyclopropanecarboxamido)pyridin-4-yl)-1H-indol-7-yl)cyclohexanecarboxamide
4) N-(3-(2-(cyclopropanecarboxamido)pyridin-4-yl)-1H-indol-7-yl)-2-fluoroisonicotinamide
5) N-(3-(2-(cyclopropanecarboxamido)pyridin-4-yl)-1H-indol-7-yl)-3,5-dimethylbenzamide
6) N-(3-(2-(cyclopropanecarboxamido)pyridin-4-yl)-1H-indol-7-yl)thiazole-5-carboxamide
7) N-(4-(7-butyramido-1H-indol-3-yl)pyridin-2-yl)cyclopropanecarboxamide
8) N-(4-(7-(2-cyanoacetamido)-1H-indol-3-yl)-5-methylpyridin-2-yl)cyclopropanecarboxamide
9) N-(4-(7-(2-cyano-3-methylbut-2-enamido)-1H-indol-3-yl)-6-methylpyridin-2-yl)cyclopropanecarboxamide
10) N-(4-(7-(2-cyanoacetamido)-1H-indol-3-yl)pyridin-2-yl)cyclopropanecarboxamide
11) 4-cyano-N-(3-(2-(cyclopropanecarboxamido)pyridin-4-yl)-1H-indol-7-yl)tetrahydro-2H-pyran-4-carboxamide
12) N-(4-(7-(2-cyano-3-methylbut-2-enamido)-1H-indol-3-yl)-5-methylpyridin-2-yl)cyclopropanecarboxamide
13) N-(4-(7-(2-(1-cyanocyclopropyl)acetamido)-1H-indol-3-yl)pyridin-2-yl)cyclopropanecarboxamide
14) N-(4-(7-(2-cyanopropanamido)-1H-indol-3-yl)pyridin-2-yl)cyclopropanecarboxamide
15) N-(4-(7-(2-cyano-3-methylbut-2-enamido)-5-methyl-1H-indol-3-yl)pyridin-2-yl)cyclopropanecarboxamide
16) N-(3-(2-(cyclopropanecarboxamido)pyridin-4-yl)-5-methyl-1H-indol-7-yl)-5-methylpyrazine-2-carboxamide
17) N-(4-(7-(2,3-dimethylbut-2-enamido)-1H-indol-3-yl)pyridin-2-yl)cyclopropanecarboxamide
18) N-(4-(7-(2-(4-methylpiperazin-1-yl)propanamido)-1H-indol-3-yl)pyridin-2-yl)cyclopropanecarboxamide
19) N-(4-(7-(2-cyano-3-methylbut-2-enamido)-1H-indol-3-yl)-6-methoxypyridin-2-yl)cyclopropanecarboxamide
20) N-(4-(7-(2-cyanoacetamido)-1H-indol-3-yl)-6-methoxypyridin-2-yl)cyclopropanecarboxamide
21) N-(3-(2-(cyclopropanecarboxamido)pyridin-4-yl)-1H-indol-7-yl)-4-(trifluoromethyl)thiazole-2-carboxamide
22) (E)-N-(4-(7-(2-cyano-3-phenylacrylamido)-1H-indol-3-yl)pyridin-2-yl)cyclopropanecarboxamide
23) N-(3-(2-(cyclopropanecarboxamido)pyridin-4-yl)-1H-indol-7-yl)-1H-pyrrole-2-carboxamide
24) N-(3-(2-(cyclopropanecarboxamido)pyridin-4-yl)-1H-indol-7-yl)-4-methylnicotinamide
25) (E)-N-(4-(7-(2-cyano-3-(thiophen-2-yl)acrylamido)-1H-indol-3-yl)pyridin-2-yl)cyclopropanecarboxamide
26) N-(4-(7-(2-cyano-3-methylbut-2-enamido)-1-methyl-1H-indol-3-yl)pyridin-2-yl)cyclopropanecarboxamide
27) 4-cyano-N-(3-(2-(cyclopropanecarboxamido)pyridin-4-yl)-1H-indol-7-yl)benzamide
28) N-(3-(2-(cyclopropanecarboxamido)pyridin-4-yl)-1H-indol-7-yl)-6-methylnicotinamide
29) N-(3-(2-(cyclopropanecarboxamido)pyridin-4-yl)-1H-indol-7-yl)-6-(trifluoromethyl)nicotinamide 30) N-(3-(2-(cyclopropanecarboxamido)pyridin-4-yl)-1H-indol-7-yl)-5,6-difluoronicotinamide
31) N-(3-(2-(cyclopropanecarboxamido)pyridin-4-yl)-1H-indol-7-yl)-5-fluoronicotinamide
32) 6-chloro-N-(3-(2-(cyclopropanecarboxamido)pyridin-4-yl)-1H-indol-7-yl)nicotinamide
33) N-(3-(2-(cyclopropanecarboxamido)pyridin-4-yl)-1H-indol-7-yl)-1H-pyrazole-3-carboxamide
34) N-(3-(2-(cyclopropanecarboxamido)pyridin-4-yl)-1H-indol-7-yl)-1-methyl-2-oxo-1,2-dihydropyridine-3-carboxamide
35) 2-cyano-N-(3-(2-(cyclopropanecarboxamido)pyridin-4-yl)-1H-indol-7-yl)isonicotinamide
36) N-(3-(2-(cyclopropanecarboxamido)pyridin-4-yl)-1H-indol-7-yl)-4-ethyl-1H-pyrrole-2-carboxamide
37) 3-(2-(cyclopropanecarboxamido)pyridin-4-yl)-N-(2,2,2-trifluoroethyl)-7-(3-(2,2,2-trifluoroethyl)ureido)-1H-indole-1-carboxamide
38) N-(3-(2-(cyclopropanecarboxamido)pyridin-4-yl)-1H-indol-7-yl)-3-fluorobenzamide
39) N-(4-(7-(3-(2,2,2-trifluoroethyl)ureido)-1H-indol-3-yl)pyridin-2-yl)cyclopropanecarboxamide
40) N-(4-(4-(2-cyano-3-methylbut-2-enamido)-1H-indol-1-yl)pyridin-2-yl)cyclopropanecarboxamide
41) N-(4-(4-(2-cyanoacetamido)-1H-indol-1-yl)pyridin-2-yl)cyclopropanecarboxamide
42) N-(1-(2-(cyclopropanecarboxamido)pyridin-4-yl)-1H-indol-4-yl)-1H-pyrrole-2-carboxamid
43) N-(1-(2-(cyclopropanecarboxamido)pyridin-4-yl)-1H-indol-4-yl)-2-methylthiazole-5-carboxamid
44) N-(1-(2-(cyclopropanecarboxamido)pyridin-4-yl)-1H-indol-4-yl)-3,5-difluorobenzamide
45) N-(1-(2-(cyclopropanecarboxamido)pyridin-4-yl)-1H-indol-4-yl)-1-methyl-2-oxo-1,2-dihydropyridine-3-carboxamide
46) N-(4-(4-(2-cyano-3-(thiophen-2-yl)acrylamido)-1H-indol-1-yl)pyridin-2-yl)cyclopropanecarboxamide
47) 4-cyano-N-(1-(2-(cyclopropanecarboxamido)pyridin-4-yl)-1H-indol-4-yl)benzamide
48) N-(4-(4-(2-cyano-3-phenylacrylamido)-1H-indol-1-yl)pyridin-2-yl)cyclopropanecarboxamide
49) N-(1-(2-(cyclopropanecarboxamido)pyridin-4-yl-1H-indol-4-yl)-1-methyl-1H-indole-2-carboxamide
50) 4-cyano-N-(1-(2-(cyclopropanecarboxamido)pyridin-4-yl)-1H-indol-4-yl)tetrahydro-2H-pyran-4-carboxamide
51) 2-cyano-N-(1-(2-(cyclopropanecarboxamido)pyridin-4-yl)-1H-indol-4-yl)isonicotinamide
52) N-(1-(2-(cyclopropanecarboxamido)pyridin-4-yl)-1H-indol-4-yl)-2-fluoroisonicotinamide
53) N-(1-(2-(cyclopropanecarboxamido)pyridin-4-yl)-1H-indol-4-yl)-2,3-difluoroisonicotinamide
54) N-(4-(4-(2-cyanopropanamido)-1H-indol-1-yl)pyridin-2-yl)cyclopropanecarboxamide
55) N-(1-(2-(cyclopropanecarboxamido)pyridin-4-yl)-1H-indol-4-yl)-1H-pyrazole-3-carboxamide
56) N-(1-(2-(cyclopropanecarboxamido)pyridin-4-yl)-1H-indol-4-yl)-3-fluoro-4-methoxybenzamide
57) (1R,2S)-2-cyano-N-(1-(2-(cyclopropanecarboxamido)pyridin-4-yl)-1H-indol-4-yl)cyclopropane-1-carboxamide
58) N-(4-(4-(2-(1-cyanocyclopropyl)acetamido)-1H-indol-1-yl)pyridin-2-yl)cyclopropanecarboxamide
59) N-(1-(2-(cyclopropanecarboxamido)pyridin-4-yl)-1H-indol-4-yl)-6-methylnicotinamide
60) N-(4-(4-(2,3-dimethylbut-2-enamido)-1H-indol-1-yl)pyridin-2-yl)cyclopropanecarboxamide
61) N-(4-(4-(3-(2,4-difluorophenyl)ureido)-1H-indol-1-yl)pyridin-2-yl)cyclopropanecarboxamide
62) N-(4-(4-(3-(2,2,2-trifluoroethyl)ureido)-1H-indol-1-yl)pyridin-2-yl)cyclopropanecarboxamide
63) N-(4-(7-(2-cyano-3-methylbut-2-enamido)-1H-indazol-3-yl)pyridin-2-yl)cyclopropanecarboxamide Meanwhile, the compounds according to the present invention may have an asymmetric carbon, and may be present as R or S isomers, racemates, mixtures of diastereomers and individual diastereomers, and all the isomers and mixtures are included in the scope of the present invention. In other words, if asymmetric carbon(s) are included in a structure of Formula 1, it should be appreciated that the stereoisomers are all included therein, unless a direction thereof is described otherwise.

Hereinafter, a method for preparing the compound represented by Formula 2, which is one embodiment of Formula 1, is described on the basis of an exemplary reaction formula for better understanding of the present invention. However, it should be interpreted by those skilled in the art, to which the present invention pertains, that the compound of Formula 1 or Formula 2 may be prepared by means of various methods based on a structure of Formula 1 or Formula 2 and such methods are all included in the scope of the present invention. In other words, it should be appreciated that the compound according to the present invention may be prepared by arbitrarily combining various synthesis methods which are described in the present specification or disclosed in the prior art and this belongs to the scope of the present invention. In the following reaction formula, all the substituents are the same as defined above, unless indicated otherwise.

As the acid, base and reaction solvent used in the compounds of the present invention, those commonly used in the art may be used therein without limitation. For example, as the acid, the followings may be used: inorganic acids such as hydrochloric acid, sulfuric acid, nitric acid, phosphoric acid, hydrobromic acid, hydriodic acid, etc.; organic carboxylic acids such as tartaric acid, formic acid, citric acid, acetic acid, adipic acid, trichloroacetic acid, trifluoroacetic acid, gluconic acid, benzoic acid, lactic acid, fumaric acid, maleic acid, etc.; and sulfonic acids such as methanesulfonic acid, benzenesulfonic acid, p-toluenesulfonic acid, naphthalenesulfonic acid or the like. As the base, the followings may be used: NaH, $K_2CO_3$, $Na_2CO_3$, $NaHCO_3$, $K_3PO_4$, KOH, NaOH, LiOH, n-BuLi, sec-BuLi, LiHMDS, etc. As the reaction solvent, the followings may be used: DCM, THF, dioxane, MeOH, EtOH, hexane, EtOAC, ether, DMF, DMSO, toluene, xylene, etc., or mixed solvents thereof, etc.

In one embodiment, a method for synthesizing the compound of Formula 2 according to the present invention may be exemplified by the following Reaction Formula 1:

[Reaction Formula 1]

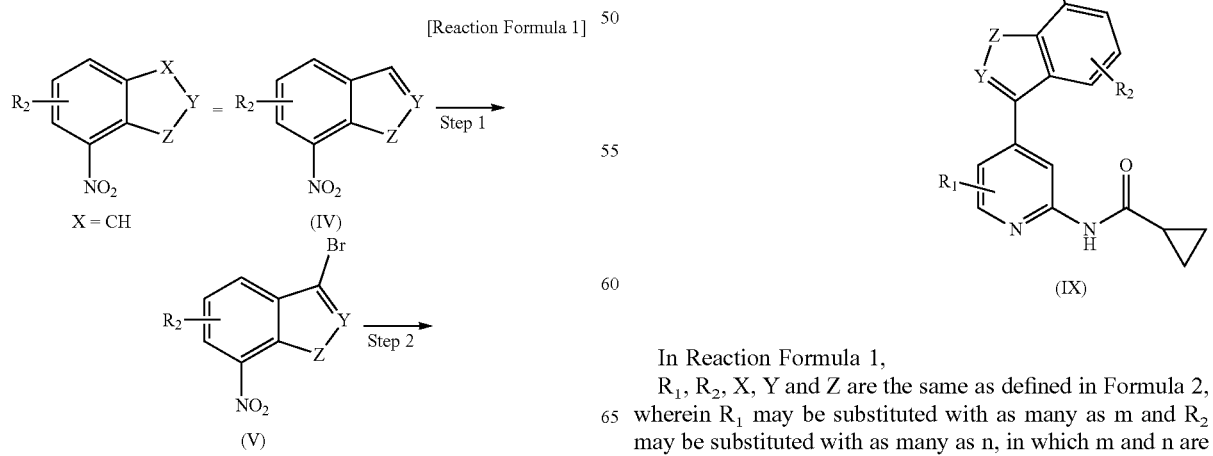

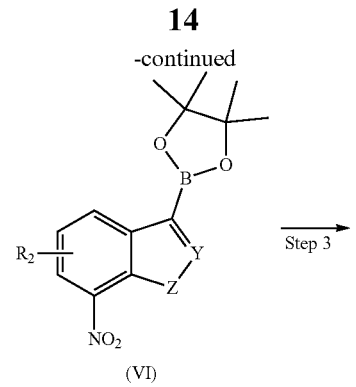

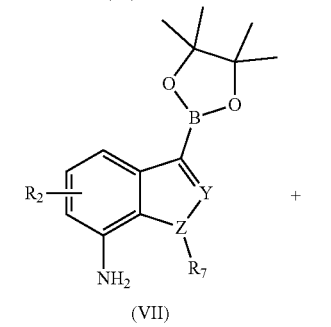

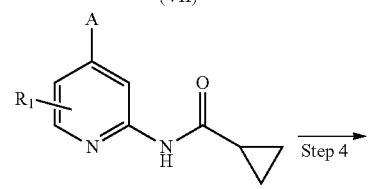

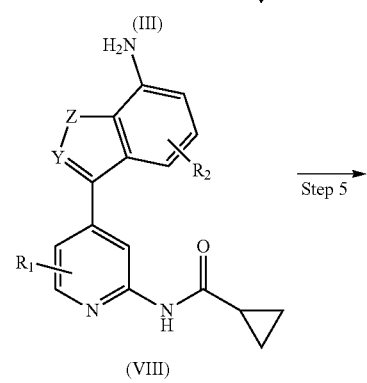

In Reaction Formula 1, $R_1$, $R_2$, X, Y and Z are the same as defined in Formula 2, wherein $R_1$ may be substituted with as many as m and $R_2$ may be substituted with as many as n, in which m and n are the same as defined in Formula 2;

A means a halogen atom including F, Cl, Br, I and the like; and

D is an analogue for incorporating $D_2$-$D_3$-$D_4$ defined in Formula 2, or the $D_2$-$D_3$-$D_4$ itself.

In Reaction Formula 1, Step 1 is preparing the compound (V) by reacting the compound (IV) with N-bromosuccinimide (NBS).

In Reaction Formula 1, Step 2 is preparing the compound (VI) from the compound (V) through bis(pinacolato)diboron.

In Reaction Formula 1, Step 3 is preparing the compound (VII) by reducing a $NO_2$ group of the compound (VI) into a $NH_2$ group.

In Reaction Formula 1, Step 4 is preparing the compound (VIII) through a Suzuki coupling reaction between the compound (VII) and the compound (III).

In Reaction Formula 1, Step 5 is preparing the compound (IX) which incorporates a derivative from the compound (VIII).

In Reaction Formula 1, the compound (III) may be synthesized through a method of the following reaction formula 1-1:

[Reaction Formula 1-1]

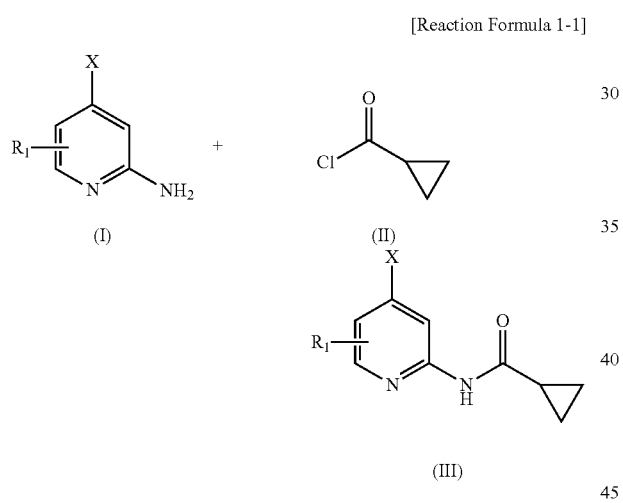

According to Reaction Formula 1-1 the compound (III) is prepared by reacting said compound (I) with the compound (II).

Synthesis may be performed through Reaction Formula 2 in addition to the method of Reaction Formula 1.

In one embodiment, a method for synthesizing the compound of Formula 2 according to the present invention may be exemplified by the following Reaction Formula 2:

[Reaction Formula 2]

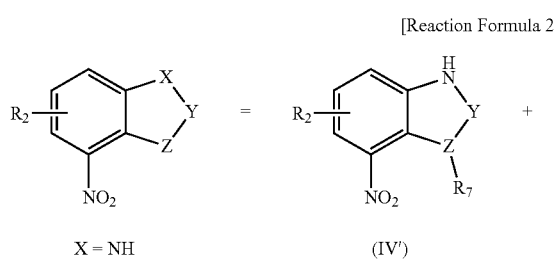

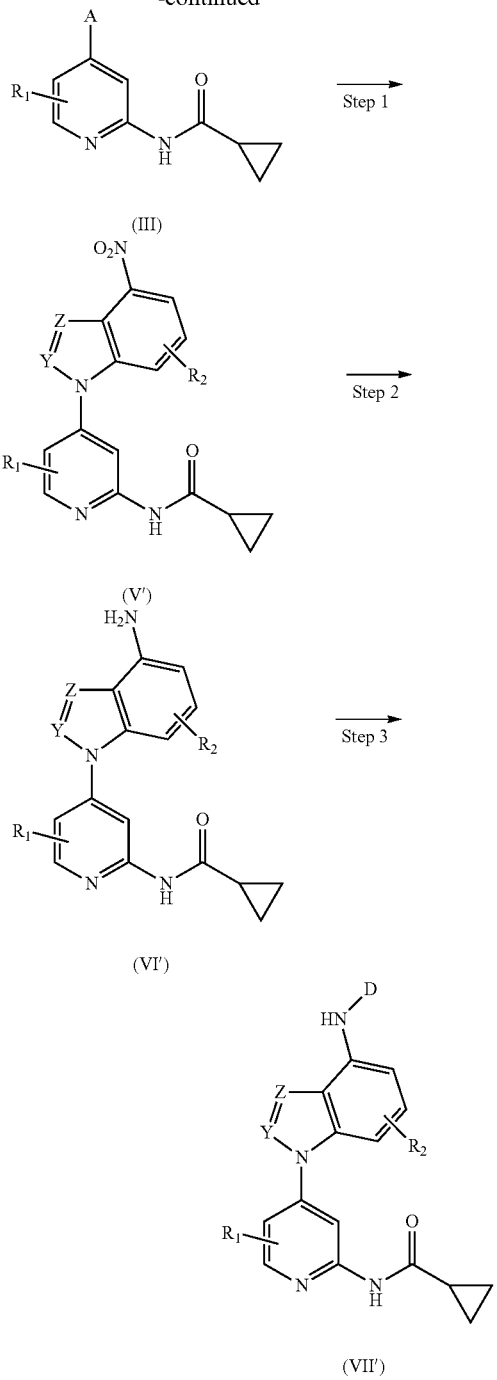

In Reaction Formula 2, $R_1$, $R_2$, X, Y and Z are the same as defined in Formula 2, wherein $R_1$ may be substituted with as many as m and $R_2$ may be substituted with as many as n, in which m and n are the same as defined in Formula 2;

A means a halogen atom including F, Cl, Br, I and the like; and

D is an analogue for incorporating $D_2$-$D_3$-$D_4$ defined in Formula 2, or the $D_2$-$D_3$-$D_4$ itself.

In Reaction Formula 2, Step 1 is preparing the compound (V') through a $S_NAr$ reaction between the compound (IV') and the compound (III).

In Reaction Formula 2, Step 2 is preparing the compound (VI') by reducing a NO$_2$ group of the compound (V') into a NH$_2$ group.

In Reaction Formula 2, Step 3 is preparing the compound (VIII') which incorporates a derivative from the compound (VII').

In Reaction Formulae 1 and 2, if the compound (IV) (in case of X═CH) is used as a starting material, it is preferable to follow Reaction Formula 1. If the compound (IV') (in case of X═NH) is used as a starting material, it is preferable to follow Reaction Formula 2.

In Reaction Formula 1, Reaction Formula 1-1 or Reaction Formula 2, the compounds (I), (II), (IV) and (IV') may be conventionally purchased or synthesized.

The compound of Formula 1 according to the present invention may be separated or purified from the products of Reaction Formulas 1 and 2 by means of various methods such as crystallization, silica gel column chromatography, etc. As such, the compound of the present invention, an initiation for preparing the same, an intermediate, etc. may be synthesized by means of various methods, and it should be interpreted that such methods are included in the scope of the present invention with regard to preparation for the compound of Formula 1.

Composition Containing Compound of Formula 1, and Use Thereof

The present invention provides a pharmaceutical composition and a use of treating or preventing protein kinase-related diseases, the composition including a compound represented by the following Formula 1, stereoisomers thereof or pharmaceutically acceptable salts thereof as an active ingredient:

[Formula 1]

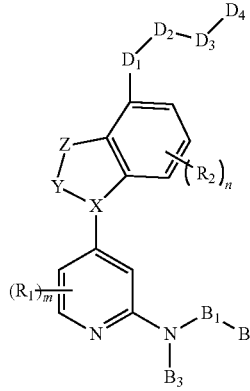

Formula 1 is the same as defined above.

As used herein, the term "prevention" means all the acts, which inhibit protein kinase-related diseases or delay the occurrence thereof by administering the pharmaceutical composition according to the present invention.

As used herein, the term "treatment" means all the acts, by which a symptom of protein kinase-related diseases gets better or takes a favorable turn by administering the pharmaceutical composition according to the present invention.

The compound of Formula 1 according to the present invention, steroisomers thereof or pharmaceutically acceptable salts thereof have a remarkable effect on preventing or treating protein kinase-related diseases by showing a protein kinase inhibitory activity.

In the present invention, the protein kinase may be janus kinase (JAK), but is not limited thereto.

In the present invention, said protein kinase-related diseases include cancers; autoimmune diseases such as psoriasis, rheumatoid arthritis, lupus, inflammatory bowel disease, chronic obstructive pulmonary disease, etc.; neurological diseases; metabolic diseases; or infections.

In the present invention, pharmaceutically acceptable salts mean the salts conventionally used in a pharmaceutical industry, for example, inorganic ion salts prepared from calcium, potassium, sodium, magnesium and the like; inorganic acid salts prepared from hydrochloric acid, nitric acid, phosphoric acid, bromic acid, iodic acid, perchloric acid, tartaric acid, sulfuric acid and the like; organic acid salts prepared from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulphonic acid salts prepared from methanesulfonic acid, ethanesulfonic acid, benzenesulfonic acid, p-toluenesulfonic acid, naphthalenesulfonic acid and the like; amino acid salts prepared from glycine, arginine, lysine, etc.; amine salts prepared from trimethylamine, triethylamine, ammonia, pyridine, picoline, etc.; and the like, but types of salts meant in the present invention are not limited to those listed salts. In the present invention, preferable salts include hydrochloric acid, trifluoroacetic acid, citric acid, bromic acid, maleic acid, phosphoric acid, sulfuric acid and tartaric acid.

For its administration, the pharmaceutical composition of the present invention may further contain at least one type of a pharmaceutically acceptable carrier, in addition to the compound represented by Formula 1, stereoisomers thereof or pharmaceutically acceptable salts thereof, and may be also used with the addition of other conventional additives such as antioxidants, buffer solutions, bacteriostatic agents, etc., if needed. Also, such pharmaceutical composition may be formulated such a way that diluents, dispersing agents, surfactants, binders and lubricants are additionally added thereto.

The composition of the present invention may be orally or parenterally administered (for example, applied intravenously, hypodermically, intraperitoneally or locally) according to an intended method, in which a dosage thereof varies in a range thereof depending on a patient's weight, age, gender, health condition and diet, an administration time, an administration method, an excretion rate, a severity of a disease and the like. A daily dosage of the compound represented by Formula 1 of the present invention is about 0.001 to 1000 mg/kg and may be administered once a day or divided into several times.

In addition to the compound represented by Formula 1, stereoisomers thereof or pharmaceutically acceptable salts thereof, said pharmaceutical composition of the present invention may further contain at least one active ingredient which shows a medicinal effect the same thereas or similar thereto.

The present invention provides a method for preventing or treating protein kinase-related diseases, including administering a therapeutically effective amount of the compound represented by Formula 1, stereoisomers thereof or pharmaceutically acceptable salts thereof into a subject.

As used herein, the "subject" means mammals including humans, and the "administration" means providing a predetermined material to a patient by means of any appropriate method.

As used herein, the term "therapeutically effective amount" refers to an amount of the compound represented by Formula 1, stereoisomers thereof or pharmaceutically acceptable salts thereof, which are effective in preventing or treating protein kinase-related diseases.

The method for preventing or treating protein kinase-related diseases according to the present invention includes not only dealing with the diseases themselves before expression of their symptoms, but also inhibiting or avoiding such symptoms by administering the compound represented by Formula 1, stereoisomers thereof or pharmaceutically acceptable salts thereof. In managing the diseases, a preventive or therapeutic dose of a certain active component may vary depending on a nature and severity of the diseases or conditions and a route of administering the active component. A dose and a frequency thereof may vary depending on an individual patient's age, weight and reactions. A suitable dose and usage may be easily selected by those skilled in the art, naturally considering such factors. Also, the method for preventing or treating protein kinase-related diseases according to the present invention may further include administering a therapeutically effective amount of an additional active agent, which is helpful in treating the diseases, along with the compound represented by Formula 1, stereoisomers thereof or pharmaceutically acceptable salts thereof, and the additional active agent may exhibit a synergy effect or an additive effect together with the compound represented by Formula 1, stereoisomers thereof or pharmaceutically acceptable salts thereof.

For preparing a medicament, the compound represented by Formula 1, stereoisomers thereof or pharmaceutically acceptable salts thereof may be combined with acceptable adjuvants, diluents, carriers, etc., and may be prepared into a complex preparation together with other active agents and thus have a synergy action of active components.

Matters mentioned in the use, composition and therapeutic method of the present invention are equally applied, if not contradictory to each other.

Advantageous Effects of Invention

A compound represented by Formula 1 according to the present invention, stereoisomers thereof or pharmaceutically acceptable salts thereof have a remarkably excellent effect on preventing or treating protein kinase-related diseases by showing a protein kinase inhibitory activity.

MODE FOR THE INVENTION

Hereinafter, the preferred Examples are provided for better understanding of the present invention. However, the following Examples are provided only for the purpose of illustrating the present invention, and thus the present invention is not limited thereto. When preparing a compound of the present invention, an order of reactions may be modified appropriately. In other words, any reaction step may be performed earlier than described herein or any substituent change may be inserted, and any reagent other than an exemplary one may be used, if necessary.

Various synthesis methods for a starting material have been known to synthesize the compound of the present invention. If said starting material is commercially available, such material may be purchased and used from its supplier. As a reagent supplier, there are companies such as Sigma-Aldrich, TCI, Wako, Kanto, Fluorchem, Acros, Alfa, Fluka, Combi-Blocks, Dae-Jung, etc., but are not limited thereto. Also, all the commercial materials were used without any additional purification, except as otherwise specified.

First of all, the compounds used for synthesis in the Examples hereinafter were prepared as shown in the following preparation example. The following Examples may be appropriately changed and modified by those skilled in the art within the scope of the present invention.

Example 1: Synthesis of N-(4-(7-(2-cyano-3-methylbut-2-enamido)-1H-indol-3-yl)pyridin-2-yl)cyclopropanec arboxamide

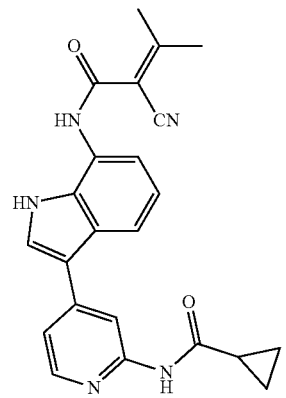 [SMILES: CC(C)=C(C#N)C(=O)Nc1cccc2c(-c3ccnc(NC(=O)C4CC4)c3)c[nH]c12]

[Step 1] Synthesis of N-(4-bromopyridin-2-yl)cyclopropanecarboxamide

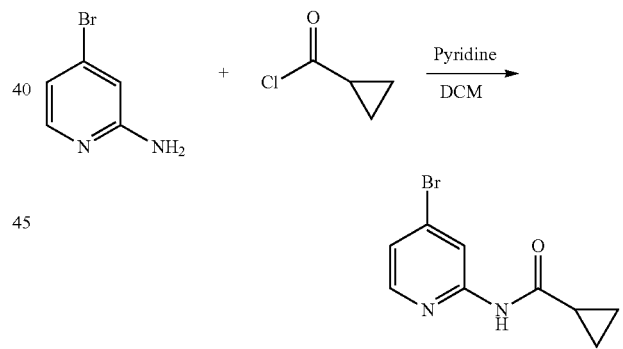

4-bromopyridine-2-amine (2.0 g, 11.56 mmol) was dissolved in dichloromethane, after which pyridine (1.8 ml) and cyclopropanecarbonyl chloride (1.2 ml, 13.87 mmol) were added dropwise thereto at 0° C., and then stirred at the same temperature for one hour. A reaction mixture was added to water (100 ml), after which a resulting solid was filtered and then dried under reduced pressure to obtain a title compound (2.1 g, 8.7 mmol).

$^1$H NMR (400 MHz, DMSO-$d_6$) δ 10.99-11.14 (m, 1H), 8.33 (d, J=1.83 Hz, 1H), 8.22 (d, J=5.31 Hz, 1H), 7.29-7.42 (m, 1H), 1.94-2.07 (m, 1H), 0.83 (d, J=6.04 Hz, 4H)

MS(ESI+) m/z 241, 243 (M+H)$^+$

[Step 2] Synthesis of 7-nitro-1-tosyl-1H-indole

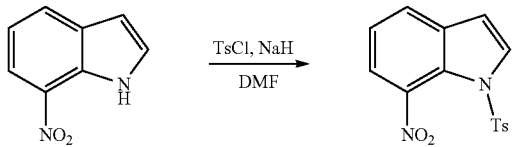

7-nitro-1H-indole (20 g, 123.3 mmol) was dissolved in dimethylformamide (1.2 L), after which sodium hydride (3.2 g, 135.6 mmol) was slowly added dropwise thereto at 0° C., such that tosylchloride (26 g, 135.6 mmol) was slowly added dropwise thereto and stirred for two hours. Dichloromethane (300 ml) was added to a resulting mixture, then washed with water (300 ml, twice), then dried with anhydrous magnesium sulfate, and then filtered, after which a resulting filtrate was distilled under reduced pressure. Ethyl ether was added to a resulting vacuum-distilled filtrate, after which a resulting solid was filtered and then dried under reduced pressure to obtain a title compound (21 g, 66.4 mmol).

$^1$H NMR (400 MHz, DMSO-$d_6$) δ 8.05 (d, J=3.66 Hz, 1H), 7.97 (d, J=7.68 Hz, 1H), 7.82 (d, J=7.87 Hz, 1H), 7.78 (d, J=8.42 Hz, 2H), 7.40-7.50 (m, 3H), 7.08 (d, J=3.66 Hz, 1H), 2.37 (s, 3H)

MS(ESI+) m/z 317 (M+H)$^+$

[Step 3] Synthesis of 3-bromo-7-nitro-1-tosyl-1H-indole

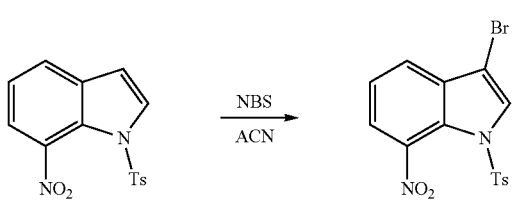

7-nitro-1-tosyl-1H-indole (21 g, 66.4 mmol) was dissolved in acetonitrile (664 ml), after which N-bromosuccinimide (24 g, 132.78 mmol) was added thereto, and then heated to 50° C. for 18 hours. A resulting mixture was cooled down to room temperature, after which a resulting solid was filtered and then dried under reduced pressure to obtain a title compound (24.9 g, 63 mmol).

$^1$H NMR (400 MHz, DMSO-$d_6$) δ 8.44-8.51 (m, 1H), 7.94-8.00 (m, 1H), 7.84-7.90 (m, 3H), 7.57-7.64 (m, 1H), 7.45-7.52 (m, 2H), 2.40 (s, 3H)

MS(ESI+) m/z 395, 397 (M+H)$^+$

[Step 4] Synthesis of 7-nitro-3-(4,4,5,5-tetramethyl-1,3,2-dioxaborolan-2-yl)-1-tosyl-1H-indole

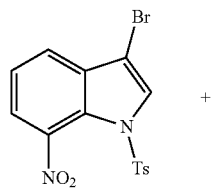
+
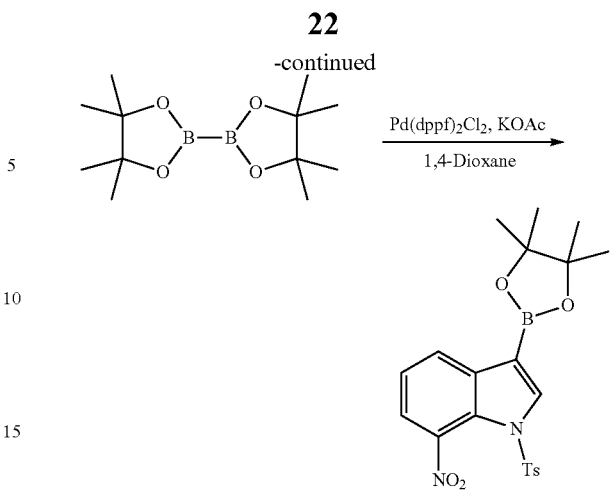

3-bromo-7-nitro-1-tosyl-1H-indole (24.9 g, 63 mmol), dipinacolborane (32 g, 126 mmol), [1,1'-bis(diphenylphosphino)ferrocene]dichloropalladium (5.2 g, 6.4 mmol), potassium acetate (12 g, 122.2 mmol) were added to dioxane (630 ml), and then heated to 100° C. for two hours. A resulting mixture was cooled down to room temperature, and then distilled under reduced pressure, after which dichloromethane (300 ml) was added thereto, and then washed with distilled water (300 ml, twice). A separated organic layer was dried with anhydrous magnesium sulfate, and then filtered, after which a resulting filtrate was distilled under reduced pressure. Separation was performed with column chromatography to obtain a title compound (16.9 g, 38.2 mmol).

$^1$H NMR (400 MHz, DMSO-$d_6$) δ 8.33 (s, 1H), 8.16-8.21 (m, 1H), 7.95-8.01 (m, 2H), 7.84-7.90 (m, 1H), 7.47-7.57 (m, 3H), 2.42 (s, 3H), 1.34 (s, 12H)

MS(ESI+) m/z 443 (M+H)$^+$

[Step 5] Synthesis of 3-(4,4,5,5-tetramethyl-1,3,2-dioxaborolan-2-yl)-1-tosyl-1H-indol-7-amine

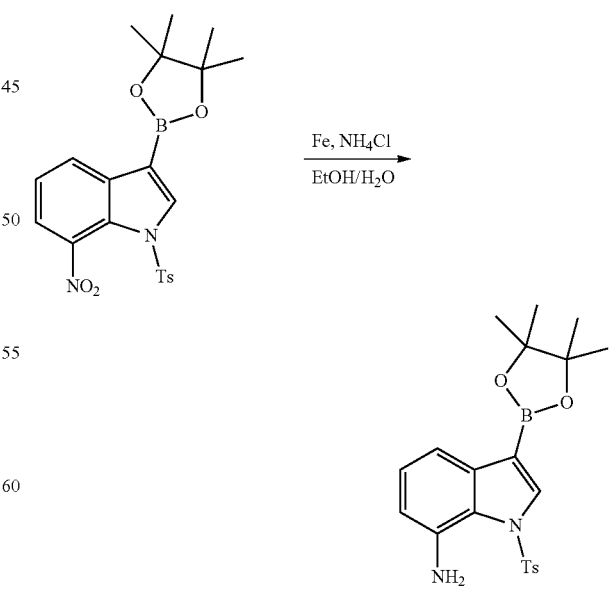

7-nitro-3-(4,4,5,5-tetramethyl-1,3,2-dioxaborolane-2-yl)-1-tosyl-1H-indole (16.9 g, 38.2 mmol) was dissolved in ethanol/distilled water (2/1, 330 ml), after which iron (6.4 g, 114.6 mmol) and ammonium chloride (20 g, 382 mmol) were added thereto, and then heated to 80° C. for three hours. A resulting mixture was cooled down to room temperature, after which methanol was added thereto, and then filtered to remove iron therefrom. A resulting filtrate was distilled under reduced pressure, and then separated with column chromatography to obtain a title compound (7.4 g, 17.9 mmol).

$^1$H NMR (400 MHz, DMSO-$d_6$) δ 7.80-7.83 (m, 1H), 7.75-7.80 (m, 2H), 7.59-7.62 (m, 1H), 7.37-7.43 (m, 2H), 7.32-7.36 (m, 1H), 7.03-7.09 (m, 1H), 2.31-2.34 (m, 3H), 2.28-2.30 (m, 1H) 1.30 (s, 12H) 1.14-1.19 (m, 4H)

MS(ESI+) m/z 413 (M+H)$^+$

[Step 6] Synthesis of N-(4-(7-amino-1-tosyl-1H-indol-3-yl)pyridin-2-yl)cyclopropanecarboxamide

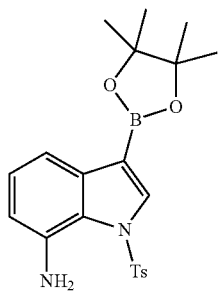

+

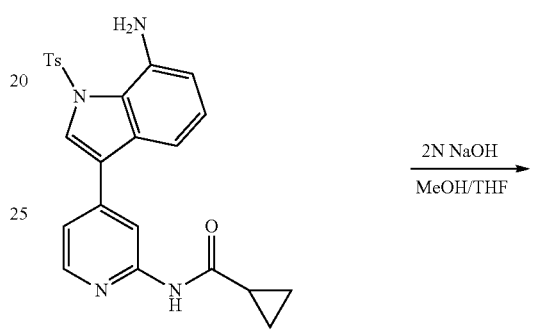

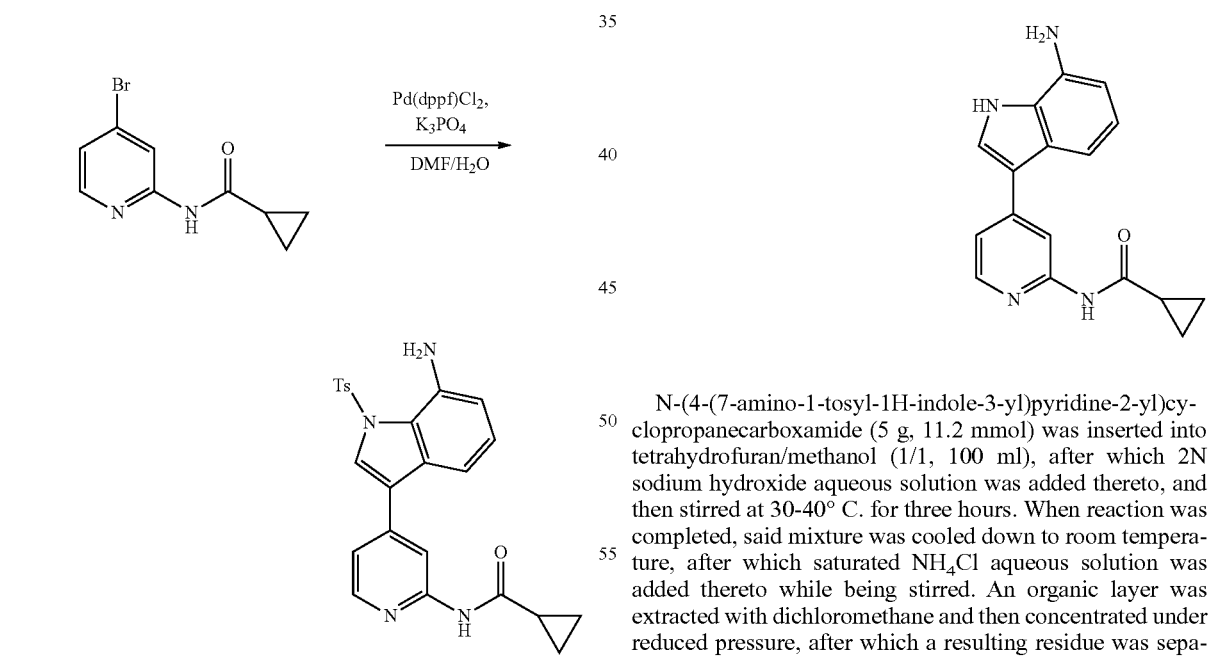

3-(4,4,5,5-tetramethyl-1,3,2-dioxaborolane-2-yl)-1-tosyl-1H-indole-7-amine (7.4 g, 17.9 mmol) was dissolved in a solution of dimethylformamide/distilled water (2:1), after which N-(4-bromopyridine-2-yl)cyclopropanecarboxamide (5.1 g, 21.48 mmol) obtained from Preparation Example 1, [1,1'-bis(diphenylphosphino)ferrocene]dichloropalladium (2.2 g, 2.68 mmol) and potassium phosphate (4.7 g, 21.48 mmol) were added thereto, and then stirred at 100° C. for one hour. When reaction was completed, said mixture was cooled down to room temperature, after which water was added thereto, such that extraction was performed with ethylacetate. An extracted solution was dried with anhydrous magnesium sulfate, and then concentrated under reduced pressure to obtain a resulting reside. The residue was separated with column chromatography to obtain a title compound (5 g, 11.2 mmol).

MS(ESI+) m/z 447 (M+H)$^+$

[Step 7] Synthesis of N-(4-(7-amino-1H-indol-3-yl)pyridin-2-yl)cyclopropanecarboxamide N-(4-(7-amino-1-tosyl-1H-indole-3-yl)pyridine-2-yl)cyclopropanecarboxamide (5 g, 11.2 mmol) was inserted into tetrahydrofuran/methanol (1/1, 100 ml), after which 2N sodium hydroxide aqueous solution was added thereto, and then stirred at 30-40° C. for three hours. When reaction was completed, said mixture was cooled down to room temperature, after which saturated NH$_4$Cl aqueous solution was added thereto while being stirred. An organic layer was extracted with dichloromethane and then concentrated under reduced pressure, after which a resulting residue was separated with column chromatography to obtain a title compound (2.7 g, 9.2 mmol).

$^1$H NMR (DMSO-$d_6$, 400 MHz) δ 11.24 (br s, 1H), 10.71 (s, 1H), 8.53 (s, 1H), 8.22 (d, 1H, J=5.3 Hz), 7.90 (d, 1H, J=2.7 Hz), 7.37 (dd, 1H, J=1.3, 5.3 Hz), 7.22 (d, 1H, J=8.1 Hz), 6.88 (t, 1H, J=7.8 Hz), 6.42 (d, 1H, J=7.5 Hz), 1.9-2.1 (m, 1H), 0.8-0.9 (m, 4H)

MS(ESI+) m/z 293 (M+H)$^+$

[Step 8] Synthesis of N-(4-(7-(2-cyano-3-methyl-but-2-enamido)-1H-indol-3-yl)pyridin-2-yl)cyclo-propanecarb oxamide

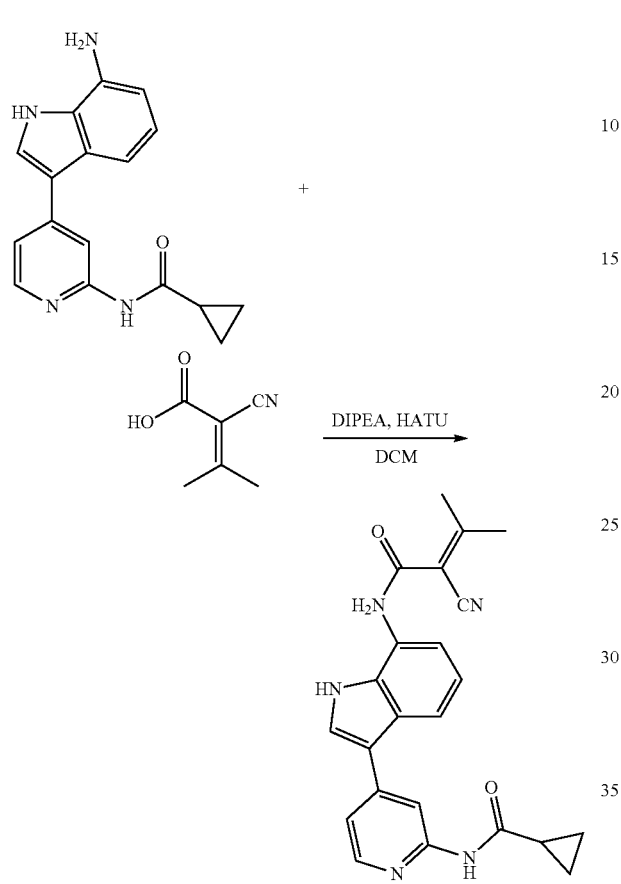

1.5 equivalents of 2-cyano-3-methylbut-2-enoic acid, 1.5 equivalents of HATU, 2 equivalents of DIPEA and synthesized N-(4-(7-amino-1H-indole-3-yl)pyridine-2-yl)cyclopropanecarboxamide (100 mg) were inserted into dichloromethane solution, and then stirred at room temperature. After reaction was completed, H₂O was added to said mixture, after which extraction was performed with dichloromethane to separate an organic layer therefrom. After the mixture was concentrated, a resulting concentrate was separated with column chromatography to obtain a product, i.e., N-(4-(7-(2-cyano-3-methylbut-2-enamido)-1H-indole-3-yl)pyridine-2-yl)cyclopropanecarboxamide.

$^1$H NMR (DMSO-$d_6$, 400 MHz) δ 10.79 (br s, 1H), 10.34 (br d, 1H, J=0.9 Hz), 8.55 (br s, 1H), 8.27 (s, 1H), 7.98 (br s, 1H), 7.42 (br d, 1H, J=4.8 Hz), 7.37 (br s, 1H), 7.1-7.2 (m, 1H), 2.24 (br s, 3H), 2.18 (br s, 3H), 2.0-2.0 (m, 1H), 0.8-0.9 (m, 4H)

MS(ESI+) m/z 400 (M+H)$^+$

Examples 2 to 41

Hereinafter, the compounds in Examples 2 to 41 were prepared by means of the same method as shown in Example 1, but did with an appropriate reactant, considering the reaction formula 1 and a structure of the compound to be prepared.

Examples 2: Synthesis of N-(3-(2-(cyclopropanecarboxamido)pyridin-4-yl)-1H-indol-7-yl)-3,5-difluorobenzamide

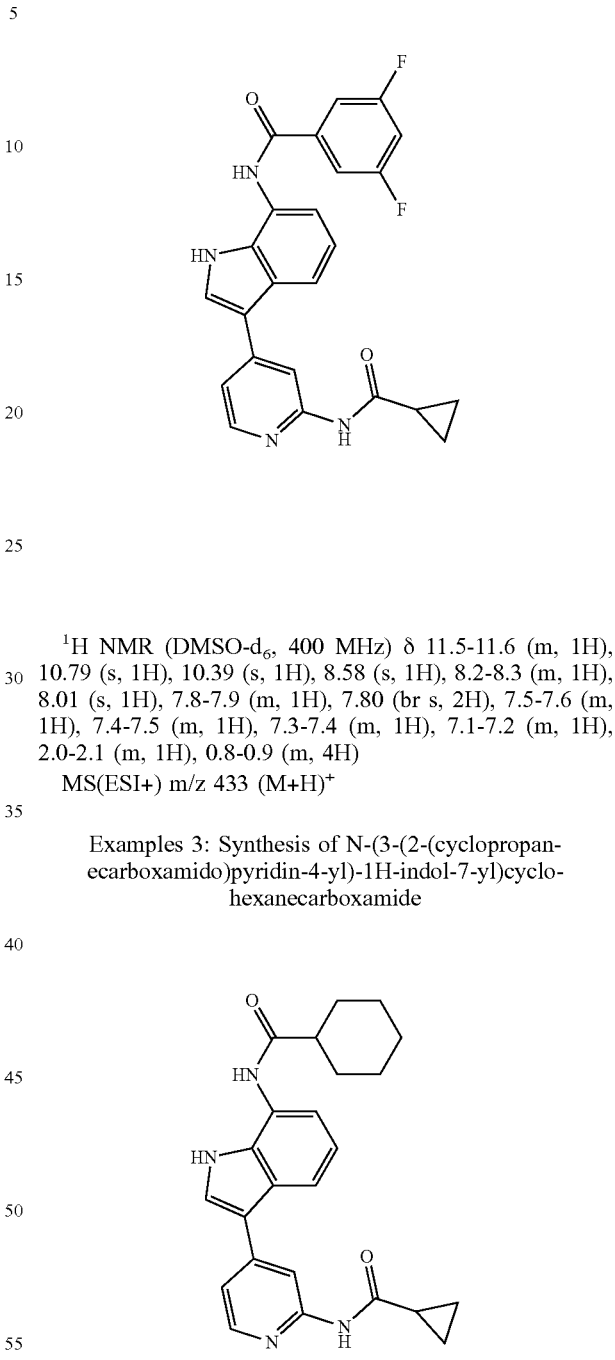

$^1$H NMR (DMSO-$d_6$, 400 MHz) δ 11.5-11.6 (m, 1H), 10.79 (s, 1H), 10.39 (s, 1H), 8.58 (s, 1H), 8.2-8.3 (m, 1H), 8.01 (s, 1H), 7.8-7.9 (m, 1H), 7.80 (br s, 2H), 7.5-7.6 (m, 1H), 7.4-7.5 (m, 1H), 7.3-7.4 (m, 1H), 7.1-7.2 (m, 1H), 2.0-2.1 (m, 1H), 0.8-0.9 (m, 4H)

MS(ESI+) m/z 433 (M+H)$^+$

Examples 3: Synthesis of N-(3-(2-(cyclopropanecarboxamido)pyridin-4-yl)-1H-indol-7-yl)cyclohexanecarboxamide $^1$H NMR (DMSO-$d_6$, 400 MHz) δ 11.04 (s, 1H), 8.5-8.6 (m, 1H), 8.5-8.5 (m, 1H), 8.4-8.5 (m, 1H), 8.1-8.2 (m, 1H), 7.5-7.6 (m, 1H), 7.4-7.5 (m, 1H), 6.9-7.0 (m, 1H), 2.0-2.1 (m, 1H), 1.2-1.3 (m, 8H), 1.1-1.2 (m, 2H), 0.8-0.9 (m, 4H)

MS(ESI+) m/z 403 (M+H)$^+$

Examples 4: Synthesis of N-(3-(2-(cyclopropanecarboxamido)pyridin-4-yl)-1H-indol-7-yl)-2-fluoroisonicotinamide

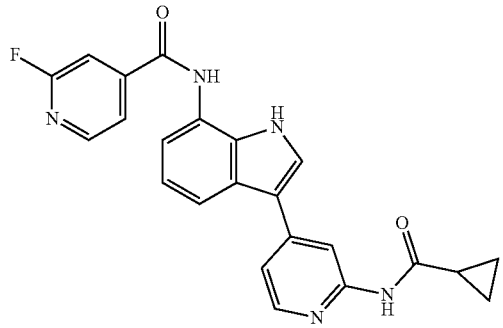 [SMILES: O=C(Nc1cccc2c(-c3ccnc(NC(=O)C4CC4)c3)c[nH]c12)c1ccnc(F)c1]

¹H NMR (DMSO-d₆, 400 MHz) δ 11.5-11.6 (m, 1H), 10.8-10.8 (m, 1H), 10.5-10.6 (m, 1H), 8.5-8.6 (m, 1H), 8.5-8.5 (m, 1H), 8.2-8.3 (m, 1H), 8.0-8.1 (m, 1H), 7.9-8.0 (m, 1H), 7.9-7.9 (m, 1H), 7.8-7.8 (m, 1H), 7.44 (br d, 1H, J=1.5 Hz), 7.36 (br s, 1H), 7.21 (br s, 1H), 2.0-2.1 (m, 1H), 0.8-0.9 (m, 4H)

MS(ESI+) m/z 416 (M+H)⁺

Examples 5: Synthesis of N-(3-(2-(cyclopropanecarboxamido)pyridin-4-yl)-1H-indol-7-yl)-3,5-dimethylbenzamid

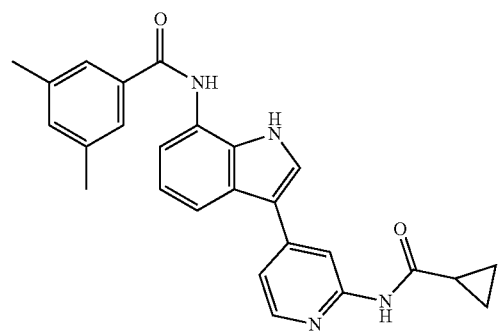 [SMILES: Cc1cc(C)cc(C(=O)Nc2cccc3c(-c4ccnc(NC(=O)C5CC5)c4)c[nH]c23)c1]

¹H NMR (DMSO-d₆, 400 MHz) δ 11.0-11.1 (m, 1H), 8.5-8.6 (m, 1H), 8.5-8.5 (m, 1H), 8.5-8.5 (m, 1H), 8.1-8.2 (m, 1H), 7.5-7.6 (m, 1H), 7.4-7.5 (m, 1H), 6.94 (d, 1H, J=4.0 Hz), 2.0-2.1 (m, 1H), 1.06 (s, 10H), 0.85 (br s, 4H), 0.7-0.7 (m, 1H)

MS(ESI+) m/z 425 (M+H)⁺

Examples 6: Synthesis of N-(3-(2-(cyclopropanecarboxamido)pyridin-4-yl)-1H-indol-7-yl)thiazole-5-carboxamide

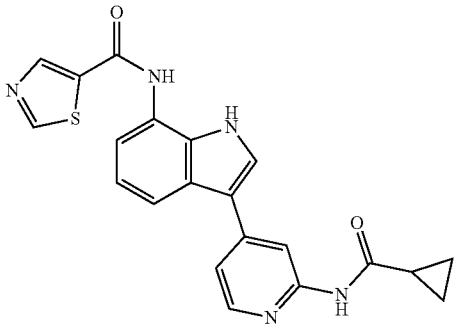 [SMILES: O=C(Nc1cccc2c(-c3ccnc(NC(=O)C4CC4)c3)c[nH]c12)c1cncs1]

¹H NMR (DMSO-d₆, 400 MHz) δ 11.48 (br s, 1H), 10.79 (s, 1H), 10.15 (s, 1H), 8.58 (s, 1H), 8.4-8.5 (m, 1H), 8.27 (d, 1H, J=5.5 Hz), 7.96 (d, 1H, J=2.7 Hz), 7.82 (d, 1H, J=7.7 Hz), 7.67 (s, 2H), 7.3-7.5 (m, 2H), 7.25 (s, 1H), 7.17 (t, 1H, J=7.9 Hz), 2.33 (m, 1H), 0.6-0.9 (m, 4H)

MS(ESI+) m/z 404 (M+H)⁺

Examples 7: Synthesis of N-(4-(7-butyramido-1H-indol-3-yl)pyridin-2-yl)cyclopropanecarboxamide ¹H NMR (DMSO-d₆, 400 MHz) δ 11.2-11.3 (m, 1H), 10.6-10.8 (m, 1H), 9.6-9.8 (m, 1H), 8.5-8.6 (m, 1H), 8.2-8.3 (m, 1H), 7.9-8.0 (m, 1H), 7.7-7.8 (m, 1H), 7.4-7.5 (m, 1H), 7.4-7.4 (m, 1H), 7.1-7.2 (m, 1H), 2.4-2.4 (m, 2H), 2.0-2.1 (m, 1H), 1.6-1.8 (m, 2H), 0.97 (s, 3H), 0.8-0.9 (m, 4H)

MS(ESI+) m/z 363 (M+H)⁺

Examples 8: Synthesis of N-(4-(7-(2-cyanoacetamido)-1H-indol-3-yl)-5-methylpyridin-2-yl)cyclopropanecarboxamide

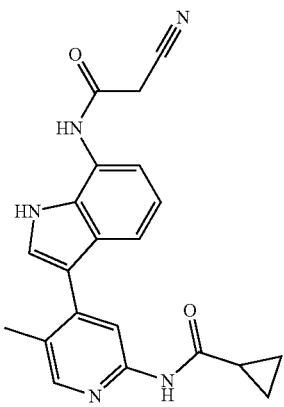 [SMILES: Cc1cnc(NC(=O)C2CC2)cc1-c1c[nH]c2c(NC(=O)CC#N)cccc12]

¹H NMR (400 MHz, CHLOROFORM-d) δ 11.29-11.40 (m, 1H), 10.71-10.80 (m, 1H), 10.08-10.24 (m, 1H), 8.33-8.43 (m, 1H), 7.94-8.02 (m, 1H), 7.77-7.86 (m, 1H), 7.24-7.34 (m, 2H), 7.09-7.17 (m, 1H), 3.92-4.03 (m, 2H), 2.42-2.47 (m, 3H), 2.00-2.10 (m, 1H), 0.77-0.88 (m, 4H)

MS(ESI+) m/z 374 (M+H)⁺

Examples 9: Synthesis of N-(4-(7-(2-cyano-3-methylbut-2-enamido)-1H-indol-3-yl)-6-methylpyridin-2-yl)cyclopropanecarboxamide

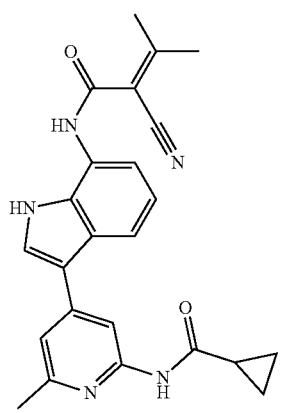 [SMILES: CC(C)=C(C#N)C(=O)Nc1cccc2c(-c3cc(C)nc(NC(=O)C4CC4)c3)c[nH]c12]

¹H NMR (400 MHz, CHLOROFORM-d) δ 11.14-11.30 (m, 1H), 10.71 (s, 1H), 10.34 (s, 1H), 8.23 (s, 2H), 7.63-7.76 (m, 1H), 7.45-7.55 (m, 1H), 7.32-7.41 (m, 1H), 7.03-7.15 (m, 1H), 2.68 (s, 6H), 2.28-2.34 (m, 3H), 2.14-2.27 (m, 6H), 1.95-2.06 (m, 1H), 0.75-0.87 (m, 4H)

MS(ESI+) m/z 414 (M+H)⁺

Examples 10: Synthesis of N-(4-(7-(2-cyanoacetamido)-1H-indol-3-yl)pyridin-2-yl)cyclopropanecarboxamide

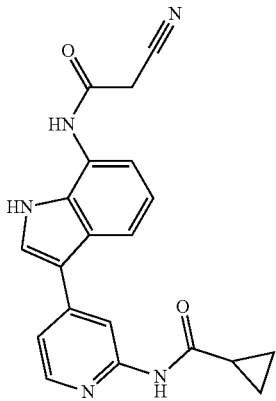 [SMILES: N#CCC(=O)Nc1cccc2c(-c3ccnc(NC(=O)C4CC4)c3)c[nH]c12]

¹H NMR (DMSO-d₆, 400 MHz) δ 11.37 (br s, 1H), 10.7-10.8 (m, 1H), 10.1-10.2 (m, 1H), 8.5-8.6 (m, 1H), 8.2-8.3 (m, 1H), 8.0-8.0 (m, 1H), 7.8-7.9 (m, 1H), 7.4-7.5 (m, 1H), 7.3-7.3 (m, 1H), 7.2-7.3 (m, 1H), 7.1-7.2 (m, 1H), 3.98 (br s, 2H), 2.0-2.1 (m, 1H), 0.8-0.9 (m, 4H)

MS(ESI+) m/z 360 (M+H)⁺

Examples 11: Synthesis of 4-cyano-N-(3-(2-(cyclopropanecarboxamido)pyridin-4-yl)-1H-indol-7-yl)tetrahydro-2H-pyran-4-carboxamide

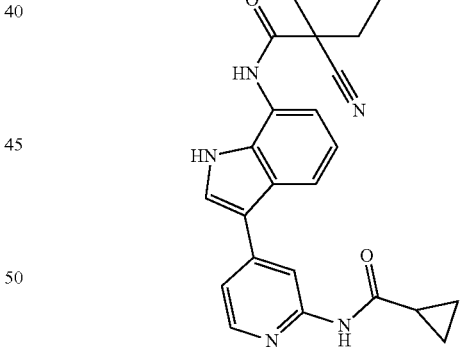

¹H NMR (DMSO-d₆, 400 MHz) δ 11.3-11.4 (m, 1H), 11.3-11.3 (m, 1H), 10.8-10.8 (m, 1H), 10.1-10.2 (m, 1H), 8.5-8.6 (m, 1H), 8.2-8.3 (m, 1H), 8.0-8.0 (m, 1H), 7.8-7.9 (m, 1H), 7.4-7.5 (m, 1H), 7.17 (br d, 2H, J=3.1 Hz), 4.0-4.1 (m, 2H), 3.5-3.6 (m, 2H), 2.2-2.3 (m, 4H), 1.9-2.1 (m, 1H), 0.8-0.9 (m, 4H)

MS(ESI+) m/z 430 (M+H)⁺

Examples 12: Synthesis of N-(4-(7-(2-cyano-3-methylbut-2-enamido)-1H-indol-3-yl)-5-methylpyridin-2-yl)cyclopropanecarboxamide

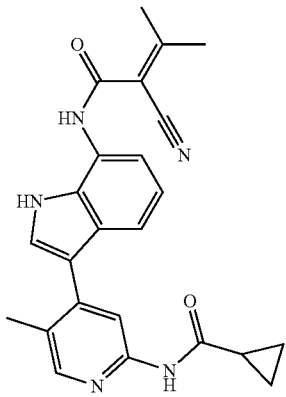 [SMILES: CC(C)=C(C#N)C(=O)Nc1cccc2c(-c3cc(NC(=O)C4CC4)ncc3C)c[nH]c12]

MS(ESI+) m/z 414 (M+H)$^+$

Examples 13: Synthesis of N-(4-(7-(2-(1-cyanocyclopropyl)acetamido)-1H-indol-3-yl)pyridin-2-yl)cyclopropanecarboxamide

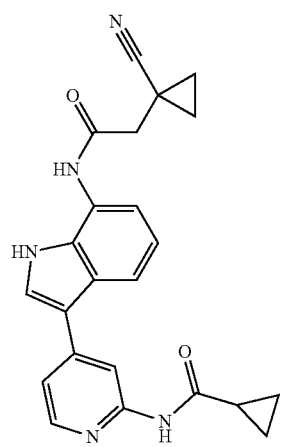 [SMILES: N#CC1(CC(=O)Nc2cccc3c(-c4ccnc(NC(=O)C5CC5)c4)c[nH]c23)CC1]

$^1$H NMR (DMSO-d$_6$, 400 MHz) δ 11.41 (br s, 1H), 10.79 (s, 1H), 9.92 (s, 1H), 8.55 (s, 1H), 8.27 (d, 1H, J=5.3 Hz), 8.01 (d, 1H, J=2.7 Hz), 7.76 (d, 1H, J=7.9 Hz), 7.54 (d, 1H, J=7.5 Hz), 7.41 (d, 1H, J=5.4 Hz), 7.14 (t, 1H, J=7.8 Hz), 2.72 (s, 2H), 2.0-2.1 (m, 1H), 1.2-1.2 (m, 4H), 0.8-0.9 (m, 4H)

MS(ESI+) m/z 400 (M+H)$^+$

Examples 14: Synthesis of N-(4-(7-(2-cyanopropanamido)-1H-indol-3-yl)pyridin-2-yl)cyclopropanecarboxamide

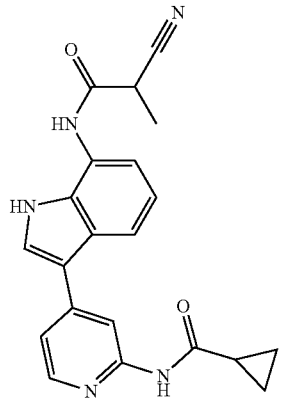 [SMILES: CC(C#N)C(=O)Nc1cccc2c(-c3ccnc(NC(=O)C4CC4)c3)c[nH]c12]

$^1$H NMR (DMSO-d$_6$, 400 MHz) δ 10.80 (s, 1H), 10.23 (s, 1H), 8.55 (s, 1H), 8.27 (d, 1H, J=5.3 Hz), 8.02 (d, 1H, J=2.9 Hz), 7.82 (d, 1H, J=8.1 Hz), 7.43 (d, 1H, J=5.4 Hz), 7.34 (d, 1H, J=7.5 Hz), 7.1-7.2 (m, 1H), 1.99 (br d, 1H, J=7.3 Hz), 1.62 (d, 3H, J=7.3 Hz), 0.8-0.9 (m, 4H)

MS(ESI+) m/z 374 (M+H)$^+$

Examples 15: Synthesis of N-(4-(7-(2-cyano-3-methylbut-2-enamido)-5-methyl-1H-indol-3-yl)pyridin-2-yl)cyclo propanecarboxamide

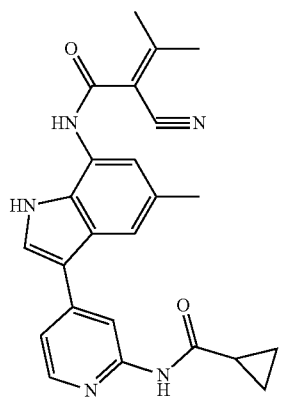 [SMILES: CC(C)=C(C#N)C(=O)Nc1cc(C)cc2c(-c3ccnc(NC(=O)C4CC4)c3)c[nH]c12]

$^1$H NMR (DMSO-d$_6$, 400 MHz) δ 11.20 (br s, 1H), 10.76 (s, 1H), 10.28 (br s, 1H), 8.48 (br s, 1H), 8.27 (br d, 1H, J=5.7 Hz), 7.89 (br s, 1H), 7.61 (br s, 1H), 7.4-7.5 (m, 1H), 7.26 (br s, 1H), 2.42 (br s, 3H), 2.23 (br s, 2H), 2.1-2.2 (m, 2H), 0.8-0.9 (m, 4H)

MS(ESI+) m/z 414 (M+H)$^+$

Examples 16: Synthesis of N-(3-(2-(cyclopropanecarboxamido)pyridin-4-yl)-5-methyl-1H-indol-7-yl)-5-methylpyrazine-2-carboxamide

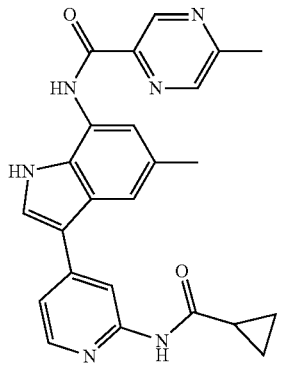 [SMILES: Cc1cc(NC(=O)c2cnc(C)cn2)c2[nH]cc(-c3ccnc(NC(=O)C4CC4)c3)c2c1]

$^1$H NMR (DMSO-d$_6$, 400 MHz) δ 11.50 (br s, 1H), 10.76 (br s, 1H), 10.63 (br s, 1H), 9.19 (br s, 1H), 8.75 (br s, 1H), 8.50 (br s, 1H), 8.27 (br d, 1H, J=5.3 Hz), 7.88 (br s, 1H), 7.65 (br s, 1H), 7.43 (br d, 1H, J=4.8 Hz), 7.32 (br s, 1H), 2.5-2.7 (m, 4H), 2.4-2.5 (m, 6H), 2.05 (br s, 1H), 0.7-0.9 (m, 4H)

MS(ESI+) m/z 427 (M+H)$^+$

Examples 17: Synthesis of N-(4-(7-(2,3-dimethylbut-2-enamido)-1H-indol-3-yl)pyridin-2-yl)cyclopropanecarboxamide

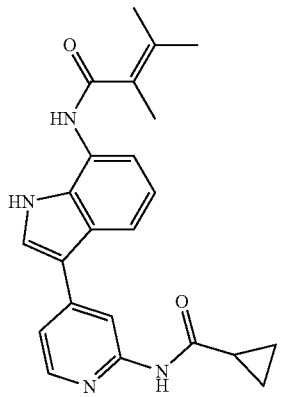 [SMILES: CC(C)=C(C)C(=O)Nc1cccc2c(-c3ccnc(NC(=O)C4CC4)c3)c[nH]c12]

$^1$H NMR (DMSO-d$_6$, 400 MHz) δ 11.3-11.3 (m, 1H), 10.78 (s, 1H), 9.7-9.7 (m, 1H), 8.5-8.6 (m, 1H), 8.2-8.3 (m, 1H), 7.9-8.0 (m, 1H), 7.7-7.8 (m, 1H), 7.6-7.7 (m, 1H), 7.4-7.4 (m, 1H), 7.1-7.2 (m, 1H), 2.0-2.1 (m, 1H), 1.91 (s, 3H), 1.82 (s, 3H), 1.76 (s, 3H), 0.8-0.9 (m, 4H)

MS(ESI+) m/z 389 (M+H)$^+$

Examples 18: Synthesis of N-(4-(7-(2-(4-methylpiperazin-1-yl)propanamido)-1H-indol-3-yl)pyridin-2-yl)cyclopropanecarboxamide

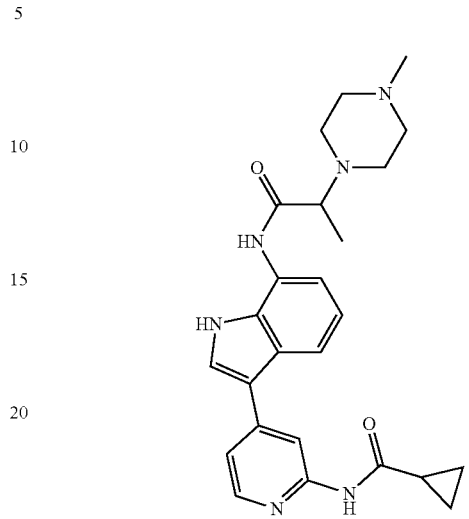

$^1$H NMR (DMSO-d$_6$, 400 MHz) δ 11.4-11.4 (m, 1H), 10.78 (s, 1H), 9.7-9.8 (m, 1H), 8.5-8.6 (m, 1H), 8.2-8.3 (m, 1H), 8.0-8.0 (m, 1H), 7.7-7.8 (m, 1H), 7.5-7.5 (m, 1H), 7.4-7.4 (m, 1H), 7.1-7.2 (m, 1H), 2.1-2.1 (m, 1H), 2.69 (s, 3H), 2.4-2.4 (m, 3H), 2.3-2.3 (m, 1H), 2.0-2.1 (m, 1H), 1.2-1.3 (m, 8H), 0.8-0.9 (m, 4H)

MS(ESI+) m/z 447 (M+H)$^+$

Examples 19: Synthesis of N-(4-(7-(2-cyano-3-methylbut-2-enamido)-1H-indol-3-yl)-6-methoxypyridin-2-yl)cyclopropanecarboxamide

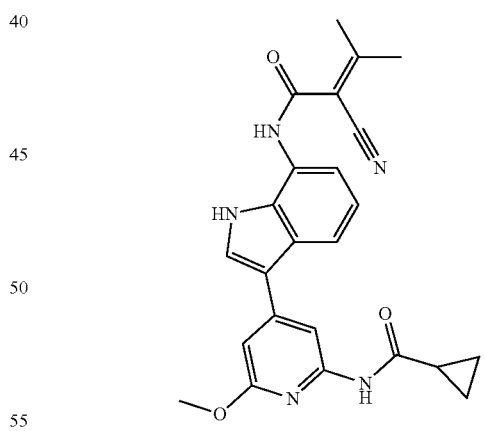

$^1$H NMR (400 MHz, DMSO-d$_6$) δ 11.12-11.27 (m, 1H), 10.52-10.71 (m, 1H), 10.29 (s, 1H), 8.47-8.61 (m, 1H), 8.09-8.19 (m, 1H), 7.44-7.54 (m, 1H), 7.30-7.39 (m, 1H), 7.08-7.18 (m, 2H), 3.86-3.90 (m, 3H), 2.23-2.26 (m, 3H), 2.17-2.20 (m, 3H), 2.10-2.15 (m, 1H), 0.83-0.87 (m, 4H)

MS(ESI+) m/z 430 (M+H)$^+$

Examples 20: Synthesis of N-(4-(7-(2-cyanoacetamido)-1H-indol-3-yl)-6-methoxypyridin-2-yl)cyclopropanecarboxamide

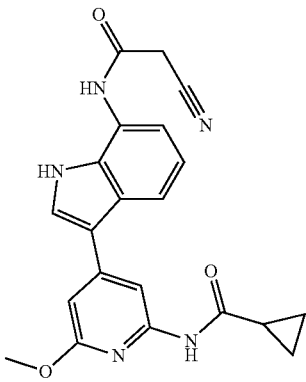 [SMILES: COc1cc(-c2c[nH]c3c(NC(=O)CC#N)cccc23)cc(NC(=O)C2CC2)n1]

¹H NMR (400 MHz, DMSO-d₆) δ 11.11-11.26 (m, 1H), 10.50-10.63 (m, 1H), 10.05-10.12 (m, 1H), 8.51-8.59 (m, 1H), 8.12-8.20 (m, 1H), 7.48-7.57 (m, 1H), 7.19-7.28 (m, 1H), 7.05-7.16 (m, 2H), 3.97 (s, 2H), 3.86 (s, 3H), 2.09-2.19 (m, 1H), 0.79-0.90 (m, 4H)

MS(ESI+) m/z 390 (M+H)⁺

Examples 21: Synthesis of N-(3-(2-(cyclopropanecarboxamido)pyridin-4-yl)-1H-indol-7-yl)-4-(trifluoromethyl)thiazole-2-carboxamide

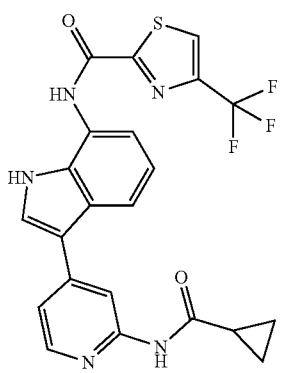 [SMILES: O=C(Nc1cccc2c(-c3ccnc(NC(=O)C4CC4)c3)c[nH]c12)c1nc(C(F)(F)F)cs1]

¹H NMR (DMSO-d₆, 400 MHz) δ 11.5-11.6 (m, 1H), 10.99 (s, 1H), 10.8-10.9 (m, 1H), 8.8-8.9 (m, 1H), 8.5-8.6 (m, 1H), 8.2-8.3 (m, 1H), 7.9-8.1 (m, 1H), 7.9-7.9 (m, 1H), 7.4-7.5 (m, 1H), 7.2-7.3 (m, 1H), 7.1-7.2 (m, 1H), 2.0-2.1 (m, 1H), 0.8-0.9 (m, 4H)

MS(ESI+) m/z 472 (M+H)⁺

Examples 22: Synthesis of (E)-N-(4-(7-(2-cyano-3-phenylacrylamido)-1H-indol-3-yl)pyridin-2-yl)cyclopropanecarboxamide

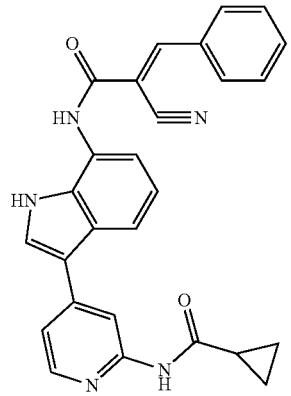 [SMILES: N#C/C(=C\c1ccccc1)C(=O)Nc1cccc2c(-c3ccnc(NC(=O)C4CC4)c3)c[nH]c12]

¹H NMR (DMSO-d₆, 400 MHz) δ 11.5-11.6 (m, 1H), 10.7-10.8 (m, 1H), 10.4-10.5 (m, 1H), 8.5-8.6 (m, 1H), 8.2-8.3 (m, 4H), 8.0-8.1 (m, 2H), 8.00 (br s, 1H), 7.86 (br dd, 1H, J=3.7, 8.2 Hz), 7.4-7.5 (m, 1H), 7.3-7.4 (m, 1H), 7.1-7.2 (m, 1H), 3.5-3.7 (m, 1H), 3.0-3.2 (m, 3H), 2.0-2.1 (m, 1H), 0.8-0.9 (m, 4H)

MS(ESI+) m/z 448 (M+H)⁺

Examples 23: Synthesis of N-(3-(2-(cyclopropanecarboxamido)pyridin-4-yl)-1H-indol-7-yl)-1H-pyrrole-2-carboxamide

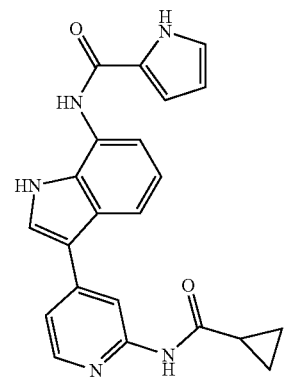 [SMILES: O=C(Nc1cccc2c(-c3ccnc(NC(=O)C4CC4)c3)c[nH]c12)c1ccc[nH]1]

¹H NMR (DMSO-d₆, 400 MHz) δ 11.7-11.8 (m, 1H), 11.48 (br s, 1H), 10.78 (br s, 1H), 9.73 (s, 1H), 8.5-8.6 (m, 1H), 8.2-8.3 (m, 1H), 7.9-8.0 (m, 1H), 7.7-7.8 (m, 1H), 7.4-7.5 (m, 2H), 7.14 (br d, 2H, J=19.4 Hz), 6.99 (br d, 1H, J=2.0 Hz), 6.2-6.2 (m, 1H), 2.0-2.1 (m, 1H), 0.8-0.9 (m, 4H)

MS(ESI+) m/z 386 (M+H)⁺

Examples 24: Synthesis of N-(3-(2-(cyclopropanecarboxamido)pyridin-4-yl)-1H-indol-7-yl)-4-methylnicotinamide

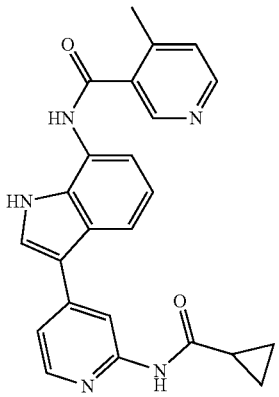 [SMILES: Cc1ccncc1C(=O)Nc1cccc2c(-c3ccnc(NC(=O)C4CC4)c3)c[nH]c12]

¹H NMR (DMSO-d₆, 400 MHz) δ 11.4-11.5 (m, 1H), 10.7-10.8 (m, 1H), 10.34 (s, 1H), 8.8-8.9 (m, 1H), 8.58 (br s, 2H), 8.2-8.3 (m, 1H), 8.0-8.0 (m, 1H), 7.8-7.9 (m, 1H), 7.5-7.6 (m, 1H), 7.4-7.5 (m, 2H), 7.1-7.2 (m, 1H), 3.4-3.4 (m, 3H), 2.0-2.1 (m, 1H), 0.8-0.9 (m, 4H)

MS(ESI+) m/z 412 (M+H)⁺

Examples 25: Synthesis of (E)-N-(4-(7-(2-cyano-3-(thiophen-2-yl)acrylamido)-1H-indol-3-yl)pyridin-2-yl)cyclopropanecarboxamide

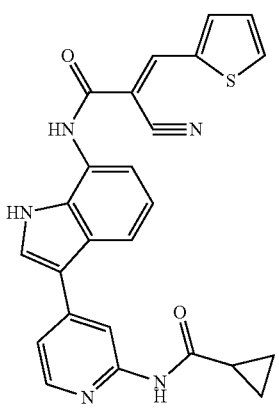 [SMILES: N#C/C(=C\c1cccs1)C(=O)Nc1cccc2c(-c3ccnc(NC(=O)C4CC4)c3)c[nH]c12]

¹H NMR (DMSO-d₆, 400 MHz) δ 11.5-11.5 (m, 1H), 10.7-10.8 (m, 1H), 10.29 (s, 1H), 8.59 (d, 2H, J=19.2 Hz), 8.2-8.3 (m, 1H), 8.1-8.2 (m, 1H), 7.9-8.0 (m, 2H), 7.8-7.9 (m, 1H), 7.3-7.5 (m, 2H), 7.20 (br d, 2H, J=19.0 Hz), 2.0-2.1 (m, 1H), 0.8-0.9 (m, 4H)

MS(ESI+) m/z 454 (M+H)⁺

Examples 26: Synthesis of N-(4-(7-(2-cyano-3-methylbut-2-enamido)-1-methyl-1H-indol-3-yl)pyridin-2-yl)cyclopropanecarboxamide

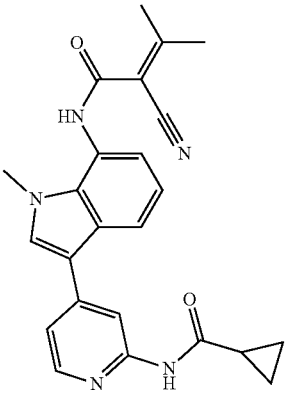 [SMILES: CC(C)=C(C#N)C(=O)Nc1cccc2c(-c3ccnc(NC(=O)C4CC4)c3)cn(C)c12]

¹H NMR (400 MHz, DMSO-d₆) δ 10.80 (s, 1H), 10.43 (s, 1H), 8.49-8.54 (m, 1H), 8.25-8.31 (m, 1H), 8.17-8.23 (m, 1H), 7.91 (s, 1H), 7.32-7.37 (m, 1H), 7.17-7.23 (m, 1H), 7.01-7.08 (m, 1H), 2.21 (s, 3H), 2.01-2.08 (m, 1H), 1.16-1.26 (m, 6H), 0.78-0.87 (m, 4H)

MS(ESI+) m/z 414 (M+H)⁺

Examples 27: Synthesis of 4-cyano-N-(3-(2-(cyclopropanecarboxamido)pyridin-4-yl)-1H-indol-7-yl)benzamide

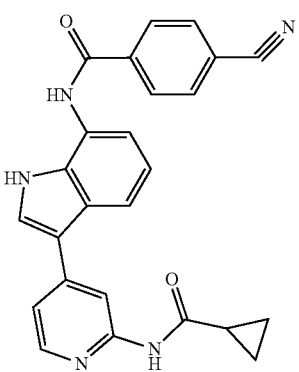 [SMILES: N#Cc1ccc(C(=O)Nc2cccc3c(-c4ccnc(NC(=O)C5CC5)c4)c[nH]c23)cc1]

¹H NMR (DMSO-d₆, 400 MHz) δ 11.5-11.6 (m, 1H), 10.7-10.9 (m, 1H), 10.4-10.5 (m, 1H), 8.5-8.6 (m, 1H), 8.2-8.3 (m, 1H), 8.22 (br d, 2H, J=8.1 Hz), 8.07 (d, 2H, J=8.2 Hz), 8.00 (d, 1H, J=2.6 Hz), 7.8-7.9 (m, 1H), 7.4-7.5 (m, 1H), 7.38 (d, 1H, J=7.5 Hz), 7.20 (s, 1H), 2.0-2.1 (m, 1H), 0.8-0.9 (m, 4H)

MS(ESI+) m/z 422 (M+H)⁺

Examples 28: Synthesis of N-(3-(2-(cyclopropanecarboxamido)pyridin-4-yl)-1H-indol-7-yl)-6-methylnicotinamide

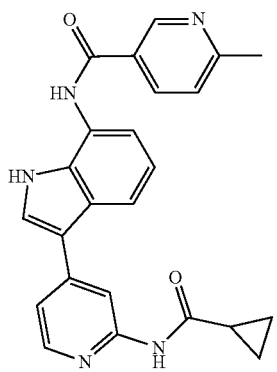 [SMILES: Cc1ccc(C(=O)Nc2cccc3c(-c4ccnc(NC(=O)C5CC5)c4)c[nH]c23)cn1]

¹H NMR (DMSO-d₆, 400 MHz) δ 11.53 (br s, 1H), 10.79 (s, 1H), 10.34 (s, 1H), 9.0-9.1 (m, 1H), 8.58 (s, 1H), 8.27 (br d, 2H, J=5.3 Hz), 7.99 (d, 1H, J=2.4 Hz), 7.8-7.9 (m, 1H), 7.4-7.5 (m, 2H), 7.38 (s, 1H), 7.19 (s, 1H), 2.58 (s, 3H), 2.0-2.1 (m, 1H), 0.8-0.9 (m, 4H)

MS(ESI+) m/z 412 (M+H)⁺

Examples 29: Synthesis of N-(3-(2-(cyclopropanecarboxamido)pyridin-4-yl)-1H-indol-7-yl)-6-(trifluoromethyl) nicotinamide

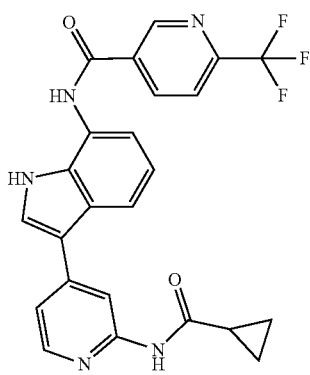 [SMILES: O=C(Nc1cccc2c(-c3ccnc(NC(=O)C4CC4)c3)c[nH]c12)c1ccc(C(F)(F)F)nc1]

¹H NMR (DMSO-d₆, 400 MHz) δ 11.5-11.6 (m, 1H), 10.80 (s, 1H), 10.75 (s, 1H), 9.0-9.1 (m, 1H), 8.6-8.6 (m, 1H), 8.4-8.5 (m, 1H), 8.2-8.3 (m, 2H), 8.0-8.1 (m, 1H), 7.9-7.9 (m, 1H), 7.4-7.5 (m, 1H), 73-7.4 (m, 1H), 7.2-73 (m, 1H), 2.0-2.1 (m, 1H), 0.8-0.9 (m, 4H)

MS(ESI+) m/z 466 (M+H)⁺

Examples 30: Synthesis of N-(3-(2-(cyclopropanecarboxamido)pyridin-4-yl)-1H-indol-7-yl)-5,6-difluoronicotinamide

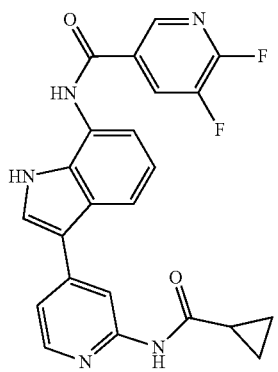 [SMILES: O=C(Nc1cccc2c(-c3ccnc(NC(=O)C4CC4)c3)c[nH]c12)c1cnc(F)c(F)c1]

¹H NMR (DMSO-d₆, 400 MHz) δ 11.4-11.5 (m, 1H), 10.80 (s, 1H), 10.67 (s, 1H), 8.58 (s, 1H), 8.27 (s, 2H), 8.04 (d, 1H, J=1.8 Hz), 7.8-7.9 (m, 2H), 7.44 (br d, 2H, J=6.8 Hz), 7.21 (s, 1H), 2.0-2.1 (m, 1H), 0.7-0.9 (m, 4H)

MS(ESI+) m/z 434 (M+H)⁺

Examples 31: Synthesis of N-(3-(2-(cyclopropanecarboxamido)pyridin-4-yl)-1H-indol-7-yl)-5-fluoronicotinamide

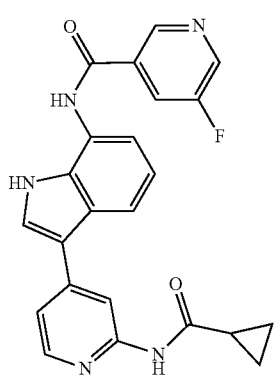 [SMILES: O=C(Nc1cccc2c(-c3ccnc(NC(=O)C4CC4)c3)c[nH]c12)c1cncc(F)c1]

¹H NMR (DMSO-d₆, 400 MHz) δ 11.4-11.5 (m, 1H), 10.8-10.8 (m, 1H), 8.8-8.8 (m, 1H), 8.6-8.7 (m, 1H), 8.6-8.7 (m, 1H), 8.5-8.6 (m, 1H), 8.57 (s, 1H), 8.2-8.3 (m, 1H), 8.0-8.0 (m, 1H), 7.87 (br s, 2H), 7.5-7.5 (m, 1H), 7.4-7.4 (m, 1H), 7.2-73 (m, 1H), 2.0-2.1 (m, 1H), 0.8-0.9 (m, 4H)

MS(ESI+) m/z 416 (M+H)⁺

Examples 32: Synthesis of 6-chloro-N-(3-(2-(cyclopropanecarboxamido)pyridin-4-yl)-1H-indol-7-yl) nicotinamide

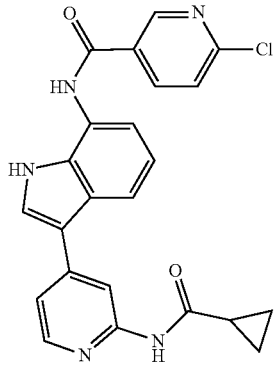 [SMILES: O=C(Nc1cccc2c(-c3ccnc(NC(=O)C4CC4)c3)c[nH]c12)c1ccc(Cl)nc1]

$^1$H NMR (DMSO-$d_6$, 400 MHz) δ 8.61-8.69 (m, 1H), 8.31-8.39 (m, 1H), 8.26 (d, 1H, J=5.1 Hz), 8.12 (s, 1H), 7.98 (br s, 2H), 7.8-7.8 (m, 1H), 7.62 (br d, 1H, J=1.1 Hz), 7.4-7.5 (m, 1H), 7.1-7.2 (m, 1H), 2.0-2.1 (m, 1H), 0.87 (br d, 4H, J=1.1 Hz)

MS(ESI+) m/z 433 (M+H)$^+$

Examples 33: Synthesis of N-(3-(2-(cyclopropanecarboxamido)pyridin-4-yl)-1H-indol-7-yl)-1H-pyrazole-3-carboxamide

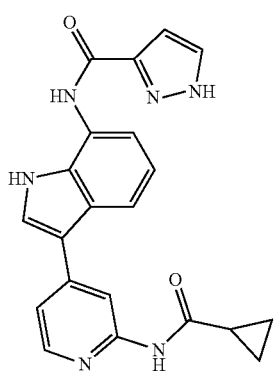 [SMILES: O=C(Nc1cccc2c(-c3ccnc(NC(=O)C4CC4)c3)c[nH]c12)c1cc[nH]n1]

$^1$H NMR (DMSO-$d_6$, 400 MHz) δ 11.5-11.6 (m, 1H), 10.7-10.8 (m, 1H), 10.0-10.1 (m, 1H), 8.57 (s, 1H), 8.2-83 (m, 1H), 7.93 (br d, 1H, J=1.8 Hz), 7.9-8.0 (m, 1H), 7.8-7.8 (m, 1H), 7.5-7.5 (m, 1H), 7.4-7.4 (m, 1H), 7.1-7.2 (m, 1H), 6.83 (br s, 1H), 2.05 (br d, 1H, J=2.4 Hz), 0.8-0.9 (m, 4H)

MS(ESI+) m/z 387 (M+H)$^+$

Examples 34: Synthesis of N-(3-(2-(cyclopropanecarboxamido)pyridin-4-yl)-1H-indol-7-yl)-1-methyl-2-oxo-1,2-dihydropyridine-3-carboxamide

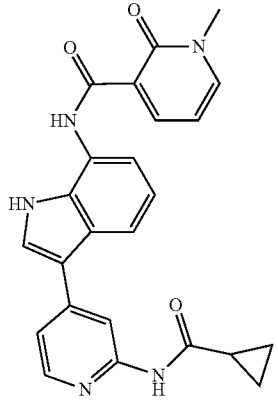 [SMILES: Cn1cccc(C(=O)Nc2cccc3c(-c4ccnc(NC(=O)C5CC5)c4)c[nH]c23)c1=O]

$^1$H NMR (DMSO-$d_6$, 400 MHz) δ 12.08 (s, 1H), 11.3-11.5 (m, 1H), 10.8-11.0 (m, 1H), 8.50 (br dd, 2H, J=2.1, 7.2 Hz), 8.26 (br d, 2H, J=5.5 Hz), 7.9-8.0 (m, 1H), 7.83 (s, 1H), 7.4-7.5 (m, 1H), 7.31 (s, 1H), 7.19 (s, 1H), 6.64 (s, 1H), 3.68 (s, 3H), 2.0-2.1 (m, 1H), 0.8-0.9 (m, 4H)

MS(ESI+) m/z 428 (M+H)$^+$

Examples 35: Synthesis of 2-cyano-N-(3-(2-(cyclopropanecarboxamido)pyridin-4-yl)-1H-indol-7-yl) isonicotin amide

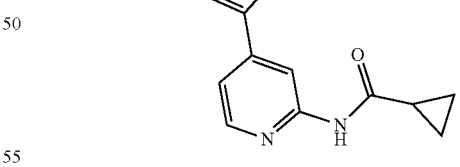

$^1$H NMR (DMSO-$d_6$, 400 MHz) δ 11.5-11.6 (m, 1H), 10.8-10.8 (m, 1H), 10.7-10.7 (m, 1H), 9.0-9.1 (m, 1H), 8.6-8.7 (m, 1H), 8.5-8.6 (m, 1H), 8.29 (s, 2H), 8.0-8.1 (m, 1H), 7.9-7.9 (m, 1H), 7.4-7.5 (m, 1H), 7.4-7.4 (m, 1H), 7.2-7.2 (m, 1H), 2.0-2.1 (m, 1H), 0.8-0.9 (m, 4H)

MS(ESI+) m/z 423 (M+H)$^+$

Examples 36: Synthesis of N-(3-(2-(cyclopropanecarboxamido)pyridin-4-yl)-1H-indol-7-yl)-4-ethyl-1H-pyrrole-2-carboxamide

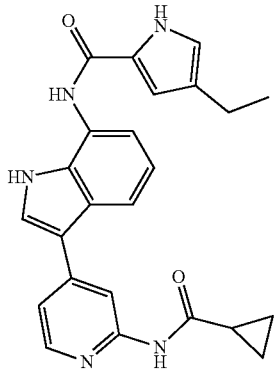 [SMILES: CCc1c[nH]c(C(=O)Nc2cccc3c(-c4ccnc(NC(=O)C5CC5)c4)c[nH]c23)c1]

$^1$H NMR (DMSO-d$_6$, 400 MHz) δ 11.5-11.5 (m, 1H), 11.4-11.5 (m, 1H), 10.7-10.8 (m, 1H), 9.5-9.7 (m, 1H), 8.57 (s, 1H), 8.2-8.3 (m, 1H), 7.95 (s, 1H), 7.7-7.8 (m, 1H), 7.43 (s, 2H), 7.1-7.2 (m, 1H), 7.0-7.0 (m, 1H), 6.8-6.8 (m, 1H), 2.0-2.1 (m, 1H), 1.23 (br s, 2H), 1.18 (t, 4H, J=7.6 Hz), 0.85 (br d, 4H, J=14.3 Hz)

MS(ESI+) m/z 414 (M+H)$^+$

Examples 37: Synthesis of 3-(2-(cyclopropanecarboxamido)pyridin-4-yl)-N-(2,2,2-trifluoroethyl)-7-(3-(2,2,2-trifluoroethyl) ureido)-1H-indole-1-carboxamide

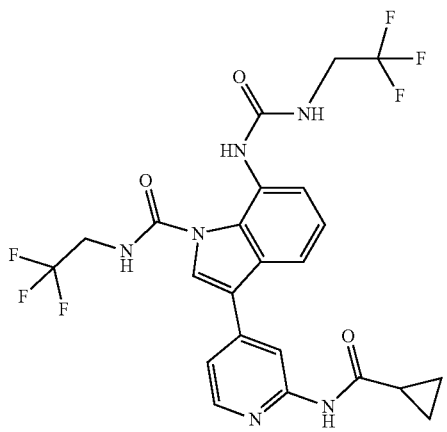 [SMILES: O=C(NCC(F)(F)F)Nc1cccc2c(-c3ccnc(NC(=O)C4CC4)c3)cn(C(=O)NCC(F)(F)F)c12]

$^1$H NMR (DMSO-d$_6$, 400 MHz) δ 11.98 (br s, 1H), 10.79 (s, 1H), 8.58 (s, 1H), 8.2-8.3 (m, 2H), 8.03 (d, 1H, J=8.2 Hz), 7.96 (s, 1H), 7.44 (br d, 1H, J=5.3 Hz), 7.25 (t, 1H, J=8.0 Hz), 7.05 (d, 1H, J=7.7 Hz), 3.8-4.0 (m, 4H), 2.0-2.1 (m, 1H), 0.8-0.9 (m, 4H)

MS(ESI+) m/z 543 (M+H)$^+$

Examples 38: Synthesis of N-(3-(2-(cyclopropanecarboxamido)pyridin-4-yl)-1H-indol-7-yl)-3-fluorobenzamide

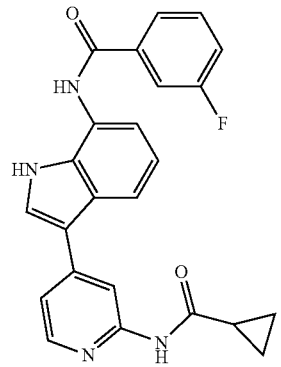 [SMILES: O=C(Nc1cccc2c(-c3ccnc(NC(=O)C4CC4)c3)c[nH]c12)c1cccc(F)c1]

$^1$H NMR (DMSO-d$_6$, 400 MHz) δ 11.24 (br s, 1H), 10.71 (s, 1H), 8.53 (s, 1H), 8.22 (d, 1H, J=5.3 Hz), 7.90 (d, 1H, J=2.7 Hz), 7.37 (dd, 1H, J=1.3, 5.3 Hz), 7.22 (d, 1H, J=8.1 Hz), 6.88 (t, 1H, J=7.8 Hz), 6.42 (d, 1H, J=7.5 Hz), 1.9-2.1 (m, 1H), 0.8-0.9 (m, 4H)

MS(ESI+) m/z 415 (M+H)$^+$

Examples 39: Synthesis of N-(4-(7-(3-(2,2,2-trifluoroethyl)ureido)-1H-indol-3-yl)pyridin-2-yl)cyclopropanecarboxamide

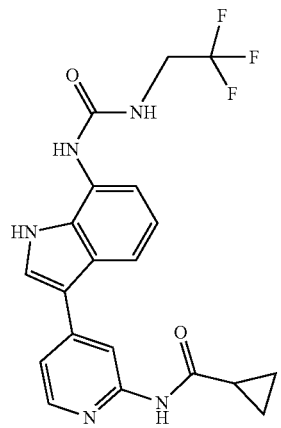 [SMILES: O=C(NCC(F)(F)F)Nc1cccc2c(-c3ccnc(NC(=O)C4CC4)c3)c[nH]c12]

$^1$H NMR (400 MHz, DMSO-d$_6$) δ 11.21-11.33 (m, 1H), 10.71-10.80 (m, 1H), 8.67-8.76 (m, 1H), 8.51-8.56 (m, 1H), 8.21-8.29 (m, 1H), 7.90-7.95 (m, 1H), 7.65-7.71 (m, 1H), 7.36-7.43 (m, 1H), 7.23-7.29 (m, 1H), 7.05-7.12 (m, 1H), 6.89-6.96 (m, 1H), 3.92-4.03 (m, 2H), 1.99-2.09 (m, 1H), 0.79-0.88 (m, 4H)

MS(ESI+) m/z 418 (M+H)$^+$

Examples 40: Synthesis of N-(4-(4-(2-cyano-3-methylbut-2-enamido)-1H-indol-1-yl)pyridin-2-yl)cyclopropanecarboxamide

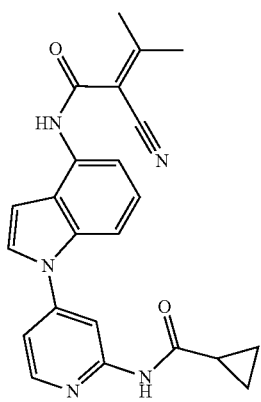 [SMILES: CC(C)=C(C#N)C(=O)Nc1cccc2c1ccn2-c1ccnc(NC(=O)C2CC2)c1]

[Step 1] Synthesis of N-(4-fluoropyridin-2-yl)cyclopropanecarboxamide

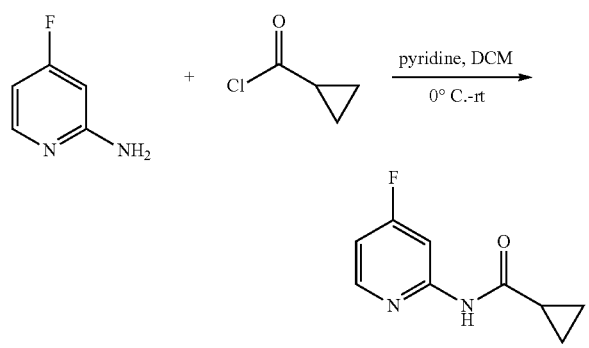

2-amino-4-fluoropyridine (5 g, 44.6 mmol) was dissolved in dichloromethane, after which pyridine (10.5 mL) and cyclopropanecarbonyl chloride (4.9 mL, 53.5 mmol) were slowly added dropwise thereto at 0° C., and then stirred at the same temperature for two hours. A reaction mixture was added to water, after which a resulting solid was filtered and then dried under reduced pressure to obtain a title compound (5.67 g, 90.1 mmol) (70%).

MS(ESI+) m/z 181 (M+H)+

[Step 2] Synthesis of N-(4-(4-nitro-1H-indol-1-yl)pyridin-2-yl)cyclopropanecarboxamide

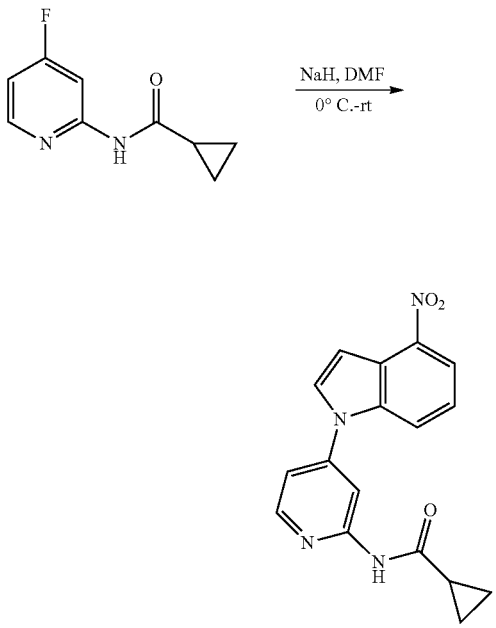

4-nitro-1H-indole (4.3 g, 26.6 mmol) was dissolved in dimethylformamide (50 mL), after which NaH 60% in oil (1.1 g, 26.6 mmol) was slowly added thereto at 0° C. A resulting mixture was stirred for 0.5 hours, after N-(4-fluoropyridine-2-yl)cyclopropanecarboxamide (4.0 g, 22.2 mmol) was added thereto, such that a reaction mixture was stirred. When reaction was completed, said mixture was stirred at room temperature, after which saturated NH4Cl aqueous solution was added thereto while being stirred. An organic layer was extracted with dichloromethane and then concentrated under reduced pressure, after which a resulting residue was separated with column chromatography to obtain a title compound.

$^1$H NMR (400 MHz, DMSO-$d_6$) δ 11.09-11.27 (m, 1H), 8.46-8.56 (m, 1H), 8.34-8.42 (m, 1H), 8.13-8.24 (m, 3H), 7.46-7.55 (m, 1H), 7.39-7.46 (m, 1H), 7.30-7.37 (m, 1H), 1.99-2.12 (m, 1H), 0.79-0.93 (m, 4H)

MS(ESI+) m/z 323 (M+H)+

[Step 3] Synthesis of N-(4-(4-amino-1H-indol-1-yl)pyridin-2-yl)cyclopropanecarboxamide

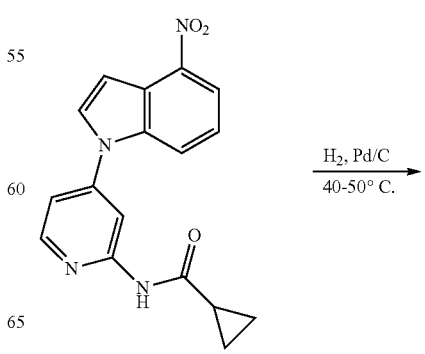

47

-continued

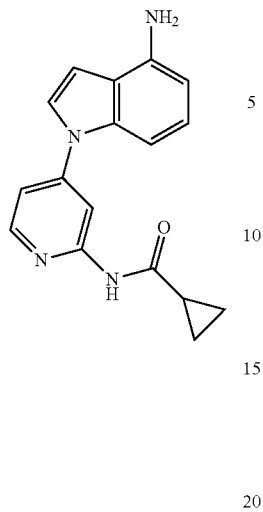

N-[4-(4-nitro indole-1-yl)-2-pyridyl]cyclopropanecarboxamide (5 g, 15.5 mmol) was inserted into methanol (100 mL), after which Pd/C (500 mg) was added thereto, and then stirred at 40-50° C. under a hydrogen atmosphere for six hours. When reaction was completed, said mixture was cooled down to room temperature, and then filtered with celite. A resulting filtrate was distilled under reduced pressure, and then separated with column chromatography to obtain a title compound (3.9 g, 87%).

MS(ESI+) m/z 293 (M+H)$^+$

[Step 4] Synthesis of N-(4-(4-(2-cyano-3-methyl-but-2-enamido)-1H-indol-1-yl)pyridin-2-yl)cyclopropanecarboxamide A process was performed substantially the same as in Step 8 of Example 1 to obtain a product, i.e., N-(4-(4-(2-cyano-3-methylbut-2-enamido)-1H-indol-1-yl)pyridine-2-yl)cyclopropanecarboxamide.

$^1$H NMR (400 MHz, DMSO-d$_6$) δ 11.04-11.12 (m, 1H), 10.41-10.54 (m, 1H), 8.42-8.48 (m, 1H), 8.38-8.42 (m, 1H), 7.75-7.80 (m, 1H), 7.58-7.66 (m, 2H), 7.36-7.40 (m, 1H), 7.24-7.30 (m, 1H) 6.91-6.98 (m, 1H), 2.20 (s, 3H), 2.13 (s, 3H), 2.02-2.07 (m, 1H), 1.19-1.26 (m, 2H), 0.83-0.87 (m, 4H).

MS(ESI+) m/z 400 (M+H)$^+$

Examples 41 to 62

Hereinafter, the compounds in Examples 41 to 62 were prepared by means of the same method as shown in Example 40, but did with an appropriate reactant, considering the reaction formula 2 and a structure of the compound to be prepared.

48

Examples 41: Synthesis of N-(4-(4-(2-cyanoacetamido)-1H-indol-1-yl)pyridin-2-yl)cyclopropanecarboxamide

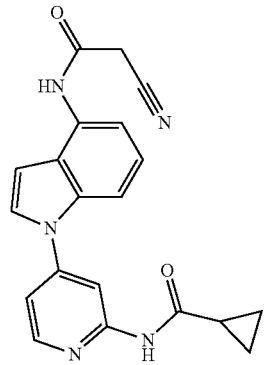 [SMILES: N#CCC(=O)Nc1cccc2c1ccn2-c1ccnc(NC(=O)C2CC2)c1]

$^1$H NMR (400 MHz, DMSO-d$_6$) δ 10.99-11.17 (m, 1H), 10.03-10.22 (m, 1H), 8.42-8.48 (m, 1H), 8.37-8.42 (m, 1H), 7.75-7.81 (m, 1H), 7.67-7.73 (m, 1H), 7.54-7.60 (m, 1H), 7.34-7.41 (m, 1H), 7.21-7.30 (m, 1H), 6.97-7.05 (m, 1H), 3.99-4.10 (m, 2H), 2.00-2.09 (m, 1H), 0.77-0.89 (m, 4H)

MS(ESI+) m/z 360 (M+H)$^+$

Examples 42: Synthesis of N-(1-(2-(cyclopropanecarboxamido)pyridin-4-yl)-1H-indol-4-yl)-1H-pyrrole-2-carboxamid

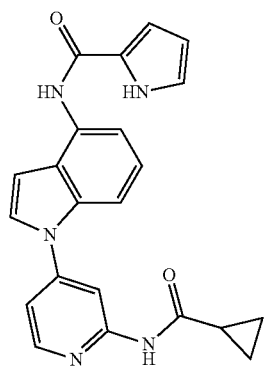 [SMILES: O=C(Nc1cccc2c1ccn2-c1ccnc(NC(=O)C2CC2)c1)c1ccc[nH]1]

$^1$H NMR (400 MHz, DMSO-d$_6$) δ 11.67-11.80 (m, 1H), 10.98-11.13 (m, 1H), 9.66-9.81 (m, 1H), 8.43 (s, 2H), 7.71-7.80 (m, 1H), 7.56-7.64 (m, 1H), 7.48-7.56 (m, 1H), 7.35-7.42 (m, 1H), 7.22-7.32 (m, 1H), 7.11-7.21 (m, 1H), 6.95-7.02 (m, 1H), 6.85-6.95 (m, 1H), 6.11-6.25 (m, 1H), 1.97-2.14 (m, 1H), 0.77-0.94 (m, 4H)

MS(ESI+) m/z 386 (M+H)$^+$

Examples 43: Synthesis of N-(1-(2-(cyclopropanecarboxamido)pyridin-4-yl)-1H-indol-4-yl)-2-methylthiazole-5-carboxamide

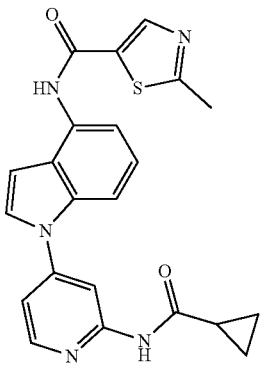 [SMILES: Cc1ncc(C(=O)Nc2cccc3c2ccn3-c2ccnc(NC(=O)C3CC3)c2)s1]

$^1$H NMR (400 MHz, DMSO-d$_6$) δ 11.02-11.14 (m, 1H), 10.03-10.15 (m, 1H), 8.40-8.49 (m, 2H), 8.33 (s, 1H), 7.75-7.83 (m, 1H), 7.67-7.73 (m, 1H), 7.59-7.66 (m, 1H), 7.36-7.45 (m, 1H), 7.26-7.34 (m, 1H), 6.75-6.84 (m, 1H), 2.80 (s, 3H), 1.99-2.11 (m, 1H), 0.86 (br d, J=4.76 Hz, 4H)

MS(ESI+) m/z 418 (M+H)$^+$

Examples 44: Synthesis of N-(1-(2-(cyclopropanecarboxamido)pyridin-4-yl)-1H-indol-4-yl)-3,5-difluorobenzamide

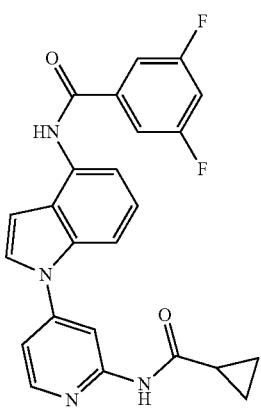 [SMILES: O=C(Nc1cccc2c1ccn2-c1ccnc(NC(=O)C2CC2)c1)c1cc(F)cc(F)c1]

$^1$H NMR (400 MHz, DMSO-d$_6$) δ 11.08 (s, 1H), 10.45 (s, 1H), 8.44 (s, 2H), 7.78 (s, 3H), 7.64-7.70 (m, 1H), 7.48-7.59 (m, 2H), 7.37-7.43 (m, 1H), 7.26-7.35 (m, 1H), 6.89-6.99 (m, 1H), 2.00-2.10 (m, 1H), 0.80-0.91 (m, 4H)

MS(ESI+) m/z 433 (M+H)$^+$

Examples 45: Synthesis of N-(1-(2-(cyclopropanecarboxamido)pyridin-4-yl)-1H-indol-4-yl)-1-methyl-2-oxo-1,2-dihydropyridine-3-carboxamide

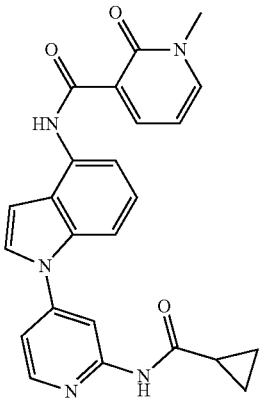 [SMILES: Cn1cccc(C(=O)Nc2cccc3c2ccn3-c2ccnc(NC(=O)C3CC3)c2)c1=O]

$^1$H NMR (400 MHz, DMSO-d$_6$) δ 12.71-12.87 (m, 1H), 10.96-11.22 (m, 1H), 8.38-8.62 (m, 3H), 8.16-8.26 (m, 2H), 7.78-7.94 (m, 1H), 7.48-7.66 (m, 1H), 7.34-7.45 (m, 1H), 7.23-7.33 (m, 1H), 6.83-6.97 (m, 1H), 6.55-6.72 (m, 1H), 3.64-3.76 (m, 3H), 1.97-2.17 (m, 1H), 0.77-0.96 (m, 4H)

MS(ESI+) m/z 428 (M+H)$^+$

Examples 46: Synthesis of N-(4-(4-(2-cyano-3-(thiophen-2-yl)acrylamido)-1H-indol-1-yl)pyridin-2-yl)cyclopropanecarboxamide

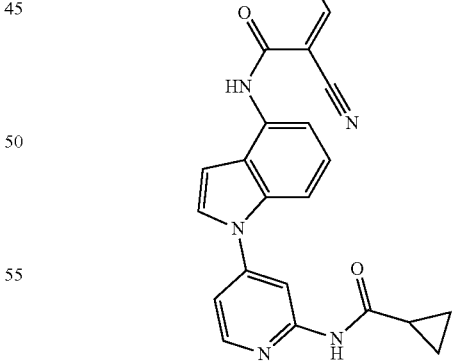

$^1$H NMR (400 MHz, DMSO-d$_6$) δ 11.02-11.12 (m, 1H), 10.25-10.40 (m, 1H), 8.57-8.64 (m, 1H), 8.40-8.49 (m, 2H), 8.11-8.20 (m, 1H), 7.94-8.01 (m, 1H), 7.76-7.83 (m, 1H), 7.61-7.70 (m, 1H), 7.45-7.50 (m, 1H), 7.34-7.42 (m, 2H), 7.24-7.33 (m, 1H), 6.85-6.93 (m, 1H), 2.00-2.13 (m, 1H), 0.73-0.92 (m, 4H)

MS(ESI+) m/z 454 (M+H)$^+$

Examples 47: Synthesis of 4-cyano-N-(1-(2-(cyclo-propanecarboxamido)pyridin-4-yl)-1H-indol-4-yl) benzamide

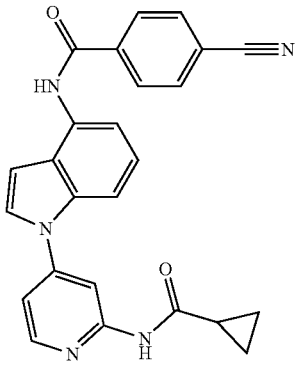 [SMILES: N#Cc1ccc(C(=O)Nc2cccc3c2ccn3-c2ccnc(NC(=O)C3CC3)c2)cc1]

¹H NMR (400 MHz, DMSO-d₆) δ 11.04-11.14 (m, 1H), 10.48-10.62 (m, 1H), 8.40-8.49 (m, 2H), 8.14-8.23 (m, 2H), 7.99-8.09 (m, 2H), 7.74-7.83 (m, 1H), 7.61-7.70 (m, 1H), 7.52-7.60 (m, 1H), 7.35-7.42 (m, 1H), 7.26-7.34 (m, 1H), 6.91-6.97 (m, 1H), 2.00-2.11 (m, 1H), 0.80-0.90 (m, 4H)

MS(ESI+) m/z 422 (M+H)⁺

Examples 48: Synthesis of N-(4-(4-(2-cyano-3-phenylacrylamido)-1H-indol-1-yl)pyridin-2-yl)cyclopropanecarboxamide

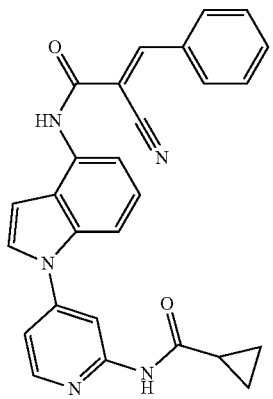 [SMILES: N#C/C(=C\c1ccccc1)C(=O)Nc1cccc2c1ccn2-c1ccnc(NC(=O)C2CC2)c1]

¹H NMR (400 MHz, DMSO-d₆) δ 11.05-11.14 (m, 1H), 10.37-10.49 (m, 1H), 8.41-8.49 (m, 2H), 8.35-8.40 (m, 1H), 8.00-8.09 (m, 2H), 7.78-7.84 (m, 1H), 7.60-7.69 (m, 4H), 7.47-7.54 (m, 1H), 7.38-7.43 (m, 1H), 7.26-7.34 (m, 1H), 6.90-6.98 (m, 1H), 1.98-2.11 (m, 1H), 0.79-0.90 (m, 4H)

MS(ESI+) m/z 448 (M+H)⁺

Examples 49: Synthesis of N-(1-(2-(cyclopropanecarboxamido)pyridin-4-yl)-1H-indol-4-yl)-1-methyl-1H-indole-2-carboxamide

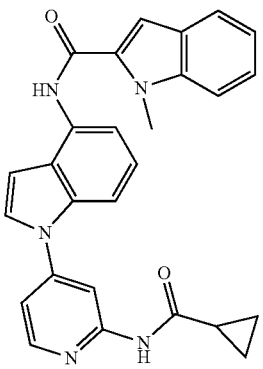 [SMILES: Cn1c(C(=O)Nc2cccc3c2ccn3-c2ccnc(NC(=O)C3CC3)c2)cc2ccccc21]

¹H NMR (400 MHz, DMSO-d₆) δ 11.04-11.12 (m, 1H), 10.31-10.40 (m, 1H), 8.40-8.48 (m, 2H), 7.76-7.82 (m, 1H), 7.69-7.74 (m, 1H), 7.61-7.67 (m, 1H), 7.52-7.61 (m, 2H), 7.37-7.44 (m, 2H), 7.27-7.35 (m, 2H), 7.09-7.19 (m, 1H), 6.92-7.01 (m, 1H), 3.99-4.10 (m, 3H), 2.00-2.11 (m, 1H), 0.78-0.89 (m, 4H) ppm.

MS(ESI+) m/z 450 (M+H)⁺

Examples 50: Synthesis of 4-cyano-N-(1-(2-(cyclopropanecarboxamido)pyridin-4-yl)-1H-indol-4-yl) tetrahydro-2H-pyran-4-carboxamide

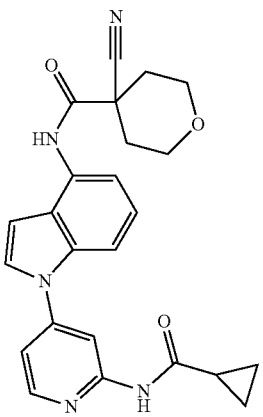 [SMILES: N#CC1(C(=O)Nc2cccc3c2ccn3-c2ccnc(NC(=O)C3CC3)c2)CCOCC1]

¹H NMR (400 MHz, DMSO-d₆) δ 11.09 (s, 1H), 10.22-10.38 (m, 1H), 8.37-8.49 (m, 2H), 7.79 (d, J=3.48 Hz, 1H), 7.61-7.71 (m, 1H), 7.34-7.42 (m, 1H), 7.22-7.31 (m, 2H), 7.00-7.09 (m, 1H), 6.76 (d, J=3.48 Hz, 1H), 3.99 (br d, J=11.89 Hz, 2H), 3.54-3.68 (m, 2H), 2.12-2.29 (m, 4H), 1.99-2.10 (m, 1H), 0.86 (br d, J=4.03 Hz, 4H)

MS(ESI+) m/z 430 (M+H)⁺

Examples 51: Synthesis of 2-cyano-N-(1-(2-(cyclopropanecarboxamido)pyridin-4-yl)-1H-indol-4-yl)isonicotinamide

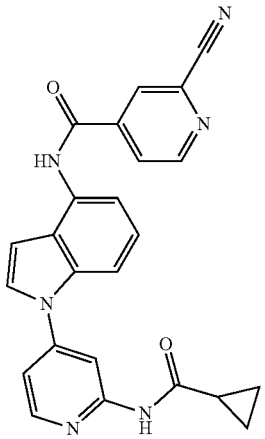 [SMILES: N#Cc1cc(C(=O)Nc2cccc3c2ccn3-c2ccnc(NC(=O)C3CC3)c2)ccn1]

$^1$H NMR (400 MHz, DMSO-d$_6$) δ 11.03-11.15 (m, 1H), 10.65-10.80 (m, 1H), 8.92-9.04 (m, 1H), 8.60 (s, 1H), 8.39-8.48 (m, 2H), 8.21-8.28 (m, 1H), 7.75-7.84 (m, 1H), 7.55-7.72 (m, 2H), 7.37-7.44 (m, 1H), 7.25-7.34 (m, 1H), 6.97-7.07 (m, 1H), 2.00-2.12 (m, 1H), 0.74-0.92 (m, 4H)

MS(ESI+) m/z 423 (M+H)$^+$

Examples 52: Synthesis of N-(1-(2-(cyclopropanecarboxamido)pyridin-4-yl)-1H-indol-4-yl)-2-fluoroisonicotinamide

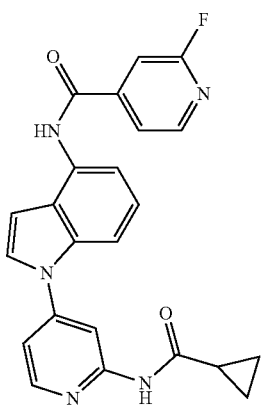 [SMILES: O=C(Nc1cccc2c1ccn2-c1ccnc(NC(=O)C2CC2)c1)c1ccnc(F)c1]

$^1$H NMR (400 MHz, DMSO-d$_6$) δ 11.01-11.16 (m, 1H), 10.54-10.68 (m, 1H), 8.41-8.51 (m, 3H), 7.86-7.98 (m, 1H), 7.72-7.83 (m, 2H), 7.61-7.68 (m, 1H), 7.52-7.60 (m, 1H), 7.36-7.44 (m, 1H), 7.26-7.36 (m, 1H), 6.90-7.00 (m, 1H), 1.99-2.10 (m, 1H), 0.86 (br s, 4H)

MS(ESI+) m/z 416 (M+H)$^+$

Examples 53: Synthesis of N-(1-(2-(cyclopropanecarboxamido)pyridin-4-yl)-1H-indol-4-yl)-2,3-difluoroisonicotinamide

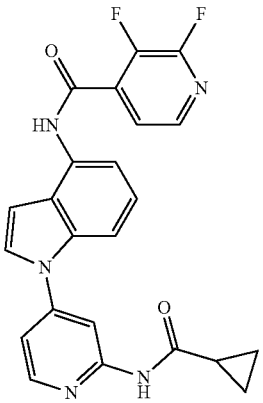 [SMILES: O=C(Nc1cccc2c1ccn2-c1ccnc(NC(=O)C2CC2)c1)c1ccnc(F)c1F]

$^1$H NMR (400 MHz, DMSO-d$_6$) δ 11.09 (s, 1H), 10.52-10.81 (m, 1H), 8.35-8.53 (m, 2H), 8.14-8.29 (m, 1H), 7.79 (br d, J=3.48 Hz, 2H), 7.70-7.76 (m, 1H), 7.64 (d, J=8.42 Hz, 1H), 7.34-7.43 (m, 1H), 7.22-7.34 (m, 1H), 6.91-7.06 (m, 1H), 2.00-2.10 (m, 1H), 0.86 (br d, J=4.21 Hz, 4H)

MS(ESI+) m/z 434 (M+H)$^+$

Examples 54: Synthesis of N-(4-(4-(2-cyanopropanamido)-1H-indol-1-yl)pyridin-2-yl)cyclopropanecarboxamide

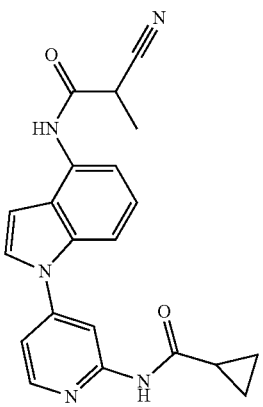 [SMILES: CC(C#N)C(=O)Nc1cccc2c1ccn2-c1ccnc(NC(=O)C2CC2)c1]

$^1$H NMR (400 MHz, DMSO-d$_6$) δ 11.08 (br s, 1H), 10.12-10.37 (m, 2H), 8.36-8.49 (m, 2H), 7.74-7.85 (m, 1H), 7.64-7.71 (m, 1H), 7.54-7.63 (m, 1H), 7.34-7.44 (m, 1H), 7.20-7.31 (m, 1H), 6.93-7.05 (m, 1H), 4.11-4.24 (m, 1H), 1.97-2.13 (m, 1H), 1.57 (d, J=7.14 Hz, 3H), 0.85 (br s, 4H)

MS(ESI+) m/z 374 (M+H)$^+$

Examples 55: Synthesis of N-(1-(2-(cyclopropanecarboxamido)pyridin-4-yl)-1H-indol-4-yl)-1H-pyrazole-3-carboxamide

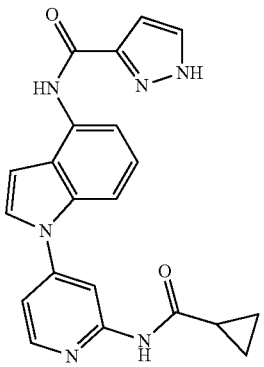 [SMILES: O=C(Nc1cccc2c1ccn2-c1ccnc(NC(=O)C2CC2)c1)c1cc[nH]n1]

¹H NMR (400 MHz, DMSO-d₆) δ 10.99-11.18 (m, 1H), 9.68-10.13 (m, 1H), 8.35-8.52 (m, 2H), 7.83-7.95 (m, 1H), 7.71-7.82 (m, 1H), 7.55-7.71 (m, 2H), 7.35-7.46 (m, 1H), 7.21-7.35 (m, 1H), 6.71-6.93 (m, 2H), 1.98-2.13 (m, 1H), 0.73-0.92 (m, 4H)

MS(ESI+) m/z 387 (M+H)⁺

Examples 56: Synthesis of N-(1-(2-(cyclopropanecarboxamido)pyridin-4-yl)-1H-indol-4-yl)-3-fluoro-4-methoxybenzamide

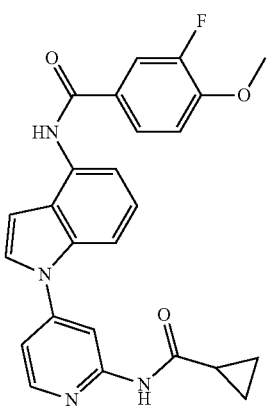 [SMILES: COc1ccc(C(=O)Nc2cccc3c2ccn3-c2ccnc(NC(=O)C3CC3)c2)cc1F]

¹H NMR (400 MHz, DMSO-d₆) δ 11.01-11.17 (m, 1H), 10.10-10.30 (m, 1H), 8.39-8.51 (m, 2H), 7.87-8.02 (m, 2H), 7.72-7.80 (m, 1H), 7.59-7.68 (m, 1H), 7.45-7.53 (m, 1H), 7.24-7.42 (m, 3H), 6.85-6.98 (m, 1H), 3.94 (s, 3H), 2.00-2.10 (m, 1H), 0.86 (br d, J=3.84 Hz, 4H)

MS(ESI+) m/z 445 (M+H)⁺

Examples 57: Synthesis of (1R,2S)-2-cyano-N-(1-(2-(cyclopropanecarboxamido)pyridin-4-yl)-1H-indol-4-yl) cyclopropane-1-carboxamide

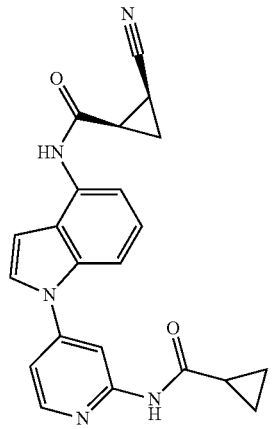 [SMILES: N#C[C@H]1C[C@H]1C(=O)Nc1cccc2c1ccn2-c1ccnc(NC(=O)C2CC2)c1]

¹H NMR (400 MHz, DMSO-d₆) δ 10.97-11.19 (m, 1H), 10.25-10.47 (m, 1H), 8.34-8.54 (m, 2H), 7.70-7.85 (m, 2H), 7.50-7.62 (m, 1H), 7.34-7.42 (m, 1H), 7.20-7.28 (m, 1H), 7.03-7.12 (m, 1H), 2.56-2.71 (m, 2H), 2.21-2.35 (m, 1H), 1.99-2.10 (m, 1H), 1.40-1.56 (m, 2H), 0.86 (br d, J=3.84 Hz, 4H)

MS(ESI+) m/z 386 (M+H)⁺

Examples 58: Synthesis of N-(4-(4-(2-(1-cyanocyclopropyl)acetamido)-1H-indol-1-yl)pyridin-2-yl) cyclopropane carboxamide

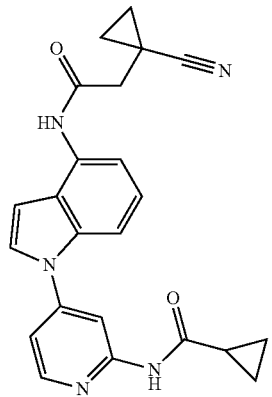 [SMILES: N#CC1(CC(=O)Nc2cccc3c2ccn3-c2ccnc(NC(=O)C3CC3)c2)CC1]

¹H NMR (400 MHz, DMSO-d₆) δ 11.00-11.10 (m, 1H), 9.80-9.91 (m, 1H), 8.38-8.48 (m, 2H), 7.72-7.81 (m, 2H), 7.50-7.58 (m, 1H), 7.32-7.41 (m, 1H), 7.19-7.27 (m, 1H), 6.99-7.07 (m, 1H), 2.75 (s, 2H), 2.02-2.11 (m, 1H), 0.85 (br s, 4H)

MS(ESI+) m/z 400 (M+H)⁺

Examples 59: Synthesis of N-(1-(2-(cyclopropanecarboxamido)pyridin-4-yl)-1H-indol-4-yl)-6-methylnicotinamide

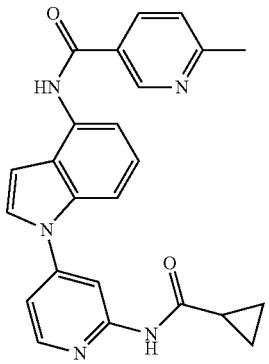 [SMILES: Cc1ccc(C(=O)Nc2cccc3c2ccn3-c2ccnc(NC(=O)C3CC3)c2)cn1]

$^1$H NMR (400 MHz, DMSO-d$_6$) δ 10.99-11.14 (m, 1H), 10.31-10.47 (m, 1H), 8.98-9.11 (m, 1H), 8.38-8.48 (m, 2H), 8.20-8.33 (m, 1H), 7.72-7.82 (m, 1H), 7.61-7.67 (m, 1H), 7.53-7.58 (m, 1H), 7.42-7.47 (m, 1H), 7.37-7.42 (m, 1H), 7.24-7.34 (m, 1H), 6.90-7.00 (m, 1H), 2.58 (s, 3H), 2.02-2.11 (m, 1H), 1.22-1.31 (m, 5H), 0.80-0.92 (m, 4H)

MS(ESI+) m/z 412 (M+H)$^+$

Examples 60: Synthesis of N-(4-(4-(2,3-dimethylbut-2-enamido)-1H-indol-1-yl)pyridin-2-yl)cyclopropanecarboxamide

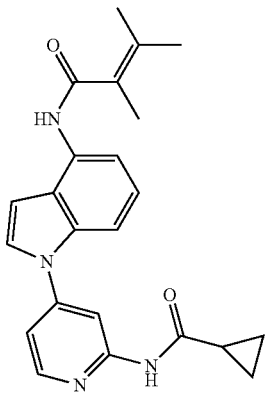 [SMILES: CC(C)=C(C)C(=O)Nc1cccc2c1ccn2-c1ccnc(NC(=O)C2CC2)c1]

$^1$H NMR (400 MHz, DMSO-d$_6$) δ 10.97-11.15 (m, 1H), 9.69-9.87 (m, 1H), 8.35-8.51 (m, 2H), 7.65-7.78 (m, 2H), 7.50-7.61 (m, 1H), 7.31-7.41 (m, 1H), 7.15-7.28 (m, 1H), 6.96-7.07 (m, 1H), 2.68 (s, 6H), 2.00-2.10 (m, 1H), 1.85-1.92 (m, 3H), 1.78-1.85 (m, 3H), 1.74 (s, 3H), 0.77-0.91 (m, 4H)

MS(ESI+) m/z 389 (M+H)$^+$

Examples 61: Synthesis of N-(4-(4-(3-(2,4-difluorophenyl)ureido)-1H-indol-1-yl)pyridin-2-yl)cyclopropanecarboxamide

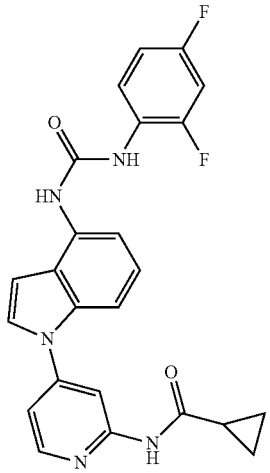 [SMILES: O=C(Nc1ccc(F)cc1F)Nc1cccc2c1ccn2-c1ccnc(NC(=O)C2CC2)c1]

$^1$H NMR (400 MHz, DMSO-d$_6$) δ 8.98-9.08 (m, 1H), 8.80-8.91 (m, 1H), 8.38-8.49 (m, 2H), 8.10-8.30 (m, 1H), 7.81-7.92 (m, 1H), 7.74-7.81 (m, 1H), 7.42-7.51 (m, 1H), 7.28-7.42 (m, 2H), 7.17-7.27 (m, 1H), 7.03-7.13 (m, 1H), 6.86-6.97 (m, 1H), 2.01-2.12 (m, 1H), 0.86 (br d, J=4.39 Hz, 4H)

MS(ESI+) m/z 448 (M+H)$^+$

Examples 62: Synthesis of N-(4-(4-(3-(2,2,2-trifluoroethyl)ureido)-1H-indol-1-yl)pyridin-2-yl)cyclopropanecarboxamide

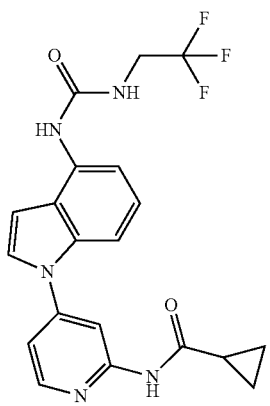 [SMILES: O=C(NCC(F)(F)F)Nc1cccc2c1ccn2-c1ccnc(NC(=O)C2CC2)c1]

$^1$H NMR (400 MHz, DMSO-d$_6$) δ 11.06 (s, 1H), 8.64-8.77 (m, 1H), 8.35-8.52 (m, 2H), 7.71-7.86 (m, 2H), 7.32-7.49 (m, 2H), 7.12-7.23 (m, 1H), 6.93-7.05 (m, 1H), 6.73-6.90 (m, 3H), 3.93-4.08 (m, 2H), 3.84 (m, 4H), 1.98-2.09 (m, 1H), 0.78-0.93 (m, 4H)

MS(ESI+) m/z 418 (M+H)$^+$

Hereinafter, the compound in Example 63 was prepared in such a way that synthesis was performed by means of the same method as shown in Example 1 or an appropriate reactant was used, considering the reaction formula 1 and a structure of the compound to be prepared.

Examples 63: Synthesis of N-(4-(7-(2-cyano-3-methylbut-2-enamido)-1H-indazol-3-yl)pyridin-2-yl)cyclopropanecarboxamide

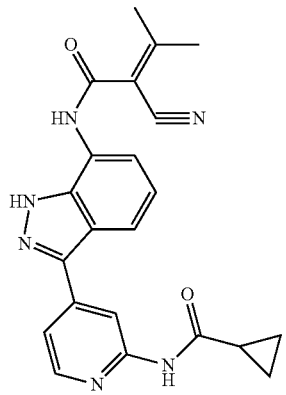 [SMILES: CC(C)=C(C#N)C(=O)Nc1cccc2c(-c3ccnc(NC(=O)C4CC4)c3)n[nH]c12]

$^1$H NMR (400 MHz, DMSO-d$_6$) δ 11.25-11.42 (m, 1H), 10.95-11.03 (m, 1H), 8.79 (s, 1H), 8.39-8.47 (m, 1H), 7.81-7.90 (m, 1H), 7.65-7.73 (m, 1H), 7.32-7.41 (m, 1H), 7.13-7.28 (m, 1H), 4.96-5.48 (m, 1H), 2.68 (s, 6H), 2.02-2.10 (m, 1H), 1.96-2.23 (m, 3H), 0.81-0.91 (m, 4H)

MS(ESI+) m/z 401 (M+H)$^+$

Experimental Example 1: Analysis of JAK1 activity inhibitory capacity (ADP-Glo™ Kinase assay)

An inhibitory effect of the inventive compound on JAK was identified as follows.

A control material and a test material were prepared through dilution at each concentration by using DMSO. At the same time, ATP (250 uM) and JAK's substrate (JAK1, IRS-1tide 40 ng/mL) were prepared through dilution in kinase buffer (40 mM Tris-HCl pH 7.5, 20 mM MgCl$_2$, 0.5 mg/mL BSA, 50 uM DTT).

A test drug for each concentration, the substrate, the ATP and JAK enzymes were mixed in an eppendorf tube, and then subjected to reaction in an incubator at 30° C. for 40 minutes.

ADP-Glo제 reagent included in ADP-Glo™ Kinase Enzyme System (Promega, USA, V9571) was added to each eppendorf tube, and then subjected to reaction in the incubator at 30° C. for 40 minutes.

A kinase detection reagent included in the ADP-Glo™ Kinase Enzyme System was inserted into the eppendorf tube, after which luminescence was measured by using Wallac Victor 2TM with an integration time set to 1 second, such that an inhibitory capacity of the test material on JAKs phosphorylation was analyzed. A concentration of the compound, at which JAK enzyme activity inhibition occurs 50% compared to the control group, was determined as IC50 (nM) of an inhibitor. The results thereof were shown in the following table 1.

TABLE 1

| Example | IC50 | Example | IC50 |
|---|---|---|---|
| 1 | +++ | 34 | ++ |
| 2 | +++ | 35 | ++ |
| 3 | ++ | 36 | ++ |
| 4 | +++ | 37 | + |
| 5 | +++ | 38 | ++ |
| 6 | +++ | 39 | +++ |
| 7 | +++ | 40 | ++ |
| 8 | ++ | 41 | ++ |
| 9 | + | 52 | + |
| 10 | +++ | 43 | + |
| 11 | ++ | 44 | + |
| 12 | + | 45 | + |
| 13 | ++ | 46 | + |
| 14 | +++ | 47 | + |
| 15 | ++ | 48 | + |
| 16 | ++ | 49 | + |
| 17 | ++ | 50 | + |
| 18 | ++ | 51 | + |
| 19 | + | 52 | + |
| 20 | + | 53 | ++ |
| 21 | ++ | 54 | ++ |
| 22 | ++ | 55 | + |
| 23 | ++ | 56 | ++ |
| 24 | +++ | 57 | +++ |
| 25 | ++ | 58 | ++ |
| 26 | + | 59 | + |
| 27 | ++ | 60 | + |
| 28 | +++ | 61 | + |
| 29 | ++ | 62 | +++ |
| 30 | +++ | 63 | + |
| 31 | +++ | 62 | +++ |
| 32 | ++ | 63 | + |
| 33 | ++ | | |

+++: IC50 <100 nM,
++: 100 nM < IC50 < 1 uM,
+: IC50 >1 uM

Industrial Applicability

A compound represented by Formula 1 according to the present invention, stereoisomers thereof or pharmaceutically acceptable salts thereof have a remarkably excellent effect on preventing or treating protein kinase-related diseases by showing a protein kinase inhibitory activity, and thus may be expected to be valuably used in a related pharmaceutical industry.

The invention claimed is:

1. A compound represented by a following Formula 1, stereoisomers thereof or pharmaceutically acceptable salts thereof:

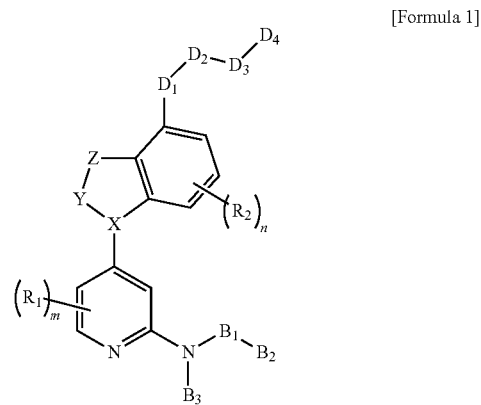

[Formula 1]

in Formula 1,

R$_1$ is H, C$_{1-6}$ alkyl, C$_{1-6}$ alkoxy, C$_{1-6}$ hydroxyalkyl, C$_{1-6}$ cyanoalkyl, C$_{1-6}$ haloalkyl, hydroxy, cyano, halogen, C(=O)—OH, C(=O)—O—C$_{1-6}$ alkyl, S(=O)$_2$—C$_{1-6}$ alkyl, aryl or heteroaryl;

X-Y-Z is C=CA$_2$-NA$_5$, N—CA$_2$=CA$_3$ or C=N—NA$_5$;

$A_2$, $A_3$ and $A_5$ are each independently H, $C_{1-6}$ alkyl, $C_{1-6}$ alkoxy, $C_{1-6}$ hydroxyalkyl, $C_{1-6}$ haloalkyl, $C_{1-6}$ cyanoalkyl, C(=O)—OH, C(=O)—O—$C_{1-6}$ alkyl, S(=O)$_2$—$C_{1-6}$ alkyl, —C(=O)—NH—$C_{1-6}$ haloalkyl, aryl or heteroaryl;

$R_2$ is H, $C_{1-6}$ alkyl, $C_{1-6}$ alkoxy, $C_{1-6}$ hydroxyalkyl, $C_{1-6}$ cyanoalkyl, $C_{1-6}$ haloalkyl, hydroxy, cyano, halogen, C(=O)—OH, C(=O)—O—$C_{1-6}$ alkyl, S(=O)$_2$—$C_{1-6}$ alkyl, aryl or heteroaryl;

n and m are each independently 0, 1, 2 or 3;

$B_1$ is —C(=O);

$B_2$ is cyclopropyl;

$B_3$ is H;

$D_1$ is —NR$_3$—;

$D_2$ is —C(=O)—, —C(=S)—, —S(=O)$_2$- or a single bond;

$D_3$ is —NR$_3$—, or a single bond;

$D_4$ is H, $C_{1-6}$ alkyl, $C_{1-6}$ alkenyl, $C_{1-6}$ haloalkyl, $C_{1-6}$ cyanoalkyl, $C_{3-7}$ cycloalkyl, 5-6-membered heterocycloalkyl, $C_{1-6}$ alkyl, in which one H is substituted with methylpiperazinyl, aryl or heteroaryl;

wherein when $D_4$ is $C_{1-6}$ alkyl in which one H is substituted with methylpiperazinyl, then $D_1$ is NH, $D_2$ is C(=O) and $D_3$ is a single bond, wherein at least one H of $C_{1-6}$ alkyl, $C_{1-6}$ alkenyl, $C_{1-6}$ haloalkyl or $C_{1-6}$ cyanoalkyl may be substituted with $C_{3-7}$ cycloalkyl, aryl, heteroaryl or cyano, at least one H of $C_{3-7}$ cycloalkyl or 5-6-membered heterocycloalkyl may be substituted with $C_{1-6}$ alkyl, $C_{1-6}$ haloalkyl, $C_{1-6}$ cyanoalkyl, cyano or halogen, and at least one H of aryl or heteroaryl may be substituted with $C_{1-6}$ alkyl, $C_{1-6}$ alkoxy, $C_{1-6}$ haloalkyl, $C_{1-6}$ hydroxyalkyl, $C_{1-6}$ cyanoalkyl, $C_{1-6}$ thioalkyl, hydroxy, cyano, nitro or halogen; and $R_3$ and $R_4$ are each independently H, $C_{1-6}$ alkyl or $C_{1-6}$ haloalkyl.

2. The compound represented by Formula 1, stereoisomers thereof or pharmaceutically acceptable salts thereof according to claim 1, wherein the compound represented by Formula 1 is the compound represented by the following Formula 2:

[Formula 2]

in Formula 2, $R_1$ is H, $C_{1-6}$ alkyl, $C_{1-6}$ alkoxy, $C_{1-6}$ hydroxyalkyl, $C_{1-6}$ cyanoalkyl, $C_{1-6}$ haloalkyl, hydroxy, cyano, halogen, C(=O)—OH, C(=O)—O—$C_{1-6}$ alkyl, S(=O)$_2$—$C_{1-6}$ alkyl, aryl or heteroaryl;

X-Y-Z is C=CA$_2$-NA$_5$, N—CA$_2$=CA$_3$ or C=N—NA$_5$;

$A_2$, $A_3$ and $A_5$ are each independently H, $C_{1-6}$ alkyl, $C_{1-6}$ alkoxy, $C_{1-6}$ hydroxyalkyl, $C_{1-6}$ haloalkyl, $C_{1-6}$ cyanoalkyl, C(=O)—OH, C(=O)—O—$C_{1-6}$ alkyl, S(=O)$_2$—$C_{1-6}$ alkyl, —C(=O)—NH—$C_{1-6}$ haloalkyl, aryl or heteroaryl;

$R_2$ is H, $C_{1-6}$ alkyl, $C_{1-6}$ alkoxy, $C_{1-6}$ hydroxyalkyl, $C_{1-6}$ cyanoalkyl, $C_{1-6}$ haloalkyl, hydroxy, cyano, halogen, C(=O)—OH, C(=O)—O—$C_{1-6}$ alkyl, S(=O)$_2$—$C_{1-6}$ alkyl, aryl or heteroaryl;

n and m are each independently 0 or 1;

$D_2$ is —C(=O)—, —C(=S)—, —S(=O)$_2$- or a single bond;

$D_3$ is —NR$_3$—, or a single bond;

$D_4$ is H, $C_{1-6}$ alkyl, $C_{1-6}$ alkenyl, $C_{1-6}$ cyanoalkyl, $C_{3-7}$ cycloalkyl, 5-6-membered heterocycloalkyl, $C_{1-6}$ alkyl in which one H is substituted with methylpiperazinyl, aryl or heteroaryl;

wherein when $D_4$ is $C_{1-6}$ alkyl in which one H is substituted with methylpiperazinyl, then $D_1$ is NH, $D_2$ is C(=O) and $D_3$ is a single bond, wherein at least one H of $C_{1-6}$ alkyl, $C_{1-6}$ alkenyl or $C_{1-6}$ cyanoalkyl may be substituted with $C_{3-7}$ cycloalkyl, aryl heteroaryl or cyano, at least one H of $C_{3-7}$ cycloalkyl or 5-6-membered heterocycloalkyl may be substituted with $C_{1-6}$ alkyl, $C_{1-6}$ haloalkyl, $C_{1-6}$ cyanoalkyl, cyano or halogen, and at least one H of aryl or heteroaryl may be substituted with $C_{1-6}$ alkyl, $C_{1-6}$ alkoxy, $C_{1-6}$ haloalkyl, $C_{1-6}$ hydroxyalkyl, $C_{1-6}$ cyanoalkyl, $C_{1-6}$ thioalkyl, hydroxy, cyano, nitro or halogen; and $R_3$ and $R_4$ are each independently H, $C_{1-6}$ alkyl or $C_{1-6}$ haloalkyl.

3. The compound represented by Formula 1, stereoisomers thereof or pharmaceutically acceptable salts thereof according to claim 1, wherein:

$R_1$ is H, $C_{1-6}$ alkyl or $C_{1-6}$ alkoxy;

X-Y-Z is C=$CA_2$-$NA_5$, N—$CA_2$=$CA_3$ or C=N-$NA_5$;

$A_2$, $A_3$ and $A_5$ are each independently H, $C_{1-6}$ alkyl or —C(=O)—NH—$C_{1-6}$ haloalkyl;

$R_2$ is H, $C_{1-6}$ alkyl or $C_{1-6}$ heteroaryl;

n and m are each independently 0 or 1;

$D_2$ is —C(=O)—;

$D_3$ is —$NR_3$—,

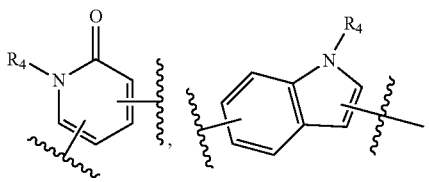

or a single bond;

$D_4$ is H, $C_{1-6}$ alkyl, $C_{1-6}$ alkenyl, $C_{1-6}$ cyanoalkyl, $C_{3-7}$ cycloalkyl, 5-6-membered heterocycloalkyl, $C_{1-6}$ alkyl, in which one H is substituted with methylpiperazinyl, aryl or heteroaryl;

wherein when $D_4$ is $C_{1-6}$ alkyl in which one H is substituted with methylpiperazinyl, then $D_1$ is NH, $D_2$ is C(=O) and $D_3$ is a single bond, wherein at least one H of $C_{1-6}$ alkyl, $C_{1-6}$ alkenyl or $C_{1-6}$ cyanoalkyl may be substituted with $C_{3-7}$ cycloalkyl, aryl, heteroaryl or cyano, at least one H of $C_{3-7}$ cycloalkyl or 4-6-membered heterocycloalkyl may be substituted with $C_{1-6}$ alkyl, $C_{1-6}$ cyanoalkyl or cyano, and at least one H of aryl or heteroaryl may be substituted with $C_{1-6}$ alkyl, $C_{1-6}$ alkoxy, $C_{1-6}$ haloalkyl or cyano; and $R_3$ and $R_4$ are each independently H, $C_{1-6}$ alkyl or $C_{1-6}$ haloalkyl.

4. The compound represented by Formula 1, stereoisomers thereof or pharmaceutically acceptable salts thereof according to claim 3, wherein:

$R_1$ is H;

X-Y-Z is N—CH=CH;

$R_2$ is H;

n and m are each independently 0;

$D_2$ is —C(=O)—;

$D_3$ is —$NR_3$—,

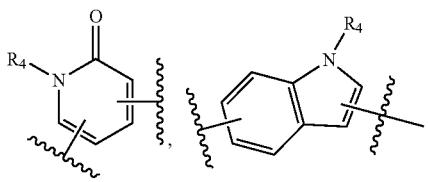

or a single bond;

$D_4$ is H, $C_{1-6}$ alkyl, $C_{1-6}$ alkenyl, $C_{1-6}$ cyanoalkyl, $C_{3-7}$ cycloalkyl, 5-6-membered heterocycloalkyl, aryl or heteroaryl;

wherein at least one H of $C_{1-6}$ alkyl, $C_{1-6}$ alkenyl or $C_{1-6}$ cyanoalkyl may be substituted with aryl, heteroaryl or cyano, at least one H of $C_{3-7}$ cycloalkyl or 5-6-membered heterocycloalkyl may be substituted with $C_{1-6}$ cyanoalkyl or cyano, and at least one H of aryl or heteroaryl may be substituted with $C_{1-6}$ alkyl, $C_{1-6}$ alkoxy, cyano, nitro or halogen; and $R_3$ and $R_4$ are each independently H or $C_{1-6}$ alkyl.

5. The compound represented by Formula 1, stereoisomers thereof or pharmaceutically acceptable salts thereof according to claim 4, wherein:

$R_1$ is H, $C_{1-6}$ alkyl or $C_{1-6}$ alkoxy;

X-Y-Z is C=$CA_2$-$NA_5$;

$A_2$ and $A_5$ are each independently H, $C_{1-6}$ alkyl or —C(=O)—NH—$C_{1-6}$ haloalkyl;

$R_2$ is H or $C_{1-6}$ alkyl;

n and m are each independently 0 or 1;

$D_2$ is —C(=O)—;

$D_3$ is —$NR_3$—,

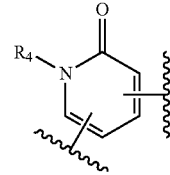

or a single bond;

$D_4$ is H, $C_{1-6}$ alkyl, $C_{1-6}$ alkenyl, $C_{1-6}$ cyanoalkyl, $C_{3-7}$ cycloalkyl, 5-6-membered heterocycloalkyl, $C_{1-6}$ alkyl in which one H is substituted with methylpiperazinyl, aryl or heteroaryl;

wherein when $D_4$ is $C_{1-6}$ alkyl in which one H is substituted with methylpiperazinyl, then $D_1$ is NH, $D_2$ is C(=O) and $D_3$ is a single bond, wherein at least one H of $C_{1-6}$ alkyl, $C_{1-6}$ alkenyl or $C_{1-6}$ cyanoalkyl may be substituted with $C_{3-7}$ cycloalkyl, heteroaryl or cyano, at least one H of $C_{3-7}$ cycloalkyl or 5-6-membered heterocycloalkyl may be substituted with $C_{1-6}$ alkyl or cyano, and at least one H of aryl or heteroaryl may be substituted with $C_{1-6}$ alkyl, $C_{1-6}$ haloalkyl or cyano; and $R_3$ and $R_4$ are each independently H, $C_{1-6}$ alkyl or $C_{1-6}$ haloalkyl.

6. The compound represented by Formula 1, stereoisomers thereof or pharmaceutically acceptable salts thereof according to claim 3, wherein:

$R_1$ is H;

X-Y-Z is C=N—NH;

$R_2$ is H;

n and m are each independently 0;

$D_2$ is —C(=O)—;

$D_3$ is a single bond;

$D_4$ is $C_{1-6}$ alkenyl wherein at least one H of $C_{1-6}$ alkenyl may be substituted with cyano; and $R_3$ is H.

7. A compound selected from the group consisting of the following compounds (1) to (63), stereoisomers thereof or pharmaceutically acceptable salts thereof:

1) N-(4-(7-(2-cyano-3-methylbut-2-enamido)-1H-indol-3-yl)pyridin-2-yl)cyclopropanecarboxamide
2) N-(3-(2-(cyclopropanecarboxamido)pyridin-4-yl)-1H-indol-7-yl)-3,5-difluorobenzamide
3) N-(3-(2-(cyclopropanecarboxamido)pyridin-4-yl)-1H-indol-7-yl)cyclohexanecarboxamide
4) N-(3-(2-(cyclopropanecarboxamido)pyridin-4-yl)-1H-indol-7-yl)-2-fluoroisonicotinamide
5) N-(3-(2-(cyclopropanecarboxamido)pyridin-4-yl)-1H-indol-7-yl)-3,5-dimethylbenzamide
6) N-(3-(2-(cyclopropanecarboxamido)pyridin-4-yl)-1H-indol-7-yl)thiazole-5-carboxamide
7) N-(4-(7-butyramido-1H-indol-3-yl)pyridin-2-yl)cyclopropanecarboxamide
8) N-(4-(7-(2-cyanoacetamido)-1H-indol-3-yl)-5-methylpyridin-2-yl)cyclopropanecarboxamide
9) N-(4-(7-(2-cyano-3-methylbut-2-enamido)-1H-indol-3-yl)-6-methylpyridin-2-yl)cyclopropanecarboxamide
10) N-(4-(7-(2-cyanoacetamido)-1H-indol-3-yl)pyridin-2-yl)cyclopropanecarboxamide
11) 4-cyano-N-(3-(2-(cyclopropanecarboxamido)pyridin-4-yl)-1H-indol-7-yl)tetrahydro-2H-pyran-4-carboxamide
12) N-(4-(7-(2-cyano-3-methylbut-2-enamido)-1H-indol-3-yl)-5-methylpyridin-2-yl)cyclopropanecarboxamide
13) N-(4-(7-(2-(1-cyanocyclopropyl)acetamido)-1H-indol-3-yl)pyridin-2-yl)cyclopropanecarboxamide
14) N-(4-(7-(2-cyanopropanamido)-1H-indol-3-yl)pyridin-2-yl)cyclopropanecarboxamide
15) N-(4-(7-(2-cyano-3-methylbut-2-enamido)-5-methyl-1H-indol-3-yl)pyridin-2-yl)cyclopropanecarboxamide
16) N-(3-(2-(cyclopropanecarboxamido)pyridin-4-yl)-5-methyl-1H-indol-7-yl)-5-methylpyrazine-2-carboxamide
17) N-(4-(7-(2,3-dimethylbut-2-enamido)-1H-indol-3-yl)pyridin-2-yl)cyclopropanecarboxamide
18) N-(4-(7-(2-(4-methylpiperazin-1-yl)propanamido)-1H-indol-3-yl)pyridin-2-yl)cyclopropanecarboxamide
19) N-(4-(7-(2-cyano-3-methylbut-2-enamido)-1H-indol-3-yl)-6-methoxypyridin-2-yl)cyclopropanecarboxamide
20) N-(4-(7-(2-cyanoacetamido)-1H-indol-3-yl)-6-methoxypyridin-2-yl)cyclopropanecarboxamide
21) N-(3-(2-(cyclopropanecarboxamido)pyridin-4-yl)-1H-indol-7-yl)-4-(trifluoromethyl)thiazole-2-carboxamide
22) (E)-N-(4-(7-(2-cyano-3-phenylacrylamido)-1H-indol-3-yl)pyridin-2-yl)cyclopropanecarboxamide
23) N-(3-(2-(cyclopropanecarboxamido)pyridin-4-yl)-1H-indol-7-yl)-1H-pyrrole-2-carboxamide
24) N-(3-(2-(cyclopropanecarboxamido)pyridin-4-yl)-1H-indol-7-yl)-4-methylnicotinamide
25) (E)-N-(4-(7-(2-cyano-3-(thiophen-2-yl)acrylamido)-1H-indol-3-yl)pyridin-2-yl)cyclopropanecarboxamide
26) N-(4-(7-(2-cyano-3-methylbut-2-enamido)-1-methyl-1H-indol-3-yl)pyridin-2-yl)cyclopropanecarboxamide
27) 4-cyano-N-(3-(2-(cyclopropanecarboxamido)pyridin-4-yl)-1H-indol-7-yl)benzamide
28) N-(3-(2-(cyclopropanecarboxamido)pyridin-4-yl)-1H-indol-7-yl)-6-methylnicotinamide
29) N-(3-(2-(cyclopropanecarboxamido)pyridin-4-yl)-1H-indol-7-yl)-6-(trifluoromethyl)nicotinamide
30) N-(3-(2-(cyclopropanecarboxamido)pyridin-4-yl)-1H-indol-7-yl)-5,6-difluoronicotinamide
31) N-(3-(2-(cyclopropanecarboxamido)pyridin-4-yl)-1H-indol-7-yl)-5-fluoronicotinamide
32) 6-chloro-N-(3-(2-(cyclopropanecarboxamido)pyridin-4-yl)-1H-indol-7-yl)nicotinamide
33) N-(3-(2-(cyclopropanecarboxamido)pyridin-4-yl)-1H-indol-7-yl)-1H-pyrazole-3-carboxamide
34) N-(3-(2-(cyclopropanecarboxamido)pyridin-4-yl)-1H-indol-7-yl)-1-methyl-2-oxo-1,2-dihydropyridine-3-carboxamide
35) 2-cyano-N-(3-(2-(cyclopropanecarboxamido)pyridin-4-yl)-1H-indol-7-yl)isonicotinamide
36) N-(3-(2-(cyclopropanecarboxamido)pyridin-4-yl)-1H-indol-7-yl)-4-ethyl-1H-pyrrole-2-carboxamide
37) 3-(2-(cyclopropanecarboxamido)pyridin-4-yl)-N-(2,2,2-trifluoroethyl)-7-(3-(2,2,2-trifluoroethyl)ureido)-1H-indole-1-carboxamide
38) N-(3-(2-(cyclopropanecarboxamido)pyridin-4-yl)-1H-indol-7-yl)-3-fluorobenzamide
39) N-(4-(7-(3-(2,2,2-trifluoroethyl)ureido)-1H-indol-3-yl)pyridin-2-yl)cyclopropanecarboxamide
40) N-(4-(4-(2-cyano-3-methylbut-2-enamido)-1H-indol-1-yl)pyridin-2-yl)cyclopropanecarboxamide
41) N-(4-(4-(2-cyanoacetamido)-1H-indol-1-yl)pyridin-2-yl)cyclopropanecarboxamide 42) N-(1-(2-(cyclopropanecarboxamido)pyridin-4-yl)-1H-indol-4-yl)-1H-pyrrole-2-carboxamid
43) N-(1-(2-(cyclopropanecarboxamido)pyridin-4-yl)-1H-indol-4-yl)-2-methylthiazole-5-carboxamid
44) N-(1-(2-(cyclopropanecarboxamido)pyridin-4-yl)-1H-indol-4-yl)-3,5-difluorobenzamide
45) N-(1-(2-(cyclopropanecarboxamido)pyridin-4-yl)-1H-indol-4-yl)-1-methyl-2-oxo-1,2-dihydropyridine-3-carboxamide
46) N-(4-(4-(2-cyano-3-(thiophen-2-yl)acrylamido)-1H-indol-1-yl)pyridin-2-yl)cyclopropanecarboxamide
47) 4-cyano-N-(1-(2-(cyclopropanecarboxamido)pyridin-4-yl)-1H-indol-4-yl)benzamide
48) N-(4-(4-(2-cyano-3-phenylacrylamido)-1H-indol-1-yl)pyridin-2-yl)cyclopropanecarboxamide
49) N-(1-(2-(cyclopropanecarboxamido)pyridin-4-yl1H-indol-4-yl)-1-methyl-1H-indole-2-carboxamide
50) 4-cyano-N-(1-(2-(cyclopropanecarboxamido)pyridin-4-yl)-1H-indol-4-yl)tetrahydro-2H-pyran-4-carboxamide
51) 2-cyano-N-(1-(2-(cyclopropanecarboxamido)pyridin-4-yl)-1H-indol-4-yl)isonicotinamide
52) N-(1-(2-(cyclopropanecarboxamido)pyridin-4-yl)-1H-indol-4-yl)-2-fluoroisonicotinamide
53) N-(1-(2-(cyclopropanecarboxamido)pyridin-4-yl)-1H-indol-4-yl)-2,3-difluoroisonicotinamide
54) N-(4-(4-(2-cyanopropanamido)-1H-indol-1-yl)pyridin-2-yl)cyclopropanecarboxamide
55) N-(1-(2-(cyclopropanecarboxamido)pyridin-4-yl)-1H-indol-4-yl)-1H-pyrazole-3-carboxamide
56) N-(1-(2-(cyclopropanecarboxamido)pyridin-4-yl)-1H-indol-4-yl)-3-fluoro-4-methoxybenzamide
57) (1R,2S)-2-cyano-N-(1-(2-(cyclopropanecarboxamido)pyridin-4-yl)-1H-indol-4-yl)cyclopropane-1-carboxamide
58) N-(4-(4-(2-(1-cyanocyclopropyl)acetamido)-1H-indol-1-yl)pyridin-2-yl)cyclopropanecarboxamide
59) N-(1-(2-(cyclopropanecarboxamido)pyridin-4-yl)-1H-indol-4-yl)-6-methylnicotinamide
60) N-(4-(4-(2,3-dimethylbut-2-enamido)-1H-indol-1-yl)pyridin-2-yl)cyclopropanecarboxamide
61) N-(4-(4-(3-(2,4-difluorophenyl)ureido)-1H-indol-1-yl)pyridin-2-yl)cyclopropanecarboxamide
62) N-(4-(4-(3-(2,2,2-trifluoroethyl)ureido)-1H-indol-1-yl)pyridin-2-yl)cyclopropanecarboxamide
63) N-(4-(7-(2-cyano-3-methylbut-2-enamido)-1H-indazol-3-yl)pyridin-2-yl)cyclopropanecarboxamide.

8. A pharmaceutical composition comprising the compound, stereoisomers thereof or pharmaceutically acceptable salts thereof according to claim 1, as an active ingredient.

9. A method for preventing or treating protein kinase-related diseases, comprising a step of administering a therapeutically effective amount of the compound, stereoisomers thereof or pharmaceutically acceptable salts thereof according to claim 1, into a subject.

10. The method according to claim 9, wherein the protein kinase-related diseases are selected from the group consisting of cancers, autoimmune diseases, neurological diseases, metabolic diseases and infections.

* * * * *